(12) United States Patent
Berthier et al.

(10) Patent No.: US 12,127,837 B2
(45) Date of Patent: Oct. 29, 2024

(54) DEVICES, SYSTEMS AND METHODS FOR GRAVITY-ENHANCED MICROFLUIDIC COLLECTION, HANDLING AND TRANSFERRING OF FLUIDS

(71) Applicant: Tasso, Inc., Seattle, WA (US)

(72) Inventors: Erwin Berthier, Seattle, WA (US); Ben Casavant, Seattle, WA (US); Ben Moga, Soquel, CA (US)

(73) Assignee: Tasso, Inc., Seattle, WA (US)

( * ) Notice: Subject to any disclaimer, the term of this patent is extended or adjusted under 35 U.S.C. 154(b) by 0 days.

(21) Appl. No.: 18/168,459

(22) Filed: Feb. 13, 2023

(65) Prior Publication Data

US 2023/0371865 A1 Nov. 23, 2023

Related U.S. Application Data

(63) Continuation of application No. 17/323,567, filed on May 18, 2021, now Pat. No. 11,998,334, which is a
(Continued)

(51) Int. Cl.
*A61B 5/15* (2006.01)
*A61B 5/151* (2006.01)
*B01L 3/00* (2006.01)

(52) U.S. Cl.
CPC .. *A61B 5/150358* (2013.01); *A61B 5/150022* (2013.01); *A61B 5/150099* (2013.01);
(Continued)

(58) Field of Classification Search
CPC ........ A61B 5/150358; A61B 5/150022; A61B 5/150099; A61B 5/150251; A61B 5/150343; A61B 5/150412; A61B 5/150503; A61B 5/150977; A61B 5/15113; A61B 5/15142; A61B 5/1411;
(Continued)

(56) References Cited

U.S. PATENT DOCUMENTS 3,623,475 A 11/1971 Sanz et al.
4,024,857 A 5/1977 Blecher et al.
(Continued)

FOREIGN PATENT DOCUMENTS

CN 1917810 A 2/2007
CN 102309331 4/2013
(Continued)

OTHER PUBLICATIONS

Javier Atencia and David J. Beebe, "Controlled Microfluidic Interfaces," Sep. 29, 2005, pp. 648-655, vol. 437, No. 7059, Publisher: Nature.
(Continued)

*Primary Examiner* — Patrick Fernandes
(74) *Attorney, Agent, or Firm* — Perkins Coie LLP

(57) ABSTRACT

The disclosed apparatus, systems and methods relate to the collection of bodily fluids through the use of gravity and microfluidic properties by way of a collector. The collector can make use of microfluidic networks connected to collection sites on the skin of a subject to gather and shuttle blood into a reservoir by a combination of capillary action and gravitational forces. The collected fluid is moved through the microfluidic networks and into the reservoir by a variety of approaches.

29 Claims, 39 Drawing Sheets

Related U.S. Application Data continuation of application No. 16/807,690, filed on Mar. 3, 2020, now Pat. No. 11,033,212, which is a continuation of application No. 14/816,994, filed on Aug. 3, 2015, now Pat. No. 10,779,757.

(60) Provisional application No. 62/032,266, filed on Aug. 1, 2014.

(52) U.S. Cl.
CPC .. *A61B 5/150251* (2013.01); *A61B 5/150343* (2013.01); *A61B 5/150412* (2013.01); *A61B 5/150503* (2013.01); *A61B 5/150977* (2013.01); *A61B 5/15113* (2013.01); *A61B 5/15142* (2013.01); *B01L 3/502715* (2013.01); *B01L 2400/0406* (2013.01); *B01L 2400/0457* (2013.01)

(58) Field of Classification Search
CPC ..... B01L 2400/0487; B01L 2300/0816; B01L 3/5027; B01L 2400/0406
See application file for complete search history.

(56) References Cited

U.S. PATENT DOCUMENTS

| | | | |
|---|---|---|---|
| 4,653,513 A | 3/1987 | Dombrowski |
| 4,660,570 A | 4/1987 | Dombrowski |
| 4,775,336 A | 10/1988 | Paulo |
| 4,775,366 A | 10/1988 | Rosenblatt |
| 5,035,865 A | 7/1991 | Inaba et al. |
| 5,110,557 A | 5/1992 | Brown et al. |
| 5,145,565 A | 9/1992 | Kater et al. |
| 5,318,584 A | 6/1994 | Lange et al. |
| 5,320,607 A | 6/1994 | Ishibashi |
| 5,356,420 A | 10/1994 | Czernecki et al. |
| 5,569,287 A | 10/1996 | Tezuka et al. |
| 5,611,809 A | 3/1997 | Marshall et al. |
| 5,624,458 A | 4/1997 | Lipscher |
| 5,636,640 A | 6/1997 | Staehlin |
| 5,662,127 A | 9/1997 | De Vaughn |
| 5,772,677 A | 6/1998 | Mawhirt et al. |
| 6,010,519 A | 1/2000 | Mawhirt et al. |
| 6,042,595 A | 3/2000 | Morita |
| 6,152,942 A | 11/2000 | Brenneman et al. |
| 6,221,089 B1 | 4/2001 | Mawhirt |
| 6,364,890 B1 | 4/2002 | Lum et al. |
| 6,419,661 B1 | 7/2002 | Kuhr et al. |
| 6,432,120 B1 | 8/2002 | Teo |
| 6,605,048 B1 | 8/2003 | Levin et al. |
| 6,659,975 B2 | 12/2003 | Amano et al. |
| 6,660,018 B2 | 12/2003 | Lum et al. |
| 6,706,000 B2 | 3/2004 | Perez et al. |
| 6,821,485 B2 | 11/2004 | Beebe et al. |
| 6,849,052 B2 | 2/2005 | Uchigaki |
| 6,856,821 B2 | 2/2005 | Johnson |
| 6,929,650 B2 | 8/2005 | Fukuzawa et al. |
| 7,160,313 B2 | 1/2007 | Galloway et al. |
| 7,316,698 B1 | 1/2008 | Galloway et al. |
| 7,344,499 B1 | 3/2008 | Prausnitz et al. |
| 7,374,545 B2 | 5/2008 | Alroy et al. |
| 7,452,365 B2 | 11/2008 | Galloway et al. |
| 7,666,149 B2 | 2/2010 | Simons et al. |
| 7,670,300 B2 | 3/2010 | Vreeke et al. |
| 7,704,265 B2 | 4/2010 | Schraga |
| 7,775,991 B2 | 8/2010 | Feaster et al. |
| 7,803,123 B2 | 9/2010 | Perez et al. |
| 7,846,110 B2 | 12/2010 | Kloepfer et al. |
| 7,879,058 B2 | 2/2011 | Ikeda |
| 7,981,131 B2 | 7/2011 | Shi |
| 7,998,161 B2 | 8/2011 | Shi |
| 8,025,628 B2 | 9/2011 | Wong et al. |
| 8,034,628 B2 | 10/2011 | Harrison et al. |
| 8,361,099 B2 | 1/2013 | Schosnig et al. |
| 8,382,681 B2 | 2/2013 | Escutia et al. |
| 8,454,642 B2 | 6/2013 | Schraga |
| 8,512,367 B2 | 8/2013 | Robbins et al. |
| 8,551,047 B2 | 10/2013 | Burns et al. |
| 8,696,596 B2 | 4/2014 | Douglas et al. |
| 8,715,307 B2 | 5/2014 | Sun |
| 8,728,411 B2 | 5/2014 | Beebe et al. |
| 8,808,202 B2 | 8/2014 | Brancazio |
| 8,821,412 B2 | 9/2014 | Gonzalez-Zugasti et al. |
| 8,840,634 B2 | 9/2014 | Sun et al. |
| 8,876,846 B2 | 11/2014 | Schraga |
| 9,033,898 B2 | 5/2015 | Chickering, III et al. |
| 9,138,184 B2 | 9/2015 | Lum |
| 9,220,447 B2 | 12/2015 | Richter et al. |
| 9,289,763 B2 | 3/2016 | Berthier et al. |
| 9,724,031 B2 | 8/2017 | Yi et al. |
| 9,839,384 B2 | 12/2017 | Escutia et al. |
| 9,987,629 B2 | 6/2018 | Berthier et al. |
| 10,034,627 B2 | 7/2018 | Booker et al. |
| 10,105,080 B1 | 10/2018 | Kam et al. |
| 10,426,390 B2 | 10/2019 | Berthier et al. |
| 10,492,716 B2 | 12/2019 | Berthier et al. |
| 10,765,361 B2 | 9/2020 | Krasnow et al. |
| 10,779,757 B2 | 9/2020 | Berthier et al. |
| 11,033,212 B2 | 6/2021 | Berthier et al. |
| 11,395,614 B2 | 7/2022 | Berthier et al. |
| 11,510,659 B2 | 11/2022 | Berthier et al. |
| 11,642,057 B2 | 5/2023 | Berthier et al. |
| 2001/0044615 A1 | 11/2001 | Amano et al. |
| 2002/0022789 A1 | 2/2002 | Perez et al. |
| 2002/0055711 A1 | 5/2002 | Lavi et al. |
| 2002/0097632 A1 | 7/2002 | Kellogg et al. |
| 2003/0018282 A1 | 1/2003 | Effenhauser et al. |
| 2003/0028125 A1 | 2/2003 | Yuzhakov et al. |
| 2003/0216767 A1 | 11/2003 | List et al. |
| 2003/0225362 A1 | 12/2003 | Currie et al. |
| 2004/0019300 A1 | 1/2004 | Leonard |
| 2004/0092996 A1 | 5/2004 | List et al. |
| 2004/0176704 A1 | 9/2004 | Stevens et al. |
| 2004/0243105 A1 | 12/2004 | Swan et al. |
| 2005/0136501 A1 | 6/2005 | Kuriger |
| 2005/0236566 A1 | 10/2005 | Liu |
| 2006/0039829 A1 | 2/2006 | Suk et al. |
| 2006/0052809 A1 | 3/2006 | Karbowniczek et al. |
| 2006/0171855 A1 | 8/2006 | Yin et al. |
| 2006/0293611 A1 | 12/2006 | Calasso et al. |
| 2007/0010841 A1 | 1/2007 | Teo et al. |
| 2007/0161106 A1 | 7/2007 | Jervis et al. |
| 2007/0161926 A1 | 7/2007 | Imamura et al. |
| 2007/0212266 A1 | 9/2007 | Johnston et al. |
| 2007/0213633 A1 | 9/2007 | Herbrechtsmeier et al. |
| 2007/0213638 A1 | 9/2007 | Herbrechtsmeier et al. |
| 2007/0260193 A1 | 11/2007 | Chin et al. |
| 2008/0028821 A1 | 2/2008 | Horkiike et al. |
| 2008/0097502 A1 | 4/2008 | Winters-Hilt et al. |
| 2008/0138890 A1 | 6/2008 | Horiike et al. |
| 2009/0036915 A1 | 2/2009 | Karbowniczek et al. |
| 2009/0075390 A1 | 3/2009 | Linder et al. |
| 2009/0118753 A1 | 5/2009 | Dicesare et al. |
| 2009/0165876 A1 | 7/2009 | Atkin et al. |
| 2009/0187118 A1 | 7/2009 | Kim et al. |
| 2009/0192486 A1 | 7/2009 | Wilmot et al. |
| 2009/0299224 A1 | 12/2009 | Yoo |
| 2010/0023045 A1 | 1/2010 | Macho et al. |
| 2010/0049091 A1 | 2/2010 | Haar |
| 2010/0145377 A1 | 6/2010 | Lai et al. |
| 2010/0256465 A1 | 10/2010 | Bernstein et al. |
| 2010/0256524 A1 | 10/2010 | Levinson et al. |
| 2010/0326826 A1 | 12/2010 | Harrison et al. |
| 2011/0009847 A1 | 1/2011 | Levinson et al. |
| 2011/0029006 A1 | 2/2011 | Leong |
| 2011/0077553 A1 | 3/2011 | Alroy |
| 2011/0087134 A1 | 4/2011 | Lathrop et al. |
| 2011/0165022 A1 | 7/2011 | Meathrel et al. |
| 2011/0257498 A1 | 10/2011 | Amano et al. |
| 2011/0306853 A1 | 12/2011 | Black et al. |
| 2011/0312773 A1 | 12/2011 | Silbebrook et al. |
| 2012/0010529 A1 | 1/2012 | Chickering, III et al. |
| 2012/0043391 A1 | 3/2012 | Delamarche et al. |

(56) References Cited

U.S. PATENT DOCUMENTS

| | | |
|---|---|---|
| 2012/0048931 A1 | 3/2012 | Delamarche et al. |
| 2012/0088249 A1 | 4/2012 | Jovanovich et al. |
| 2013/0211289 A1 | 8/2013 | Moga et al. |
| 2014/0038306 A1 | 2/2014 | Berthier et al. |
| 2014/0042094 A1 | 2/2014 | Montagu et al. |
| 2014/0190894 A1 | 7/2014 | Beebe et al. |
| 2014/0273056 A1 | 9/2014 | Beebe et al. |
| 2015/0238705 A1 | 8/2015 | Gravesen et al. |
| 2015/0342509 A1 | 12/2015 | Peeters et al. |
| 2016/0051981 A1 | 2/2016 | Berthier et al. |
| 2016/0081606 A1 | 3/2016 | Russ et al. |
| 2016/0174888 A1 | 6/2016 | Berthier et al. |
| 2016/0256095 A1 | 9/2016 | Krasnow et al. |
| 2016/0256106 A1 | 9/2016 | Krasnow et al. |
| 2017/0172481 A1 | 6/2017 | Berthier et al. |
| 2018/0008183 A1 | 1/2018 | Chickering, III et al. |
| 2018/0078241 A1 | 3/2018 | Moga et al. |
| 2018/0228418 A1 | 8/2018 | Berthier et al. |
| 2019/0015827 A1 | 1/2019 | Berthier et al. |
| 2020/0037940 A1 | 2/2020 | Berthier et al. |
| 2020/0085414 A1 | 3/2020 | Berthier et al. |
| 2020/0146606 A1 | 5/2020 | Casavant et al. |
| 2020/0178870 A1 | 6/2020 | Berthier et al. |
| 2020/0323473 A1 | 10/2020 | Berthier et al. |
| 2021/0196245 A1 | 7/2021 | Berthier et al. |
| 2022/0039710 A1 | 2/2022 | Berthier et al. |
| 2023/0172505 A1 | 6/2023 | Berthier et al. |
| 2023/0181072 A1 | 6/2023 | Berthier et al. |

FOREIGN PATENT DOCUMENTS

| | | |
|---|---|---|
| CN | 103370007 | 10/2013 |
| CN | 103874460 | 6/2014 |
| CN | 107438394 A | 9/2016 |
| EP | 1389443 | 2/2004 |
| EP | 1808128 | 7/2007 |
| EP | 2439540 | 4/2012 |
| EP | 2484448 | 8/2012 |
| EP | 2863798 | 4/2015 |
| EP | 3725226 A1 | 10/2020 |
| JP | 2016526466 | 9/2016 |
| JP | 2016032614 | 8/2018 |
| WO | WO2002100253 | 12/2002 |
| WO | WO2008053743 | 5/2008 |
| WO | WO2013112877 | 8/2013 |
| WO | WO2014088606 | 6/2014 |
| WO | WO2016019388 | 2/2016 |
| WO | WO2017112793 | 6/2017 |
| WO | WO2018022535 | 2/2018 |
| WO | WO2018057760 | 3/2018 |
| WO | WO2019114343 | 6/2019 |
| WO | WO2014018558 | 1/2020 |
| WO | WO2020056382 | 3/2020 |
| WO | WO2020102281 | 5/2020 |
| WO | WO2020223710 | 11/2020 |
| WO | WO2021041881 | 3/2021 |

OTHER PUBLICATIONS

Scott M. Berry, Elaine T. Alarid, and David J. Beebe, "One-step purification of nucleic acid for gene expression analysis via Immiscible Filtration Assisted by Surface Tension (IFAST)," May 21, 2011, pp. 1747-1753, vol. 11, No. 10, Publisher: Lab Chip.

David Chunningham, Timothy Henning, Eric Shain, Douglas Young Jurgen Hanning, Eric Barua, and Raphael Lee, "Blood extraction from lancet wounds using vacuum combined with skin stretching," Nov. 9, 2001, pp. 1089-1096, vol. 92, No. 3, Publisher: J Appl Physiol.

H Fruhstorfer, H Lange, "Capillary blood sampling: how much pain is necessary? Part 3: Pricking the finger can be less painful," Feb. 1, 1995, pp. 253-254, vol. 12, No. 6, Publisher: Practical Diabetes International.

H Fruhstorfer and T Muller, "Capillary blood sampling: how much pain is necessary? Part 1: Comparison of existing finger stick devices," Feb. 1, 1995, pp. 72-74, vol. 12, No. 2, Publisher: Practical Diabetes International.

H Fruhstorfer, T Muller, and E Scheer, "Capillary blood sampling: how much pain is necessary? Part 2: Relation between penetration depth and puncture pain," Feb. 1, 1995, pp. 184-185, vol. 12, No. 4, Publisher: Practical Diabetes International.

Heinrich Fruhstorfer, Gunther Schmelzeisen-Redeker, and Thomas Weiss, "Capillary Blood Sampling: relation between lancet diameter, lancing pain and blood volume," 1999, pp. 283-286, vol. 3, No. 3, Publisher: European Journal of Pain.

H Fruhstorfer, K Selzer, and O Selbman, "Capillary blood sampling: how much pain is necessary? Part 4: Comparison of lancets for automatic lancing devices," Jul. 24, 1995, pp. 58-60, vol. 13, No. 2, Publisher: Practical Diabetes International.

Heinrich Fruhstorfer, "Capillary Blood Sampling: the pain of single-use lancing devices," 2000, pp. 301-305, vol. 4, No. 3, Publisher: European Journal of Pain.

Chia-Hsien Hsu, Chihchen Chen, and Albert Folch, "Microcanals for micropipette access to single cells in microfluidic environments," Jul. 23, 2004, pp. 420-424, vol. 4, No. 5, Publisher: Lab Chip.

J. Berthier, F. Loe-Mie, V.-M. Tran, S Schoumacker, F. Mittler, G. Marchand, N. Sarrut, "On the Pinning of Interfaces on Micropillar Edges," Jun. 3, 2009, pp. 296-303, vol. 338, No. 1, Publisher: J Colloid Interface Sci.

Sung Hoon Lee, Austen James Heinz, Sunghwan Shin, Young-Gyun Jung, Sung-Eun Choi, Wook Park, Jung-Hye Roe, Sunghoon Kwon, "Capillary Based Patterning of Cellular Communities in the Laterally Open Channels," Apr. 1, 2010, pp. 2900-2906, vol. 82, No. 7, Publisher: Anal Chem.

"Open Microfluidic and Nanofluidic systems," Feb. 15, 2005, pp. 1848-1852, vol. 102, Publisher: PNAS.

Nuno M. Oliveira, Ana I. Neto, Wenlong Song, and Joao F. Mano, "Two-Dimensional Open Microfluidic Devices by Tuning the Wettability on Patterned Superhydrophobic Polymeric Surface," Aug. 6, 2010, vol. 3:085205, Publisher: Appl Phys Express.

Jessica Olofsson, Johan Pihl, Jon Sinclair, Eskil Sahlin, Mattias Karlsson, and Owe Orwar, "A Microfluidics Approach to the Problem of Creating Separate Solution Environments Accessible from Macroscopic Volumes", Sep. 1, 2004, pp. 4968-4976, vol. 76, No. 17, Publisher: Anal Chem.

Ralf Seemann, Martin Brinkmann, Edward J. Kramer, Frederick F. Lange, and Reinhard Lipowsky, "Wetting morphologies at microstructured surfaces," Dec. 16, 2004, pp. 1848-1852, vol. 102, No. 6, Publisher: Proc Natl Acad Sci USA.

Bin Zhao, Jeffrey S. Moore, and David J. Beebe, "Surface-Directed Liquid Flow Inside Microchannels," Feb. 9, 2001, pp. 1023-1026, vol. 291, No. 5506, Publisher: Science.

Australian Examination Report issued for Australian Application No. 2015295983; Applicant: Tasso, Inc., dated Jun. 18, 2019, 6 pages.

English translation of Chinese Office Action issued for Chinese Application No. 201580053311.7; Applicant: Tasso, Inc., dated May 5, 2019, 18 pages.

First European Examination Report issued for European Application No. 15827298.9; Applicant: Tasso, Inc., dated Aug. 10, 2018, 7 pages.

Intention to Grant received for European Application No. 15827298.9; Applicant: Tasso, Inc., dated Mar. 10, 2020, 5 pages.

International Preliminary Report on Patentability received for PCT Application No. PCT/US2015/043472; Applicant: Tasso, Inc., dated Feb. 16, 2017, 9 pages.

International Search Report and Written Opinion received for PCT Application No. PCT/US13/51731; Applicant: Erwin Berthier, dated Jan. 2, 2014, 16 pages.

International Search Report and Written Opinion received for PCT Application No. PCT/US16/68077; Applicant: Tasso, Inc., dated Mar. 10, 2017, 16 pages.

International Search Report and Written Opinion received for PCT Application No. PCT/US19/51186; Applicant: Tasso, Inc., dated Nov. 26, 2019, 12 pages.

(56) References Cited

OTHER PUBLICATIONS

Australian First Patent Examination Report received for Patent Application No. 2013293078; Applicant: Tasso, Inc., dated Sep. 7, 2016, 3 pages.

Die Yang, "Dynamics of Capillary-Driven Flow in Open Microchannels," Journal of Physical Chemistry C, Aug. 16, 2011, vol. 115. pp. 18761-18769.

English Translation of Japanese Office Action received for Patent Application No. 2015-524399; Applicant: Tasso, Inc., dated Aug. 8, 2017, 13 pages.

Second Examination Report received for European Patent Application No. 15827298.9; Applicant: Tasso, Inc., dated Jul. 4, 2019, 6 pages.

English Translation of Chinese Office Action received for Patent Application No. 201680082347.2; Applicant: Tasso, Inc., dated Aug. 12, 2020, 16 pages.

Extended Supplementary European Search Report received for EP Application No. 16880039.9; Applicant: Tasso, Inc, dated May 8, 2019, 10 pages.

International Search Report and Written Opinion received for PCT Application No. PCT/US2015/043472; Applicant: Tasso, Inc., dated Nov. 12, 2015, 16 pages.

Extended Supplementary European Search Report received for EP Application No. 19861013.1; Applicant: Tasso, Inc, dated Apr. 11, 2022, 10 pages.

Tenenbaum, "Simple sample: Federal grant advances pain-free blood tests from UW startup," https://news.wisc.edu/simple-sample-federal-grant-advances-pain-free-blood-tests-from-uw-startup, Apr. 14, 2015.

Chinese First Office Action issued for Chinese Application No. 202110860739.X; Applicant: Tasso, Inc., Date of Mailing: Aug. 26, 2023, 7 pages.

English Translation of Japanese Office Action received for Patent Application No. 2021-513338; Applicant: Tasso, Inc., Date of Mailing: Aug. 28, 2023, 4 pages.

Cunningham et al., "Blood extraction from lancet wounds using vacuum combined with skin stretching," Nov. 9, 2001, pp. 1089-1096, vol. 92, No. 3, J. Appl. Physiol., 8 pages.

Chinese First Office Action issued for Chinese Application No. 201980005543.3; Applicant: Tasso, Inc., Date of Mailing: Jan. 4, 2024, 12 pages.

Chinese Second Office Action issued for Chinese Application No. 202110860739X; Applicant: Tasso, Inc., Date of Mailing: May 18, 2024, 6 pages.

FIG. 3B     FIG. 3C

DEVICES, SYSTEMS AND METHODS FOR GRAVITY-ENHANCED MICROFLUIDIC COLLECTION, HANDLING AND TRANSFERRING OF FLUIDS

CROSS-REFERENCE TO RELATED APPLICATIONS

This application is a continuation of U.S. patent application Ser. No. 17/323,567, filed May 18, 2021, and titled "Devices, Systems and Methods for Gravity-Enhanced Microfluidic Collection, Handling and Transferring of Fluids," which is a continuation of U.S. patent application Ser. No. 16/807,690, filed Mar. 3, 2020, and titled "Devices, Systems and Methods for Gravity-Enhanced Microfluidic Collection, Handling and Transferring of Fluids," now issued as U.S. Pat. No. 11,033,212, which is a continuation of U.S. patent application Ser. No. 14/816,994, filed Aug. 3, 2015, now issued as U.S. Pat. No. 10,779,757 and titled "Devices, Systems and Methods for Gravity-Enhanced Microfluidic Collection, Handling and Transferring of Fluids," which claims priority to U.S. Provisional Patent Application No. 62/032,266, filed Aug. 1, 2014, and titled "Gravity-Enhanced Microfluidic Devices and Methods for Handling and Transferring Fluids," each of which is incorporated by reference in its entirety.

STATEMENT REGARDING FEDERALLY SPONSORED RESEARCH

This invention was made with government support under Award #W31P4Q-14-C-0006 from the Defense Advanced Research Projects Agency (DARPA). The government has certain rights in the invention.

TECHNICAL FIELD

The disclosed technology relates generally to the collection of bodily fluids, and in particular, to the devices, methods, and design principles allowing the collection of bodily fluids into a receptacle and, in certain embodiments, the process of acting on the fluid being collected with the utilization of gravity to add functionality. This has implications not only for active fluid collection, but also on downstream processing of the receptacle, including its presentation to equipment and processes.

BACKGROUND

Devices, systems and methods to collect bodily fluids are necessary devices for the growing field of personalized medicine. As point-of-care devices continue to improve, an often overlooked area lies within the collection of samples from untrained users. Currently, biological samples are most commonly obtained via either simple-to-use methods or devices, as with generic lancing devices, or trained personnel, as with phlebotomy venipunctures. In order to transfer the bodily fluid to a container, receptacle, or an analysis device, multiple steps are required that are time consuming and/or cumbersome. To circumvent these problems, there is a need for devices that are able to collect samples in a simple manner and have an integrated fluidic transfer to a container or receptacle that houses the samples.

Thus, there is a need in the art for improved microfluidic devices that utilize gravity and capillary forces for fluid handling and transfer, and related systems and methods.

SUMMARY

Discussed herein are various embodiments of the collection device, as well as associated systems and methods for its use. For brevity, these embodiments may be described in relation to a "collector," though that is not intended to limit the scope of the disclosure in any way. Further, the discussion of microfluidic channels may comprise open and closed channels, as well as channels featuring both open and closed portions.

In Example 1, microfluidic collection system for drawing blood from a subject comprising a collector further comprising a housing, at least one collection site, a microfluidic network further comprising at least one microfluidic channel disposed within the housing, and at least one outflow channel in fluidic communication with the microfluidic network, and at least one reservoir in fluidic communication with the at least one collection site by way of the outflow channel, wherein the system is configured to be placed on a subject's skin to draw blood, and the at least one microfluidic network is configured to promote the flow of fluids from the collection site to the at least one outflow channel.

In Example 2, the system of Example 1, further comprising an actuator configured to facilitate the puncture of skin.

In Example 3, the system of Example 1, wherein the at least one microfluidic channel further comprises a microfluidic channel geometry and a contact angle, and further wherein the at least one microfluidic channel is configured to promote the flow of fluids by at least one of capillary action and gravitational force.

In Example 4, the system of Example 3, wherein the collector and at least one microfluidic channel is configured to have a flow position and a stop position.

In Example 5, the system of Example 3, further comprising at least one open microfluidic channel.

In Example 6, the system of Example 3, further comprising at least one open microfluidic channel and at least one closed microfluidic channel.

In Example 7, the system of Example 3, wherein the microfluidic network further comprises at least one ramp.

In Example 8, the system of Example 3, wherein the microfluidic network further comprises at least one surface tension valve.

In Example 9, the system of Example 8, wherein the surface tension valve is configured to regulate the flow of fluids through the microfluidic network based on the orientation of the microfluidic network.

In Example 10, the system of Example 3, further comprising a coupling portion.

In Example 11, the system of Example 10, wherein the reservoir is detachable, and the coupling portion is further configured to receive a detachable reservoir.

In Example 12, gravity-enhanced collection system comprising a collector, further comprising a housing, a microfluidic network, further comprising at least one microfluidic channel disposed within the housing, at least one collection site disposed within the housing, at least one outflow channel, and at least one reservoir, wherein the at least one collection site is in microfluidic communication with the outflow channel by way of the microfluidic network so as to promote the flow of fluid to the reservoir by way of the outflow channel into the reservoir.

In Example 13, the system of Example 12, wherein the device is configured to use gravity to enhance fluid collection.

In Example 14, the system of Example 13, wherein the reservoir is a detachable reservoir.

In Example 15, the system of Example 13, wherein the outflow channel is configured to prevent backflow.

In Example 16, the system of Example 13, wherein the at least one microfluidic channel further comprises an open microfluidic channel and a closed microfluidic channel in fluidic communication with one another.

In Example 17, the system of claim 16 wherein the open microfluidic channel and closed microfluidic channels are in fluidic communication with one another.

In Example 18, the system of claim 16 further comprising a ramp. In certain Examples, this ramp may comprise an open microfluidic channel with at least one wetted surface defining a wetted perimeter length, wherein the wetted surface contacts a fluid flowing through the channel at a contact angle, and at least one free surface comprising an open air-liquid interface defining a free perimeter length, wherein the ratio of the free perimeter length to the wetted perimeter length is less than the cosine of the contact angle, thereby enabling spontaneous capillary flow.

In Example 19, the system of channel 15, wherein the at least one microfluidic channel is capable of timed fluid delivery.

In Example 20, a method of drawing blood from a subject, comprising providing a blood collection device, comprising a housing, a microfluidic network further comprising at least one microfluidic channel disposed within the housing and at least one collection site, at least one outflow channel in fluidic communication with the microfluidic network, and at least one reservoir in fluidic communication with the at least one collection site by way of the network and outflow channel, placing the fluid connection device on the skin of the subject, puncturing the subject's skin so as to pool fluid, collecting pooling fluid from the skin and transporting it to the reservoir by way of the microfluidic network.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 3B is a side view of the collector of FIG. 3A.

FIG. 3C is a side view of the collector of FIG. 3A from an alternate angle.

DETAILED DESCRIPTION

Figure 1A:
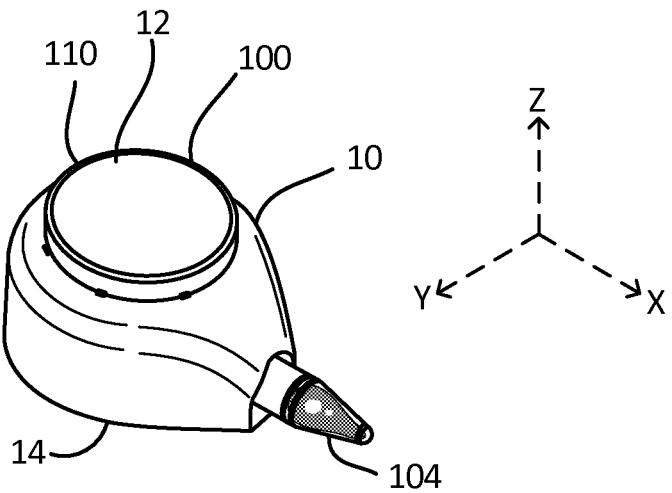
FIG. 1A is a perspective view of the collector, according to an exemplary embodiment.

The various embodiments disclosed or contemplated herein relate to a single device that can be used by untrained or minimally-trained persons to both collect bodily fluid and seamlessly contain the bodily fluid, and related systems and methods.

The present disclosure describes the use of microfluidic methods that utilize gravity within open microfluidic channels in a manner which complements the capillary driven flow, and enables new applications that were previously difficult to achieve, including, but not limited to, adding a detachable tube, incorporating one-way flow valves, including geometries more amenable to manufacturing methods, and using engineered connection methods.

It is understood that the various embodiments of the devices and related methods and systems disclosed herein can be incorporated into or used with any other known medical devices, systems, and methods. For example, the various embodiments disclosed herein may be incorporated into or used with any of the medical devices and systems disclosed in co-pending U.S. application Ser. No. 13/949,108, filed Jul. 23, 2013, entitled "Methods, Systems, and Devices Relating to Open Microfluidic Channels," and U.S. application Ser. No. 13/750,526, filed Jan. 25, 2013, entitled "Handheld Device for Drawing, Collecting, and Analyzing Bodily Fluid," both of which are hereby incorporated herein by reference in their entireties.

Disclosed herein are various embodiments of an integrated collection and containment device that collects and transfers the bodily fluid from a subject's tissue into an easily detachable tube or reservoir. Previous technologies approached the transfer of the bodily fluid in a linear manner: one device enabled the bodily fluid to exit the tissue and another device was used to collect the bodily fluid. In contrast, the implementations disclosed herein simplify the process of bodily fluid collection by integrating the collection of the bodily fluid directly with the containment of bodily fluid within the same device.

Certain embodiments utilize gravity as a passive energy source to overcome surface tension in specific and defined areas so as to facilitate the transfer of fluids. As will become apparent, exemplary embodiments described herein include various apparatuses, systems and methods for collecting fluid samples, such as bodily fluids, and enabling the containment of those samples in containers that are easily attached and removed from a collection device. Exemplary embodiments are for use in medical devices, at-home diagnostic devices, and laboratory analysis platforms and equipment.

The ability to specifically and intentionally use gravity to overcome or enhance capillary force is useful for the manufacturability of microfluidic channels. When utilizing gravitational force in the direction of the fluid flow, the gravitational force acts as an extra, or additive force to promote the flow of fluid in places that have an unfavorable capillary drawing force for a variety of reasons. For example, materials that have a high surface energy (and thus a large contact angle) often have difficulty drawing fluid. If the channel is oriented such that the input is above the output, fluid will naturally be forced through the channel due to gravity, overcoming the unfavorable surface properties of the plastic and thus enabling a wider range of plastics that can be used in a gravity-assisted capillary device. In certain implementations, this benefit can extend to overcoming various manufacturing defects, allowing these fluid systems to be particularly robust and easy to manufacture, as less precision may be required. Manufacturing defects can include small surface or dimensional imperfections that can create fluidic pinning ridges that would otherwise stop fluid flow, improper manufacturing depth that would reduce spontaneous capillary flow, rounded channel corners, dirt or dust particulates that may land in the channel during assembly, and other imperfections that may exist in the channel and hinder fluid progression in an entirely capillary driven device.

The creation or production of small, narrow channels via injection molding reveals a difficulty in the fabrication of previous microfluidic devices. The aspect ratio of height-width is an important parameter for successfully injection molding microchannels. Microfluidic engineers generally prefer tall and thin channels for fluidic functionality, whereas manufacturing engineers generally prefer short and wide channels for ease of manufacturability. When utilizing gravitational force in the direction of fluid flow, a microfluidic engineer can design channels that are shorter and wider to accomplish the fluidic functionality needed for a system, in this case the transfer of bodily fluids. Thus, the utilization of gravity enables complex microfluidic fluid flow in microchannels that are easy to manufacture.

The various embodiments described herein also include valves and channels that further extend the functionality of the open microfluidic platforms being utilized. These valves allow for more complex fluid handling within passive microchannels. For instance, the valves can induce timed fluid release or specific volume releases using the disclosed embodiments. Utilizing these same gravity enhancements with channels oriented in the direction of gravity, channels can be designed to create a droplet, and have the droplet connect to another channel after growing to a specific size. This droplet formation can also allow the connection of the channel to any receptacle, including, but not limited to, centrifuge tubes and other attached reservoirs. The step of creating a droplet further allows specific boluses of fluid to be delivered, as the distance to the channel or surface properties of the plastic change the size of the drop necessary to allow gravity to dominate over surface tension and allow fluid flow. Because the fluid is creating a droplet and falling into the next chamber, that chamber can then be easily removed from the channel for further use. The ability to utilize capillary and gravitational forces together to create efficient channels can result in devices that are simpler, less expensive, and easier to manufacture and more robust in their operation because they have higher working tolerances, therefore not requiring as much precision in the channels. This can result in reduced unit cost. As these channels can overcome larger differences in surface energy than capillary-driven devices, the connections can be more easily made with a variety of less-specialized devices, as in the cases of plastic centrifuge tubes or rubber septum reservoirs. The connection with these parts can be easily severed to allow these parts to be removed from the device and sealed with minimal secondary processes, enabling a bodily fluid reservoir to either be connected with no backflow or disconnected from the device entirely or some combination of those steps.

Finally, flow in capillary networks can be improved by utilizing gravitational forces. Flow in capillary networks can be limited by two factors: the length of the network and the vertical changes in height between areas of the network. As to network length, increases in length result in corresponding decreases in capillary flow rate, due to the resistance to flow developed by the wetted sections of the channel. The reduction in flow rates is particularly difficult for viscous fluids or non-Newtonian fluids which could render the network unusable. By designing a network in a three-dimensional space that flows with the gravitational field, it is possible to counteract the resistance to flow in order to accelerate or maintain at a constant velocity the flow of the fluid in the network.

In the case of capillary networks that have differences in vertical height along the length of the device, the weight of the fluid can cancel the capillary pull force and prevent the flow from occurring. In these instances, there will be a point along the length of the channel at which the fluid front, or leading edge, stops advancing through the channel and which is dependent on the capillary number of the channel, the geometry of the channel, and the composition of the fluid.

Figure 1B:
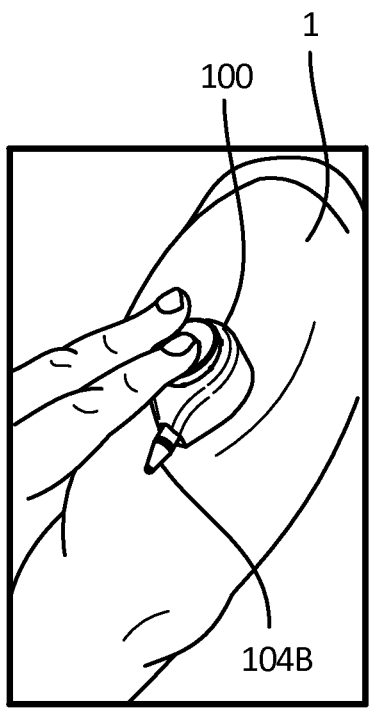
FIG. 1B is a perspective view of the embodiment of FIG. 1A, applied to the skin of a subject.
Figure 1C:
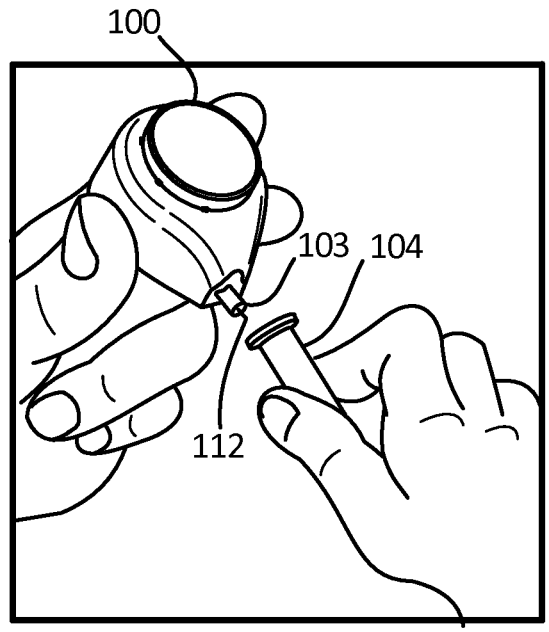
FIG. 1C is a further perspective view of the embodiment of FIG. 1A, wherein the reservoir is being removed.

Turning to the figures with greater detail, FIGS. 1A-1F and 2A-2F depict exemplary embodiments of the gravity-enhanced fluid collection device, or simply "collector" 100. As is shown in FIGS. 1A and 1B, in exemplary embodiments, the collector 100 generally comprises a housing 10 having first 12 and second 14 ends, and which is configured to be in fluidic communication with at least one reservoir 104, such as a tube or cartridge by way of a fitting or coupling portion 103, which is also called a "collar" in certain embodiments, and an outflow channel 112. In exemplary embodiments, the reservoir 104 can be removably attached to the housing 10, by way of the coupling portion 103, such that it may be detached, as is shown in FIG. 1C. In certain embodiments, the reservoir 104 can be a standard Eppendorf tube press-fitted on the fitting 103. In further embodiments, the reservoir 104 can also be custom made and utilize capillary forces or solely gravitational forces to fill. The tube 104 can thus act as a removable and standardized reservoir 104 for containing or gathering the fluid that can be simply and easily detached and inserted into existing and established testing or lab equipment. By way of example, where the fluid is blood, the tube 104 can be easily inserted into clinical and laboratory equipment or workflows for diagnostics and/or biomarker detections.

Figure 2A:
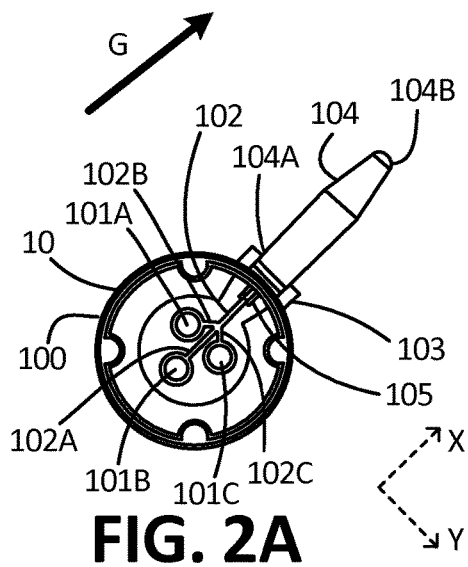
FIG. 2A depicts a top-down cross-sectional view of the collector, according to one embodiment.

In use, as best shown in FIG. 1B, the collector 100 is placed on the skin of a user such that the distal portion 104B of the fluid reservoir 104 is oriented in a substantially vertically down position. As a result of this orientation, bodily fluids collected at the collection sites 101 are drawn in by the fluidic network 102 for transport out the fluid reservoir 104. In these embodiments, as best shown in FIG. 2A, capillary forces allow the fluid to interact and be guided by the individual microfluidic channels 102A, 102B, 102C of the fluidic network 102 which are disposed within the housing to maximize the advantages of the channel geometries, while gravity biases the flow of fluids into and through the fluid network 102. Additional description of the fluidic and physical connection of the reservoir 104 is set forth below in conjunction to FIGS. 3A-3C, 5A-6 and 15A-16E, for example.

Figure 1D:
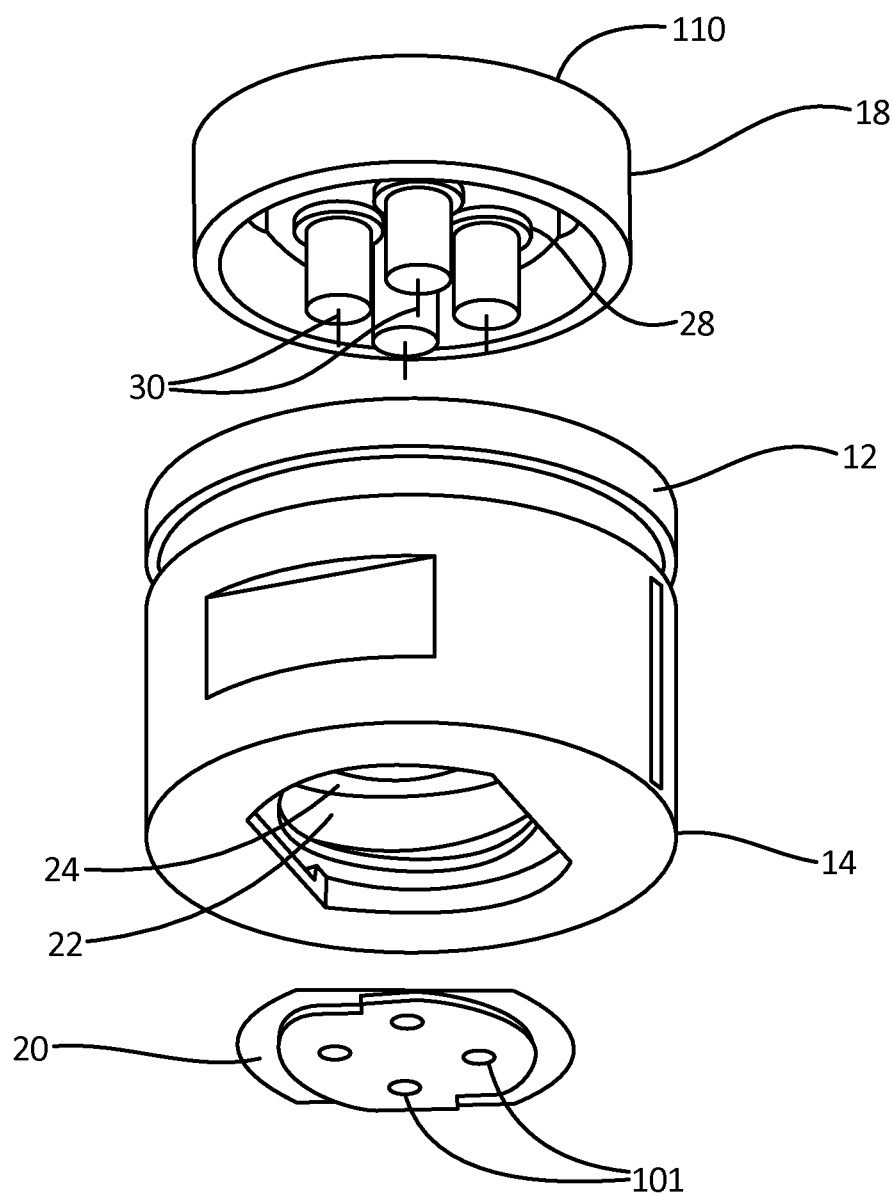
FIG. 1D is an exploded perspective view of one embodiment of the collector showing the base, actuator and lumen.

As is shown in FIG. 1D, in exemplary embodiments, the housing 10 further comprises an internal lumen 22, as has also been previously described in U.S. application Ser. No. 13/750,526, filed Jan. 25, 2013, entitled "Handheld Device for Drawing, Collecting, and Analyzing Bodily Fluid," which is incorporated herein by reference. Further, certain devices have at least one actuator 110, and are configured to be placed against the skin of a patient 1, as is shown in FIG. 1B. Upon depressing or otherwise operating the actuator 110, at least one lancet, needle or other skin puncture device (such as the four needles 30 depicted in FIG. 1D, which is discussed below) is deployed, so as to pierce the subject's skin and cause blood or other bodily fluid to pool near the collection areas (as shown in FIGS. 4A-4D), for uptake into the microfluidic network.

FIG. 1D is an exploded perspective view of an exemplary embodiment of the collector 100, in accordance with one implementation. In this embodiment, the actuator 110 functions as a plunger 18 configured to be inserted into the lumen 22 at the proximal end 12 of the housing 10. This plunger contains a face 28 and a plurality of needles 30 or lancets. The plurality of needles 30 is fixed to the face 28. A base 20 attaches to the distal end 14 of the housing 10 and contains a plurality of apertures, or collection sites 101 that are in fluid communication with the lumen 22 and match with the number and positions of the needles 30 on the plunger 18 such that the needles 30 extend through the apertures 101.

The plurality of needles 30 may include needles having a gauge from 20 gauge to 40 gauge. In some embodiments, the needles are from 29 gauge to 40 gauge. In an alternative embodiment, the plurality of needles 30 may include a plurality of microneedles. In the embodiment shown in FIG. 3, the plurality of collection sites 101 on the base 20 illustratively includes four apertures that match with the needles 30. In alternative embodiments, the plurality of collection sites 101 may include from two to one hundred apertures. The plurality of needles 30 are aligned to be guided to pass through the plurality of collection sites 32 when a user actuates the actuator 110, thereby deploying the needles 30.

In certain embodiments, a spring 24 is provided, which retracts the plunger 18 through the lumen 22 from the distal end 14 to the proximal end 12 of the housing 10 after the plunger 18 has been depressed and the force used to depress the plunger 18 has been removed, thereby removing the plurality of needles 30 from the subject's skin and creating a vacuum in the vacuum creation space 22, which is the portion of the lumen 22 distal to the plunger 18. In these embodiments, the vacuum created in the lumen 22 creates a vacuum at each of the collection sites 101, thereby enhancing the pooling of bodily fluid on the subject's skin, optimizing fluid extraction from each puncture site where one of the plurality of needles 30 penetrates the subject's skin, and at the same time minimizing the size of each puncture site. The vacuum created may range from greater than 0 Pa to 75,000 Pa.

Within the various collector embodiments, a network of microfluidic channels are utilized to shuttle fluid from the various fluid collection sites to the outflow channel. As will be shown with reference to FIGS. 1E and 1F, designing open or closed channels in a collector that utilize a combination of capillary and gravity forces can be accomplished by changing the geometry of the channel or properties of the fluids and device materials. A characteristic number that can be used to design these channels is the Bond number, which is Equation 1:

$$Bo = \Delta \rho g L^2 / \sigma \qquad (1)$$

where $\Delta \rho$ is the difference in fluidic density between the fluid flowing in the channel and the fluid surrounding it, g is the gravitational constant, L is the characteristic length of the channel, typically its width, and $\sigma$ is the surface tension of the fluid.

For Bond numbers lower than 0.1, capillary forces serve as the primary driving forces, and gravity is of lesser influence. At Bond numbers above 10, gravity becomes the primary driving force. For Bond numbers between 0.1 and 10, both capillary and gravitational forces have a definitive effect—that can compete, amplify, or alter one another. For example, if a channel has a negative slope, gravitational forces will amplify the flow and allow the flow to cross defects on the surfaces, grooves, and pinning regions. On the contrary, if the channel has a positive slope gravity will reduce the flow and potentially stabilize the effect of some surface tension features such as pinning valves. Finally, capillary and gravitational forces can be used in conjunction in the design of channels, as described herein, so as to enhance and otherwise direct the flow of a collected fluid. For example, to drive a specific branch of a dividing channel or flow around features that would be in the way of direct gravitational flow by use of capillary features that direct the flow, as is discussed herein. Further, the combination of gravitational and capillary forces can be used to create efficient, cost-effective devices, systems and methods, like those disclosed herein.

Figure 1E:
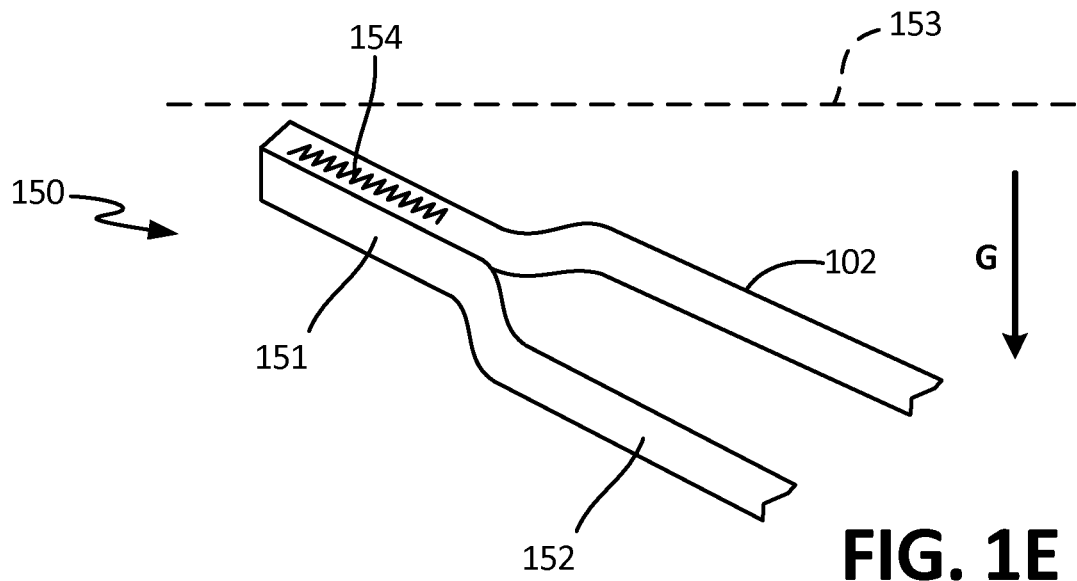
FIG. 1E is perspective schematic of a microfluidic channel of an exemplary embodiment of the collector comprising two regions, a capillary-dominant region and a gravity-dominant region.
Figure 1F:
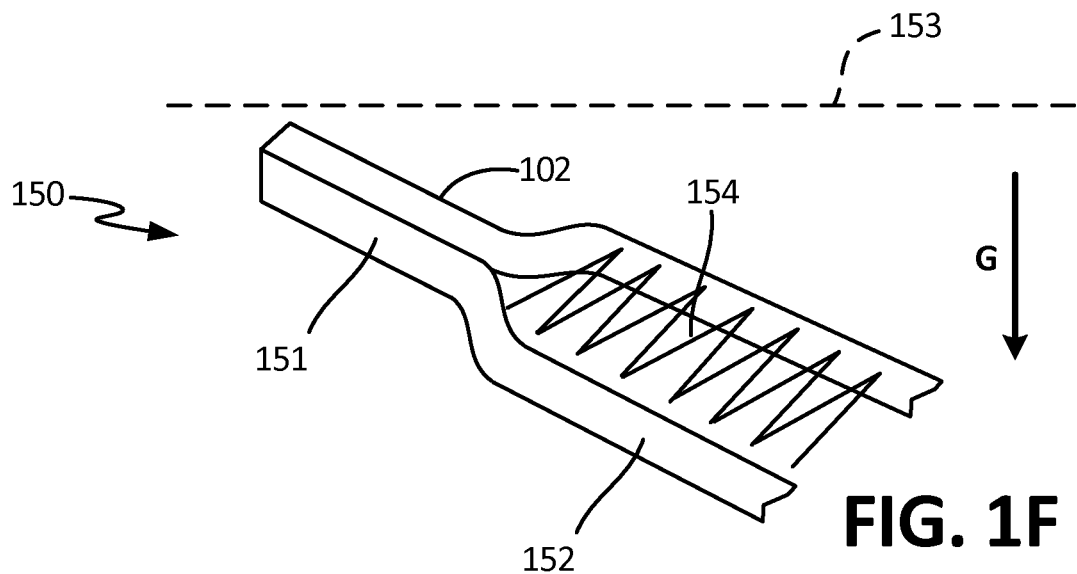
FIG. 1F depicts the embodiment of FIG. 1D, wherein the fluid is in the gravity-dominant region.

These features are exemplified in FIGS. 1E and 1F, in which a channel 150 contains at least two distinct regions. A first, more narrow region of high capillary force 151 (a low Bond number) and a second, wider region 152 where the Bond number is higher, and gravity plays a more substantial role in the fluid flow. Fluid 154 will be readily drawn into the first region 151 due to the high capillary force. Once the fluid reaches the second region 152, given the high Bond number, capillary force is insufficient to drive the flow alone, and gravity is then utilized to cause the flow to continue. To function properly, the channel 150 has to have a negative slope relative to the horizontal 153. Additionally, because less capillary force is being applied, these channels can be designed to retain less fluid. As is described herein, the use of these combinations of forces allows the collector's microfluidic network to achieve fluid flow in a variety of applications.

EXAMPLE 1

Average Blood Travel Distance

Figure 1G:
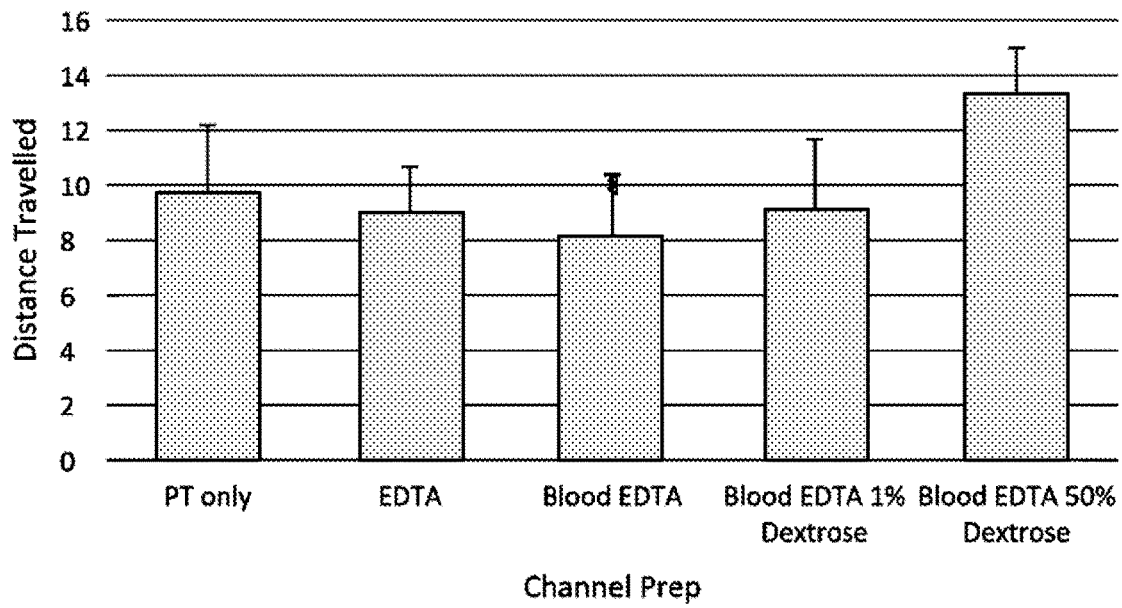
FIG. 1G is the distance traveled by fluid in channels of specific characteristics.
Figure 1H:
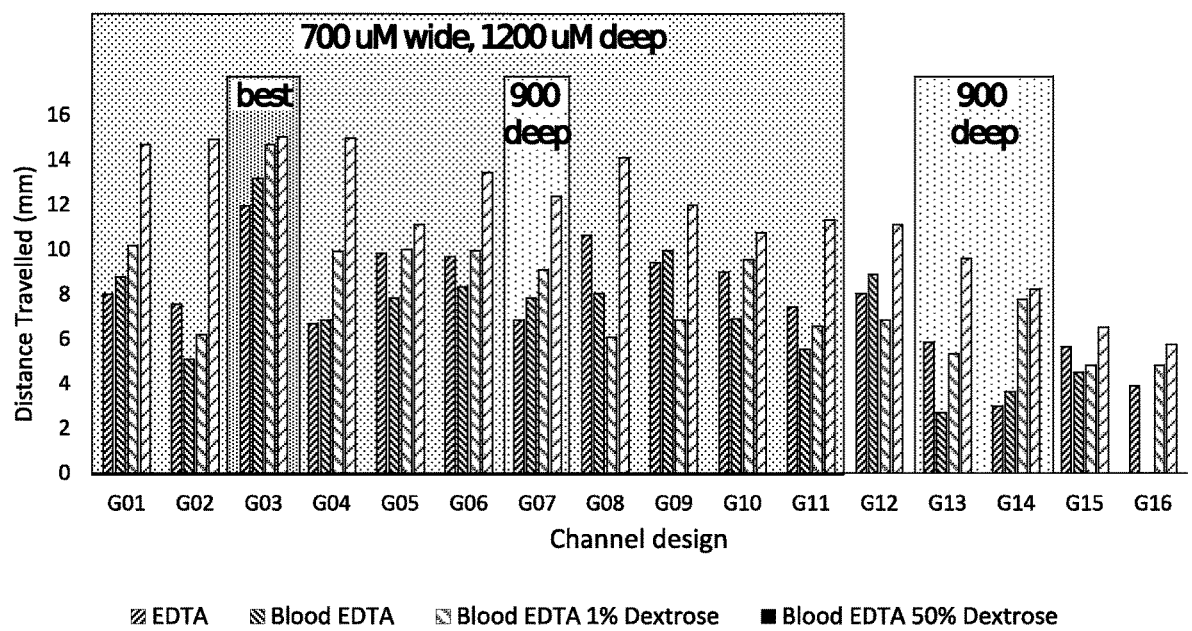
FIG. 1H is the distance traveled by fluid in a variety of channel designs.

FIG. 1G depicts the average blood travel distance for various channels under experimental conditions. To test the travelled distance of fluid in channels with various geometries, ports, and treatments, a channel of 700 um×1200 um was tested with various channel designs to assess the overall travel distance of the fluid. In this figure, * represents $p<0.0001$., with an $n=10$ per condition. Error bars represent standard deviation of the mean. In this example, the channels were designed with an aspect ratio of 700 um wide× 1200 um, and the channels treated with 50% dextrose and 1.8 mg/mL EDTA resulted in optimal capillary draw. In FIG. 1H, the data for various channel geometries is shown.

Figure 2B:
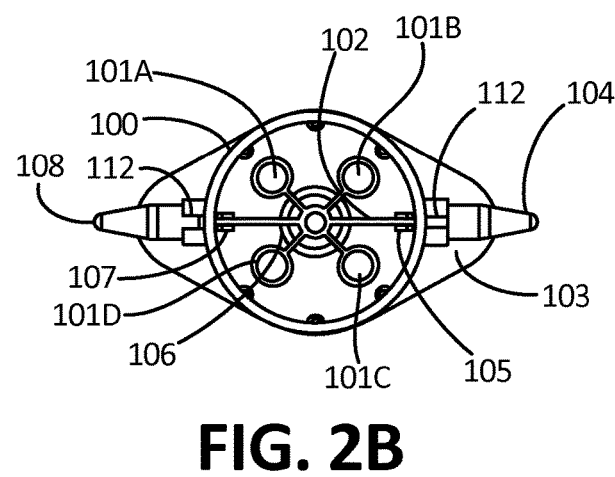
FIG. 2B depicts a top-down cross-sectional view of the collector, according to an alternate embodiment.
Figure 2C:
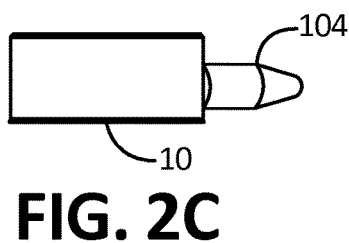
FIG. 2C depicts a side view of the collector, according to an exemplary embodiment.
Figure 2D:
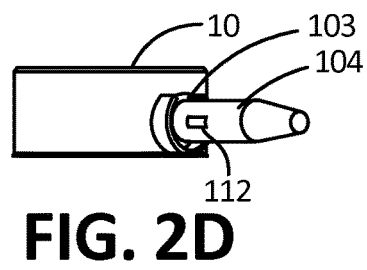
FIG. 2D is a side view of the collector of FIG. 2C from an alternate angle.
Figure 2E:
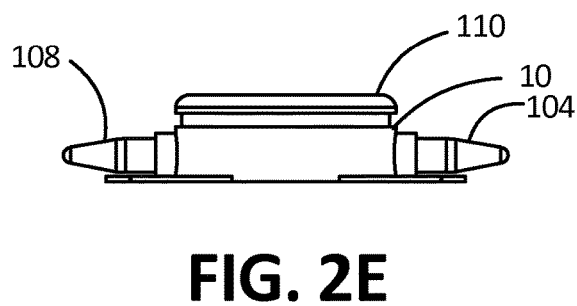
FIG. 2E is a side view of a collector having multiple reservoirs, according to an exemplary embodiment.
Figure 2F:
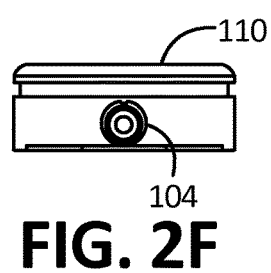
FIG. 2F is a side view of the collector of FIG. 2E from an alternate angle.

FIGS. 2A and 2B, depict top-down, cross-sectional views of the internal components of two exemplary embodiments of a collector 100. In these embodiments, networks of microfluidic channels 102 utilizing both capillary forces and gravity forces can be used to shuttle the blood down small scale channels (typically defined by a capillary number of less than 0.1) and larger channels respectively. In such small channels, the capillary forces are the primary driving forces of fluid movement.

In such embodiments, and as best shown in FIGS. 2A and 2B, the collector 100 comprises at least one collection site 101A, 101B, 101C, 101D disposed within the housing 10, a fluidic channel network 102, such as a microfluidic channel network 102, a coupling portion 103, an outflow channel 112 and at least one reservoir 104. Various implementations will feature a variety of numbers and configurations of collection sites, such as the three sites 101A, 101B, 101C shown in FIG. 2A or four sites 101A, 101B, 101C, 101D shown in FIG. 2B. Other configurations are possible. In various embodiments, as best shown in FIG. 2A, the reservoir 104 further comprises proximal 104A and distal 104B ends.

Certain embodiments further comprise at least one ramp 105, the microfluidic channel geometry which can be defined so as to exploit the maximum vertical height attainable, thereby facilitating the constant flow of fluids through various changes in height. Specific channel geometries can be designed to facilitate fluid flow by the combination of capillary and gravitational forces.

A more detailed explanation of the configurations and benefits of such ramps 105 follows. As open microfluidic channels contain open liquid-air interfaces, spontaneous capillary flow can be utilized in certain settings to drive fluid flow. The use of capillary-driven flow to manipulate fluids in complex open microfluidic networks is a novel feature previously unused in open microfluidic channels. In order to insure that spontaneous capillary flow ("SCF") occur in a channel containing any number of open liquid-air interfaces in its cross-section, an analysis of capillary force was developed, to define a design guideline ensuring that the capillary force provided by the walls of the microfluidic channel overcomes the resistance created by the open sections of the microfluidic channel.

The result of the analysis is written in a SCF relation stating that the ratio of the free perimeter ($p_f$), defined by the length of the cross-section open to air or another medium, and the wetted perimeter ($p_w$), defined by the length of the cross-section made up of solid hydrophilic material must be less than the cosine of the contact angle ($\theta$) of the fluid with the channel walls. The SCF relation can be written as:

$$p_f/ p_w < cos(\theta^*) \qquad (2)$$

Figure 6A:
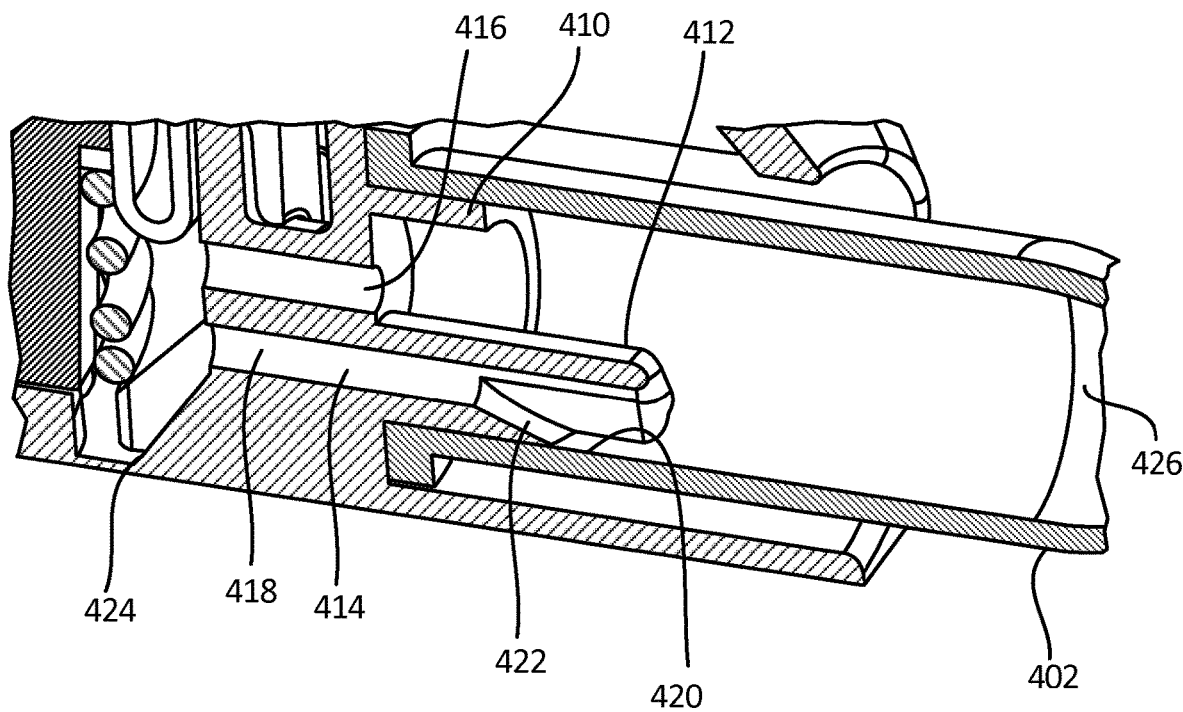
FIG. 6A is a detailed perspective cross-sectional view of an outflow channel and reservoir, according to an exemplary embodiment.
Figure 6B:
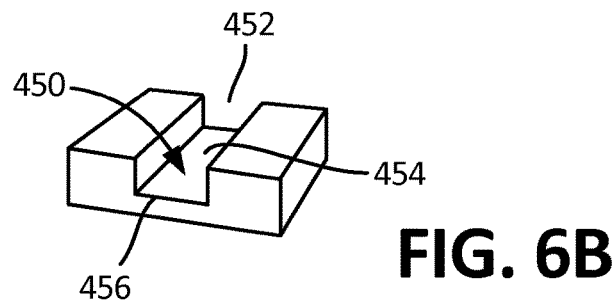
FIG. 6B is a perspective view of an open microfluidic channel which satisfies the SCF relationship and can serve as a ramp in certain embodiments.
Figure 6C:
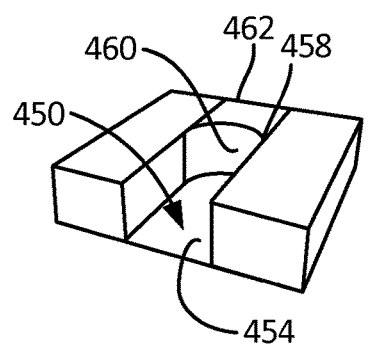
FIG. 6C is a perspective view of the channel of FIG. 6B, further comprising fluid.

Equation (2) thus defines the set of open channel geometries under which the SCF relation is met. When the SCF relation is satisfied, the channel will drive the flow through the microfluidic network by capillary forces, including against the force of gravity. Importantly, the SCF relation extends to most channel configurations containing open liquid-air and wetted sections. Further, the open liquid-air sections do not have to be continuous or contiguous. Thus the SCF relation still holds for complex channel geometries containing open "windows" on the channel (e.g., a circular aperture in the wall of a channel) as well channels containing multiple open liquid-air interfaces at the same point in the channel (e.g., a fluid completely suspended between two rails in a channel devoid of ceiling and floor). Open microfluidic channels verifying the SCF relation also have the benefit of not being constrained to rectangular cross-sections. FIGS. 6B and 6C depict further views of these applications.

With that background in mind, a ramp (such as ramp 105) can be used to exploit the maximum vertical height attainable. The vertical height change that a fluid can reach can be evaluated experimentally and analytically using an equation relating to the force of gravitational resistance ($F=\rho g \Delta h$) and the estimation of the force of capillary pull ($F=2\gamma \cos(\theta^*)/R_F$, where $\theta^*$ is the equivalent contact angle of the fluid in an open microfluidic channel, and $R_F$ is the fluidic radius of the channel. $\theta^*$ is defined as $\cos(\theta^*)=\Sigma f_i \cos(\theta_i)$, where $f_i$ represent the relative length of a section of the channel wall that has a contact angle $\theta_i$. $R_F$ represents the fluidic radius of the channel and is defined as $R_F=2A/P$, where A is the cross-sectional area of the channel and P the perimeter of the channel). These two forces allow the estimation of the maximum vertical height attainable by the fluid, as given in Equation 3:

$$\Delta h = \frac{\gamma \cos(\theta^*) P}{\rho g A} \qquad (3)$$

By way of example, in the case of a rectangular channel of 1 mm width, 1 mm depth and open on the ceiling, with a contact angle of 60 degrees on the plastic surfaces and assumed to be 90 degrees in the open interface areas, filled with water, the maximum vertical height attainable is evaluated to be about 10.5 mm. Further data can be seen in Table 1.

Utilizing the knowledge of the maximum vertical height for various channel geometries, the disclosed collector embodiments can comprise microfluidic networks with

TABLE 1

Maximum Vertical Height Attainable for Various Channel Geometries

| | | Height (in meters) | | | | | | |
|---|---|---|---|---|---|---|---|---|
| | | 0.0001 | 0.0002 | 0.0003 | 0.0004 | 0.0005 | 0.0006 | 0.0007 |
| Width (in meters) | 0.0001 | 107.1429 | 89.28571 | 83.33333 | 80.35714 | 78.57143 | 77.38095 | 76.53061 |
| | 0.0002 | 71.42857 | 53.57143 | 47.61905 | 44.64286 | 42.85714 | 41.66667 | 40.81633 |
| | 0.0003 | 59.52381 | 41.66667 | 35.71429 | 32.7381 | 30.95238 | 29.7619 | 28.91156 |
| | 0.0004 | 53.57143 | 35.71429 | 29.7619 | 26.78571 | 25 | 23.80952 | 22.95918 |
| | 0.0005 | 50 | 32.14286 | 26.19048 | 23.21429 | 21.42857 | 20.2381 | 19.38776 |
| | 0.0006 | 47.61905 | 29.7619 | 23.80952 | 20.83333 | 19.04762 | 17.85714 | 17.0068 |
| | 0.0007 | 45.91837 | 28.06122 | 22.10884 | 19.13265 | 17.34694 | 16.15646 | 15.30612 |
| | 0.0008 | 44.64286 | 26.78571 | 20.83333 | 17.85714 | 16.07143 | 14.88095 | 14.03061 |
| | 0.0009 | 43.65079 | 25.79365 | 19.84127 | 16.86508 | 15.07937 | 13.88889 | 13.03855 |
| | 0.001 | 42.85714 | 25 | 19.04762 | 16.07143 | 14.28571 | 13.09524 | 12.2449 |
| | 0.0011 | 42.20779 | 24.35065 | 18.39827 | 15.42208 | 13.63636 | 12.44589 | 11.59555 |
| | 0.0012 | 41.66667 | 23.80952 | 17.85714 | 14.88095 | 13.09524 | 11.90476 | 11.05442 |
| | 0.0013 | 41.20879 | 23.35165 | 17.39927 | 14.42308 | 12.63736 | 11.44689 | 10.59655 |
| | 0.0014 | 40.81633 | 22.95918 | 17.0068 | 14.03061 | 12.2449 | 11.05442 | 10.20408 |
| | 0.0015 | 40.47619 | 22.61905 | 16.66667 | 13.69048 | 11.90476 | 10.71429 | 9.863946 |

| | | Height (in meters) | | | | | | |
|---|---|---|---|---|---|---|---|---|
| | | 0.0008 | 0.0009 | 0.001 | 0.0011 | 0.0012 | 0.0013 | 0.0014 | 0.0015 |
| Width (in meters) | 0.0001 | 75.89286 | 75.39683 | 75 | 74.67532 | 74.40476 | 74.17582 | 73.97959 | 73.80952 |
| | 0.0002 | 40.17857 | 39.68254 | 39.28571 | 38.96104 | 38.69048 | 38.46154 | 38.26531 | 38.09524 |
| | 0.0003 | 28.27381 | 27.77778 | 27.38095 | 27.05628 | 26.78571 | 26.55678 | 26.36054 | 26.19048 |
| | 0.0004 | 22.32143 | 21.8254 | 21.42857 | 21.1039 | 20.83333 | 20.6044 | 20.40816 | 20.2381 |
| | 0.0005 | 18.75 | 18.25397 | 17.85714 | 17.53247 | 17.2619 | 17.03297 | 16.83673 | 16.66667 |
| | 0.0006 | 16.36905 | 15.87302 | 15.47619 | 15.15152 | 14.88095 | 14.65201 | 14.45578 | 14.28571 |
| | 0.0007 | 14.66837 | 14.17234 | 13.77551 | 13.45083 | 13.18027 | 12.95133 | 12.7551 | 12.58503 |
| | 0.0008 | 13.39286 | 12.89683 | 12.5 | 12.17532 | 11.90476 | 11.67582 | 11.47959 | 11.30952 |
| | 0.0009 | 12.40079 | 11.90476 | 11.50794 | 11.18326 | 10.9127 | 10.68376 | 10.48753 | 10.31746 |
| | 0.001 | 11.60714 | 11.11111 | 10.71429 | 10.38961 | 10.11905 | 9.89011 | 9.693878 | 9.52381 |
| | 0.0011 | 10.95779 | 10.46176 | 10.06494 | 9.74026 | 9.469697 | 9.240759 | 9.044527 | 8.874459 |
| | 0.0012 | 10.41667 | 9.920635 | 9.52381 | 9.199134 | 8.928571 | 8.699634 | 8.503401 | 8.333333 |
| | 0.0013 | 9.958791 | 9.462759 | 9.065934 | 8.741259 | 8.470696 | 8.241758 | 8.045526 | 7.875458 |
| | 0.0014 | 9.566327 | 9.070295 | 8.673469 | 8.348794 | 8.078231 | 7.849294 | 7.653061 | 7.482993 |
| | 0.0015 | 9.22619 | 8.730159 | 8.333333 | 8.008658 | 7.738095 | 7.509158 | 7.312925 | 7.142857 |

As shown in Table 1, various channel geometries can be contemplated for a given material contact angle (here assumed to be 60 degrees) that contemplate the theoretical maximum vertical height attainable by the fluid, as given in Equation 3. Due to open channel geometry, increases to the width of the channel will affect fluid travel against gravity more than increases to the height. Table 1 depicts the net vertical height (in millimeter) a fluid can travel against gravity. While the distance traveled may vary depending on the orientation of the channel relative to the direction of gravity, the total height achieved will remain the same. The calculated values are the theoretical total height a fluid can travel directly against gravity, thus, as a channel is placed at an angle not directly against gravity, the fluid will be able to travel a greater length along the channel that will not exceed the total theoretical height. In practice, one trained in the art can utilize the theoretical maximum height traveled to engineer fluidic microsystems that contemplate the combination of capillary and gravitational forces.

These numbers are well correlated with experimental data collected on such channels. However, regardless of the geometry of the channel, a point of maximum vertical height that a fluid can reach will always exist. The maximum vertical height attainable can increase as the channel is held in various angles that are less than directly opposite to gravity.

channels designed to facilitate the collection and movement of fluids by a combination of capillary and gravitational forces in a variety of implementations. Additionally, the contact angle can be modified by different treatments of the surface through plasma, chemical, or physical additives. Additives to the channel to improve capillary drive can include EDTA, heparin, dextrose, and other additives that when dried pull fluid up and into the channel. The percentage of dextrose tested showed improved blood pulling capabilities with 50% dextrose dried into the channel.

When utilizing gravity to direct fluid flow, more unique channel geometries can be utilized. Therefore filling standardized reservoirs, such as centrifuge tubes or rubber septum reservoirs is easily accomplished. Fluid can also be made to fill larger reservoirs which typically have a low capillary number and thus more sensitive to gravity. Enhancing the flow of blood using gravity also ensures reliability in fluidic connections, at the specific location for example when the fluid must be transferred from the collection device to a detachable reservoir. Typically the small gap that exists at these connection points can act as barriers blocking the advancement of the fluid. With the addition of gravity and well-designed channel geometries these gaps can be cleared reliably. Thus, there is no need to engineer and manufacture specialized outflow channels and/or reservoirs that have a short channel length in order to satisfy the fluid flow requirements imposed by a gravitationally independent microfluidic system. As is shown further in FIGS. 3A-3C and 6, these ramps can assist with the movement of fluid from a collection site up and out to the outflow channel.

Returning to FIG. 2A, by utilizing gravitational force as a means of shuttling the fluid, various embodiments can ensure that blood flowing down one of the branches 102A, 102B, 102C of the microfluidic network 102 do not substantially enter the other branches, because, in use, the branches 102A, 102B, 102C are configured to be oriented from the collection sites 101 to the coupling region 103 such that the direction of flow is substantially in line with the direction of gravity (designated with the reference arrow G). By way of example, in certain implementations, the flow can occur between −60 and +60 degrees from the direction of gravity when rotated about the z (normal to the bottom surface) axis. When rotated about the y (along the face of the bottom surface, perpendicular to the direction of gravity in this case) axis, a rotation comprised between +90 and −45 degrees was observed to be functional (FIG. 1A also depicts the axis for reference). However, embodiments can be contemplated wherein any direction vector that has a positive component in the direction of gravity will enable flow.

In various embodiments, the flow will be proportional to the angle made by the microfluidic channel relative to the direction of the gravitational force. In this manner, the gravity-enhanced microfluidic networks are able to minimize the volume of sample lost passively through backwashing or other non-productive flows in the channels. Further, utilizing gravity-enhanced microchannels, it is possible to empty the channels at the end of the fluid collection and further reduce lost volumes of fluid that may remain within the fluidic network. In these embodiments, once the source of fluid—such as blood flowing from a lancet puncture on the skin—stops providing additional fluid, the channel will simply drain into the tube connected to the channel network. This effect can be maximized by designing a channel that expands as it reaches the reservoir so that capillary action becomes weaker as the fluid reaches the reservoir. Using this approach, gravity will become the primary force, gradually overcoming the capillary forces and thereby minimizing the amount of fluid remaining in the microfluidic channel following outflow.

As shown in FIG. 2B, in alternate embodiments, the microfluidic network can be connected to two or more tubes or reservoirs 104, 108. In this specific example, the reservoirs 104, 108 are positioned on alternate sides of the collector 100. Utilizing this approach, the device 100 can allow the collection of fluid in one of the reservoirs 104, 108 even in the event that the user places the device 100 in the wrong direction. The device 100 is similarly placed on the skin of the user in any vertical direction. The bodily fluid pooling at the surface of the skin in the collection sites 101 is captured by the fluidic channel network and, depending on the orientation of the device 100, gravity will bias its flow down the most descending channel. In one embodiment, there are two channels 102 and 106, or alternatively there can be any number of channels if more degrees of freedom on the placement of the device 100 are desired. As the fluid flows through the channel (102 or 106), it will be raised from the plane of the channel network into the reservoirs by fluidic ramps 105 or 107, as is described further below in relation to FIGS. 3A-3C and 5A-6. Reservoirs 104 and 108 are connected on each end and the reservoir (104 or 108) located lower vertically will become the reservoir receiving the fluid. In other embodiments, any number of reservoirs can be designed. In yet other embodiments, these reservoirs can be standardized Eppendorf tubes press fitted onto the device 100 by a fitting 103. Importantly, as the fluid does not enter or minimally enters channels that go in an ascending direction, the addition of these channels does not incur a loss of fluid. Further, in certain embodiments in which the capillary number is low, the fluid will be drained from the channels into the reservoirs at the end of the fluid collection or fluid flow, minimizing the loss of fluid in the reservoirs. FIGS. 2C-2F depict various exterior side views of the embodiments of FIGS. 2A and 2B, including the various shapes of the actuator 110 and the orientation of one or more tubes or reservoirs 104, 108.

Figure 3A:
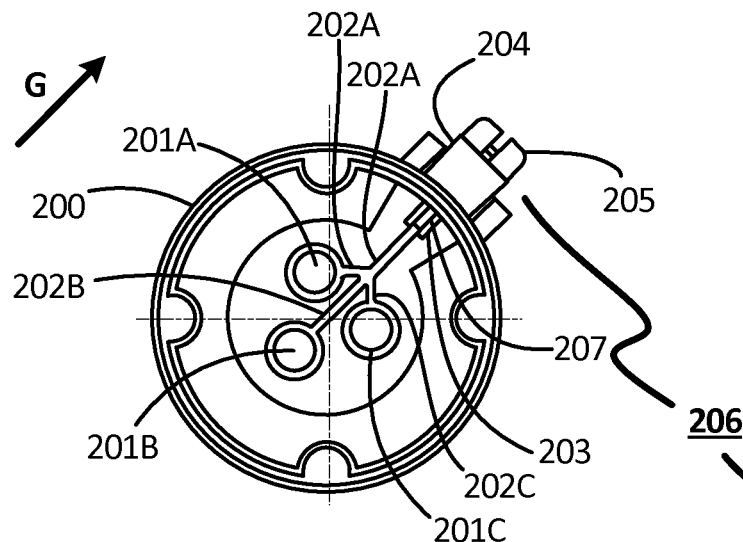
FIG. 3A is a top-down cross-sectional view of the collector, according to one embodiment.

As shown in FIGS. 3A-3C, in certain embodiments, the collector 200 is configured such that fluid is collected in a detachable tube or reservoir (as shown in FIG. 1C, for example) or standardized tube using a U-shaped, suspended, or outflow channel 205 that extends into the center of the tube (such as tube 104 of FIGS. 1A-1C) as part of a tube connection 206 and can be elevated from the initial collection site by a channel 207 which serves as a ramp 207 (as best shown in FIGS. 3B and 3C). By using open microfluidic system ramps 207 for fluids, the various embodiments of the collector 200 can be configured so as to raise or lower the channel plane to any level (as can be seen, for example, in reference to 422 in FIG. 6), such that the relative height of the fluid flow can be changed without reducing or stopping the fluid flow. These movements of fluid in a vertical direction (up or down) can also contribute to the enhancement of the fluid flow. Accordingly, the fluid can be directed through the outflow channel 205 and into a reservoir or tube (such as tube 104 of FIGS. 1A-1C).

In operation, the collector 200 is placed on the skin of the user (such as shown in FIG. 1B with respect to another collector embodiment). As described, blood being collected at one or multiple collection sites 201A, 201B, 201C are captured in a fluidic channel network 202, which comprises a plurality of branched channels 202A, 202B, 202C which are disposed so as to utilize both capillary and gravitational forces when the outflow channel is oriented in the direction of gravity G. When the fluidic channel network is placed in a descending manner, gravity will enhance the flow of fluids down the channels 202A, 202B, 202C. As discussed above, in certain embodiments, a ramp 207 can be used to connect the fluids flowing in the network to the outflow channel 205, which allows the filling of a reservoir (not shown). As with the embodiment shown in FIG. 1C, the reservoir (not shown) used with the connector 200 can be a detachable reservoir that can be removably connected to the device 200. In the example of a standard test tube, the fitting can be a simple press fitting region 204 to which a standard tube is reversibly coupled to create a fluidic seal. In exemplary embodiments, these fittings may be twist or snap fittings, as would be apparent to one of skill in the art. The fitting 206 is sealed to the reservoir, such that the connecting fluidic channel or outflow channel 205 spans into the reservoir (as shown in FIG. 6), thereby allowing the fluid flowing into it to touch a wall or other feature of the reservoir. This serves as a fluidic bridge (which is also called a "capillary bridge") which allows the fluid to transfer into the reservoir, as is described for example in relation to FIGS. 9A-9D and 15A-16E.

The collector 200 is thus able to collect fluid from a site on the subject's skin and shuttle it to the outflow channel 205 using a combination of capillary and gravitational forces. As a second aspect, once the fluid reaches the distal outflow channel 205, it is preferable to have it flow into the reservoir (not shown) as efficiently as possible. As is shown variously in the figures, in certain embodiments the outflow channel can extend the length of the tube/reservoir such that the flowing fluid is able to contact the internal distal end of the tube or reservoir (as is shown in FIGS. 9A-9D at 905 and discussed below). In further embodiments, the outflow channel extends partially into the tube, thereby allowing the collected fluid to contact a side of the tube and descend to the distal end (as is described further below in relation to FIGS. 15A-16E). Accordingly, the outflow channel can be placed at any height relative to a longitudinal plane of the tube or reservoir, thereby allowing the contact of the fluid at any location in the tube, as is desired by the user based on the specific application. Further, gravity can be used to enhance the ability of fluids flowing down the outflow channel to interact and contact the reservoir or tube. In certain embodiments, an extended microfluidic outflow channel allows for a preferable connection with a wall or floor of the reservoir or tube by creating a simple fluidic bridge which allows reliable flow of fluid into the reservoir. In these embodiments, gravity can be used to simply induce a positive curvature of the fluid in the outflow channel such that the fluid bridges to the reservoir and can contact a feature even in the presence of an air gap between the outflow channel and the wall of the reservoir. Gravity can thus also be utilized to create a drop of fluid that will only contact the walls of the reservoir of the tube when a sufficient volume drop has been reached. Further embodiments are described in relation to FIGS. 9A-9D and 16A-16E.

Figure 3D:
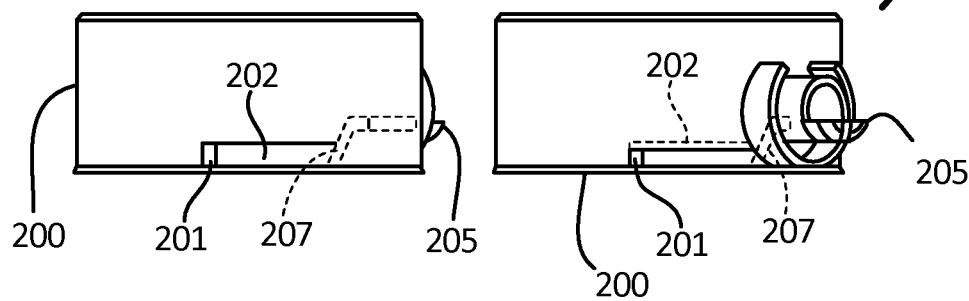
FIG. 3D is a side view of a reservoir and outflow channel depicting a fluidic bridge, according to an exemplary embodiment.
Figure 3D:
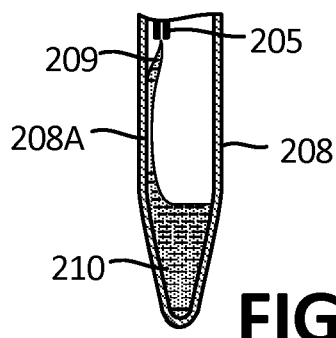

As is shown, for example, in FIG. 3D, in certain embodiments a fluidic bridge 209 is established between the outflow channel 205 and the reservoir 208, thereby forming a fluidic bridge 209 and enabling a continuous flow of the fluid 210 into the reservoir along the inner wall 208A of the reservoir 208. Further, this embodiment can be utilized as a conditional valve for preventing the reverse flow out of the reservoir once the fluid has been collected and the device is placed in a different orientation, as is shown in FIGS. 9A-9D. When placed in an orientation where the reservoir or tube is located at the lowest point, the fluid flows into the reservoir and fills it. After the flow has stopped and the device is placed on a horizontal surface, such as a laboratory benchtop or a desk, the fluid may move to fill the tube sideways. Provided less than a determined volume of fluid was collected in the tube, the level of the fluid will not reach the channel in this orientation and thus prevent any backflow into the device. Further embodiments are described in FIGS. 15A-15C and 16A-16E.

FIGS. 4A-4D depict further embodiments of the collector 300, wherein the microfluidic channel networks 302 are configured to utilize both capillarity and gravity to perform essential fluidic functions. In these embodiments, the collector 300 is configured to collect fluids from the various collection areas 301A, 301B, 301C, 301D and to shuttle the fluid through one or more microfluidic channels 302A, 302B, 302C, 302E, 302F, 302G, 302H to a connection 303A, 303B to a reservoir or analytical device (not shown). In these embodiments, at least one of the channels 302A, 302B is placed in a descending orientation (as described previously in relation to FIG. 2A), and multiple channels 302 can be used to increase the probability and/or ensure that at least one of the channels 302 is in such a descending orientation.

Figure 4A:
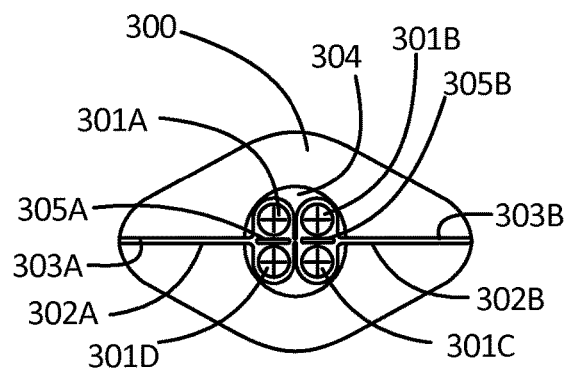
FIG. 4A depicts a top-down cross-sectional view of the collector, according to one embodiment.

As is shown in FIG. 4A, fluids collected in a large open area 304 or fluids flowing down from another collection area 301 and reaching a large opening 304 can be guided using a capillary ridge 305 in the direction of a channel 302. Capillary forces (in the form of Concus-Finn effects for example) on a wedge and angle of the ridge or ridges 305A, 305B will promote the liquid in the form of drops or a continuous flow to remain close to the ridge, or ridges 305A, 305B, as would be apparent to one of skill in the art. In these embodiments, gravity will promote motion of the droplets or slow continuous flow of fluid downwards until it reaches the opening of a channel 302A, 302B. In such embodiments, the ridge is configured to facilitate continuous fluid flow due to the capillary forces created. In various similar embodiments, there is a geometric shape or a sufficiently low surface energy introduced such that the shape drives the capillary action whereby the capillary forces are a principle driving force underlying fluid flow.

Figure 4B:
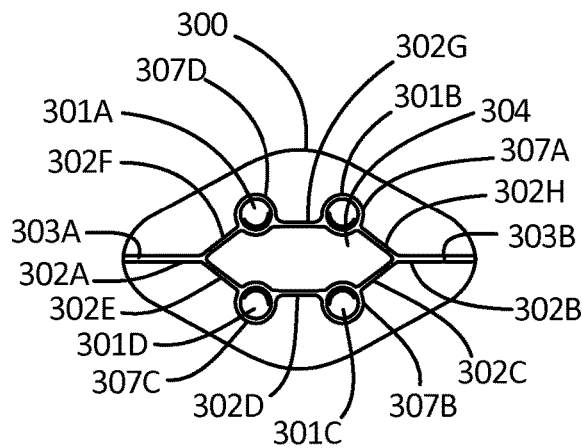
FIG. 4B depicts a top-down cross-sectional view of the collector, according to an alternate embodiment.

In the embodiment of FIG. 4B, various inner channels 302C, 302D, 302E, 302G can connect fluid from one or more fluid collection sites 301A, 301B, 301C, 301D such that fluid from a first collection site 301A will flow downstream through a channel 302G to reach a second collection site 301B. Further, the fluid can be directed around the collection site utilizing capillary forces and gravity by designing a wedge 307A that links a first collection site 301B with the channel 302B opposite a second collection site 302H. These wedges 307A, 307B, 307C, 307D surround the fluid collection sites 301A, 301B, 301C, 301D and allows the fluid to link into the channel by wedge fluid flow. In exemplary embodiments, the wedges are recessed plastic wedges around the collection sites 301A, 301B, 301C, 301D, which are therefore sent into the luminal side of the base 20 on the distal end 14 of the housing 10, as shown in FIG. 1D and would be apparent to one of skill in the art. Accordingly, provided that the fluidic path is consistently and substantially in line with gravity, fluid inputted from each "higher" collection site can be transferred around the lower collection site in a controlled, robust, and clean way. This method prevents needless flow of a previously collected bodily fluid over an exposed skin area for example.

Figure 4C:
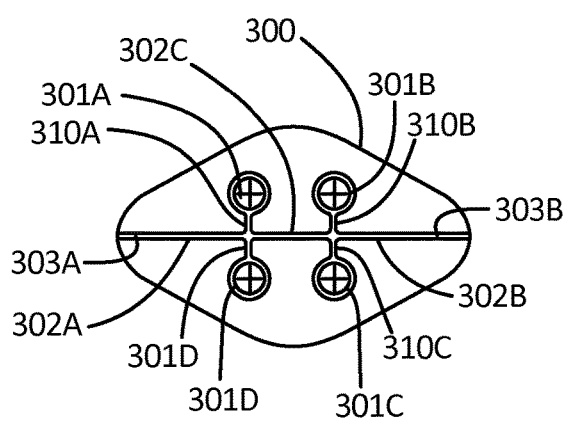
FIG. 4C depicts a top-down cross-sectional view of the collector, according to an alternate embodiment.

In another exemplary embodiment shown in FIG. 4C, fluid collected from each collection site 301A, 301B, 301C, 301D can be transferred through channels such as open microfluidic channels 310A, 310B, 310C, 310D in which capillary force dominates into channels 302A, 302B, 302C that are biased by gravity. In this example, as the fluid in each open microfluidic channel 310 reaches gravity channel 302, it will flow in the descending direction, or direction of lower potential energy, as described in relation to FIGS. 1E and 1F, for example. This system allows the minimization of the overall number of channels required as all collection sites feed into a common channel that can be used bi-directionally.

Figure 4D:
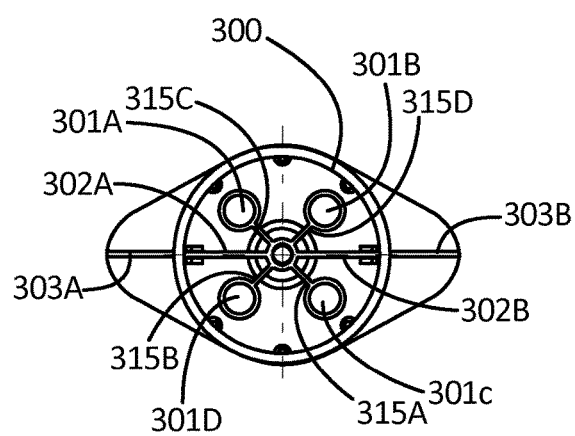
FIG. 4D depicts a top-down cross-sectional view of the collector, according to an alternate embodiment.

In yet a further embodiment, and as shown in FIG. 4D, the capillary channels 315A, 315B, 315C, 315D transferring bodily fluids from the collection sites 301A, 301B, 301C, 301D can be placed in any direction because they are dominated by capillary forces, and once they reach a main channel 302A, 302B, gravity will bias their flow in the descending direction toward the lower outflow channel 303A, 303B. This allows for flexibility over where the fluid is delivered between the collection sites 301A, 301B, 301C, 301D and the main fluidic network 302A, 302B. Importantly, Concuss-Finn effects in the wedges of the main channel can be utilized to promote the extraction of fluids from the capillaries 315A, 315B, 315C, 315D. At the point of contact between the capillary channels 315A, 315B, 315C, 315D and the main channels 302A, 302B the use of a rounded junction and/or sufficiently low surface energy of the material will allow fluid to robustly flow out of the capillary channels 315A, 315B, 315C, 315D, into the main channels 302A, 302B, where the flow of the fluid will be enhanced by gravity.

Figure 5A:
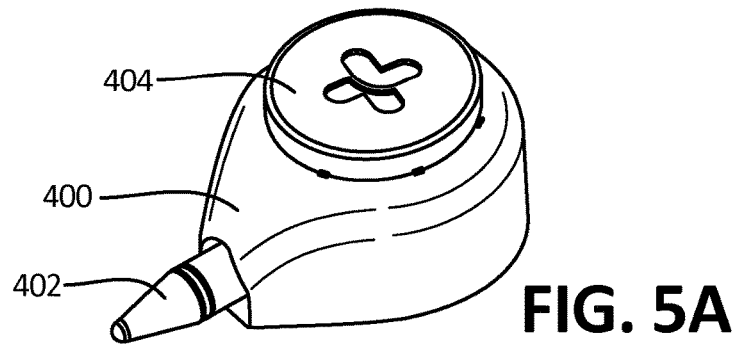
FIG. 5A is a perspective view of the collector, according to an exemplary embodiment.
Figure 5B:
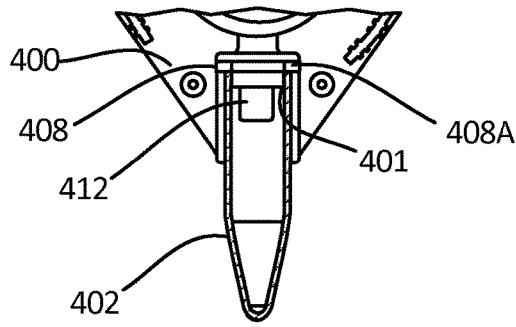
FIG. 5B depicts a top-down cross-sectional view of the collector of FIG. 5A, showing fitting and reservoir connection.
Figure 5C:
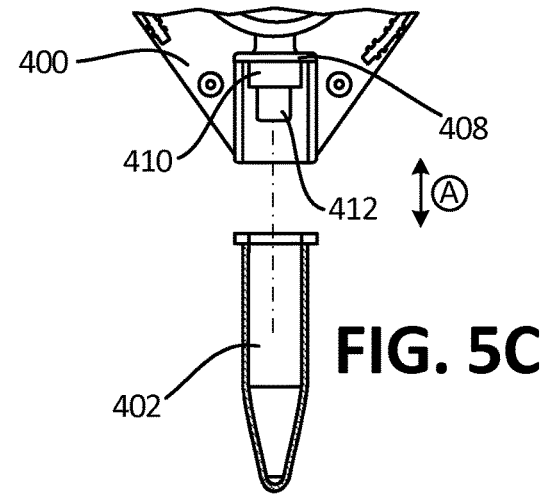
FIG. 5C depicts a top-down cross-sectional view of the collector of FIG. 5A, showing fitting and reservoir connection, wherein the reservoir is removed.

The various embodiments depicted in FIGS. 5A-6 demonstrate a further integrated blood collection and containment device, or collector 400. In various embodiments, the collector 400 features at least one closed-open or one open-closed-open microfluidic system configured to promote the flow of fluid from the internal microfluidic channel network (described in relation to FIGS. 1A-4) into a detachable reservoir 402. One aspect is a detachable reservoir 402 which is capable of being separated from the integrated collection device 400 for seamless integration into existing laboratory processing methods and processes, as it may be easily fitted to coupling region 408 and/or the skirt 410 of the device 400 and later removed, as is shown in FIG. 5C at reference arrow A. In these embodiments, the tube or reservoir 402 is coupled to the device 400 at the collar or plastic skirt 410 which creates a fluidic and/or air-tight seal with the inner surface 401 of the reservoir 402. The inner surface 401 is correspondingly in fluidic and physical communication with an outflow channel 414 contained within an outflow channel housing 412 (as described at surface 420 in relation to FIG. 6) such that fluid collected by the device flows through the microfluidic channel network(s) as a fluidic bridge into the reservoir 402 for collection by way of capillary and gravitational forces. Further embodiments of the fluidic bridge and outflow channel are discussed in relation to FIGS. 3D and 15A-16E.

In particular embodiments, the collector 400 functions by being placed on the skin of the user or subject (similarly to the steps of the embodiment described above and depicted in FIGS. 1A-1C) with the reservoir 402 directed downwards (relative to gravity) and depressing the actuator 404. In various embodiments, the device 400 and reservoir 402 may comprise a hermetic or fluidic seal 401, and the actuation of the button 404 may cause the pressure in the device 400 and reservoir 402 to decrease, thus enhancing the blood flow out of the skin of the user. Gravity and capillary force then guide blood into the reservoir 402, as was previously described. In certain phases, the driving force behind the fluid draw can be caused by microfluidics and/or pressure differential. By way of example, in certain implementations the pressure differential can be the primary force in drawing fluid out of the skin into the channels, while the microfluidic forces account for the movement of blood through the channel or network.

Specifically, being able to transfer the collected bodily fluid sample from an integrated microfluidic collector 400 into a reservoir 402 or other collection reservoir that is easily detachable from the device is novel in the field of capillary blood collection. The bodily fluid collected from the patient is transferred through an outflow channel 414 into the reservoir 402. At the end of use or when the desired volume of blood is collected in the reservoir 402, it can simply be detached by pulling it off by several known methods, such as a press-fitting or twisting it off of a threaded structure 408A which is defined on the fitting 408.

The fluidic connection allowing robust transfer of the bodily fluid between the device 400 and the reservoir 402 is created through the outflow channel 414. The outflow channel 414 is capable of being inserted into the tube, which is correspondingly sealed around the plastic skirt 410. Accordingly, in exemplary embodiments, the microfluidic outflow channel 414 is comprised of the first open microfluidic channel 424 in fluidic communication with the internal microfluidic channel network described in relation to FIGS. 1A-4C. In these embodiments, the first open microfluidic channel 424 functions as a ramp, as described for example in relation to reference numbers 105 and 107 in FIG. 2.

This outflow channel 414 is detailed further in reference to FIG. 6. In certain embodiments, the outflow channel 414 is further comprised of several microfluidic channels 424, 418, 422, and configured such that one of these microfluidic channels has a portion 422 facing the reservoir 402. Returning to FIGS. 5A-6, from this first "open" area 424, the fluid is then able to flow to the "closed" microfluidic channel 418, and then again to a second "open" microfluidic channel 422, such that it is urged or otherwise brought into contact with the inner surface 420 of the tube 402 and collected in the reservoir 402 by way of a fluidic bridge. In these embodiments, the open microfluidic system therefore allows capillary flow of the blood to the exposed portion, allowing contact of the blood or bodily fluid with the reservoir 402.

Figure 5D:
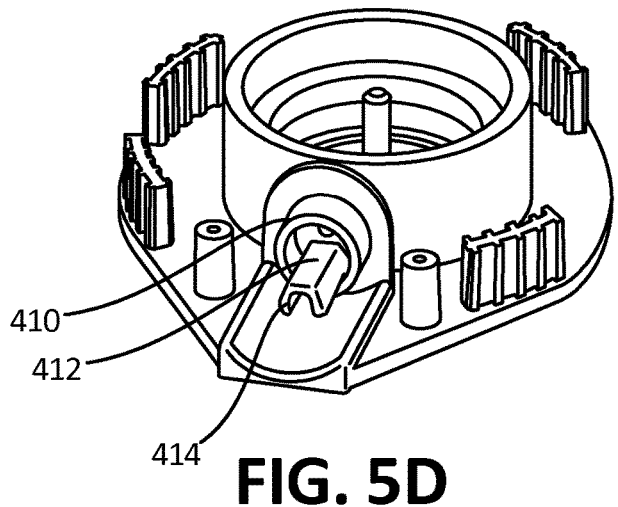
FIG. 5D is a cutaway perspective view of the collector, according to an exemplary embodiment.
Figure 5E:
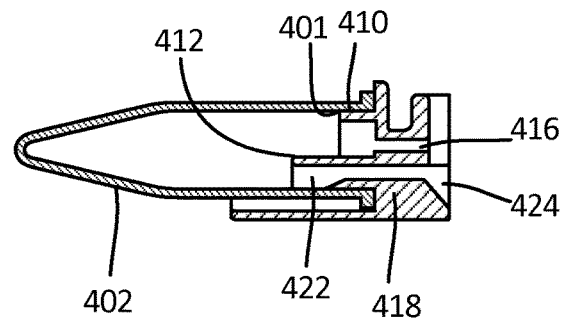
FIG. 5E is a cross-sectional side view of the outflow channel and reservoir, according to an exemplary embodiment.

Accordingly, and as shown in FIGS. 5D-6, the shape the outflow channel 414 can vary along its length to first enhance capillary flow to include a closed microfluidic channel 418 and progressively increase the cross-sectional length connected to the inner surface of the tube 420 (as is shown at the ramp at 422) in order to force the fluid to connect with the inner tube surface, bridge and flow into the reservoir 402. Accordingly, open microfluidics associated with gravity allow the flow of blood along an outflow channel 414 without causing it to "pin" or otherwise stop or pool when the fluidic path suddenly opens into the reservoir 402. These open microfluidic methods allow the gradual transition towards creating a drop of blood or a blood connection with the tube, thereby preventing blocking, pinning, or clogging. As best shown in FIG. 5E, the air opening 416 between the volume of air contained in the reservoir 402 and the volume of air in the device 400 with the shape of a cylinder or any other shape allows the equilibration of air pressures between the reservoir 402 and the inside of the device 400 while the fluid is filling the reservoir 402.

In various embodiments, certain open microfluidic channels, such as those depicted in FIGS. 6B and 6C. In embodiments wherein the ramps are working against gravity, they may be composed of free surfaces and wetted surfaces satisfying the SCF relation (as laid out by Equation 3, stating that the ratio of the length of the cross-section of channel spanning over the at-least one free surface the length of the cross-section of channel spanning over the at-least one wetted is less than the cosine of the contact angle of the fluid on the wetted surface), which thereby allows spontaneous capillary flow. In various alternative embodiments wherein the ramps work with the assistance of gravity, the SCF relation need not be satisfied.

Importantly, the ability to connect an integrated blood collection device with a detachable reservoir 402 or cartridge (shown in FIG. 19 at 1900) has many advantages. One advantage is the ability to simply couple or otherwise interface the reservoir with downstream equipment and measuring devices. The ability to simply press or screw a tube or other collection device onto the integrated blood collection device allows the use of any desired tube for downstream applications, including tubes for various assays and applications, such as PCR, which in certain embodiments may contain PCR reagents, as shown at 426 in FIG. 6, as well as various microcentrifuge tubes, tubes containing gel for plasma separation, standard tubes used in blood analysis laboratories for pediatric applications, tubes that perform a specific assay directly within the tube, tubes that stabilize or otherwise store the blood for shipping, and capillary blood collection tubes. The tubes connected to the integrated bodily fluid collection device can also be specific to blood collection, including tubes that contain EDTA, heparin, serum separation gel, biomarker stabilization reagents, or any other pre-processing blood collection tube. A tube can also be replaced by a customized reservoir that is used for dedicated downstream equipment or processes. While the examples provided herein refer to a tube, as would be apparent to one of skill in the art, various embodiments of fluid containers are well within the scope of the embodiments described herein.

Another advantage of the detachable reservoir being in fluidic communication with the outflow channel is that the fluidic transfer from the tissue to the reservoir is engineered to simplify the multi-step process of blood collection into a single step process. Therefore, the user of the device does not need to be trained in the art of tissue puncture, device handling during the fluid transfer process, or post-collection processes including tissue sealing, handling of an exposed biospecimen, or other processes. The integrated collection device described includes open microfluidic fluid transfer but the device can perform the fluid transfer using any number of transfer mechanisms including metal tubing, plastic tubing, and/or sealed microchannels. The tube or reservoir is sealed from the exterior environment post-collection and can remain so during detachment of the tube and after the tube is detached. The tube or collection reservoir filled with the bodily fluid can be detached by twisting, pulling, activating a release mechanism, or any other secondary step. This tube can then also have a known features, device, or component that provides for self-sealing the tube during and following detachment. Alternatively, the removal mechanism can activate other steps that may be helpful in stabilization, sample preparation, or diagnostic analysis.

Gravity-enhanced microfluidics can be utilized to precisely control the nature of the fluidic connection between the device and the tube. In the embodiment described in FIGS. 5A-6, only a single section of the open microfluidic path 422 is removed to allow connection with the tube 420, thereby ensuring that sufficient capillary force allows the fluid to be flowed past the change in geometry, as is also described in the commonly assigned U.S. patent application Ser. No. 13/949,108, filed on Jul. 23, 2013, which is incorporated by reference in its entirety. A central aspect to such embodiments is the ability to reliably transfer fluids between a collection device and a reservoir utilizing open microfluidic systems.

The use of such open microfluidic methods allow for outflow channels 414 that can be transiently in contact with a reservoir, container, or reservoir 402 while allowing reliable and simple fluid transfer between the various aspects. In certain embodiments, the outflow channel 414 favors capillary flow at the innermost aspect by presenting a closed channel geometry thus allowing a robust draining of the fluid into the outflow channel from the microfluidic network. Progressively, the geometry of the fluidic path along the outflow channel varies to an open channel configuration in which part of the fluid is allowed to come in contact with the air or a different surface, as is shown at 422. In order to ensure a strong probability of contact, that interface must be large enough to allow the fluid to contact the new surface and create a drop of sufficient volume that it flows by itself on the surface 420. This flow can be enhanced by surface treatment of the reservoir through a surface activation or the addition of a dried reagent that reduces the surface energy of the material and allows increased wetting by the fluid or implementing a material in the manufacture of the features that has a preferential surface energy, such as a hydrophilic plastic. Importantly as there is no binding material between the outflow channel and the receptacle or tube it can be removed or placed back in contact when needed.

As is shown in FIGS. 6B and 6C, these open microfluidic channels 450 typically involve at least one free surface 452 and at least one wetted surface 454 defining boundaries of a cross section 456 known as the "free perimeter" (at 462) and "wetted perimeter" (at 454), respectively. In certain exemplary embodiments, the cross-section 456 of the microfluidic channel 450 verifies the SCF relation stating that the ratio of the length of the cross-section spanning over the at-least one free surface 452 to the length of the cross-section spanning over the at-least one wetted surface 454 is less than the cosine of the contact angle 458 of the fluid 460 on the wetted surface 454, ensuring that fluid spontaneously flows by capillary force along the open channel 450.

Figure 7A:
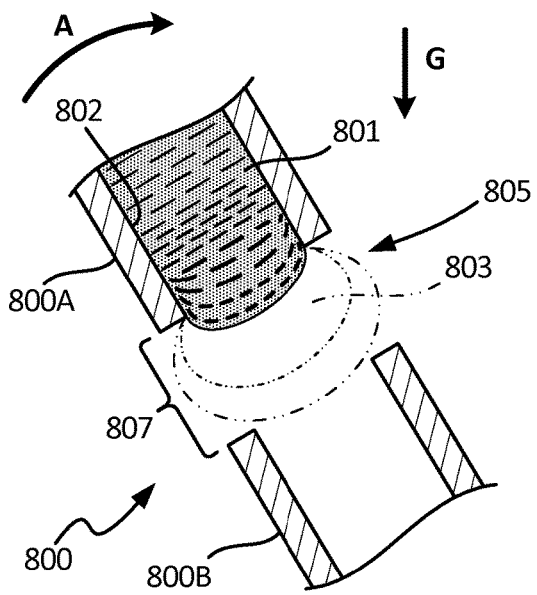
FIG. 7A is a cross-sectional view of a surface tension valve in a closed position, according to an exemplary embodiment.
Figure 7B:
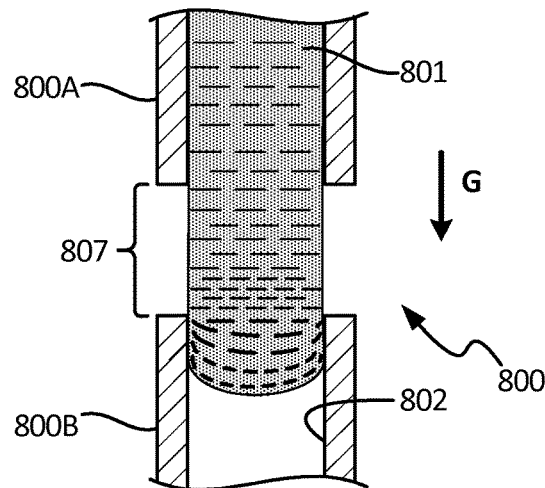
FIG. 7B is a cross-sectional view of the valve of 7A in an open position.

FIGS. 7A-7D provide expanded views of microfluidic channels 800 such as those incorporated into the various collector embodiments discussed above. As shown in FIGS. 7A and 7B, in various embodiments of the gravity-enhanced microfluidic system 800, the flow of fluid 801 through a channel 802 can be regulated by way of a surface tension valve 805 placed between the first 800A and second 800B channel portions or lengths and configured such that the fluid 801 reaches a gap 807 in the channel which comprises the surface tension valve 805 and is only able to span over the gap 807 by creating a drop-like feature 803 able to flow along the channel 800. In exemplary embodiments, this is only possible when the channel 800 is placed substantially vertically (as by rotation around reference arrow A) such that the fluid is flowing with the gravitational field (shown by reference arrow G). In these embodiments, an opening 807 is created in the channel path 800 between the first 800A and second 800B channel lengths such that the fluidic network is disconnected for most traditional fluid flows, as shown in FIG. 7A, where the surface tension valve 805 is preventing the flow of fluid 801 through the opening 807.

As is shown in FIG. 7B, when the channel 800 is oriented in a substantially vertical position, the additional force of gravity allows the fluid 801 to overcome these surface tension forces in the gap 807, thereby forcing the fluid to connect with the second portion 800B of the fluidic channel. In these embodiments, once the fluid 801 contacts the second channel portion, a sustainable fluid path is created allowing flow. Further, when the channel 800 is returned to a substantially horizontal position, fluid is then unable to flow back into the first portion 800A fluidic network.

Figure 7C:
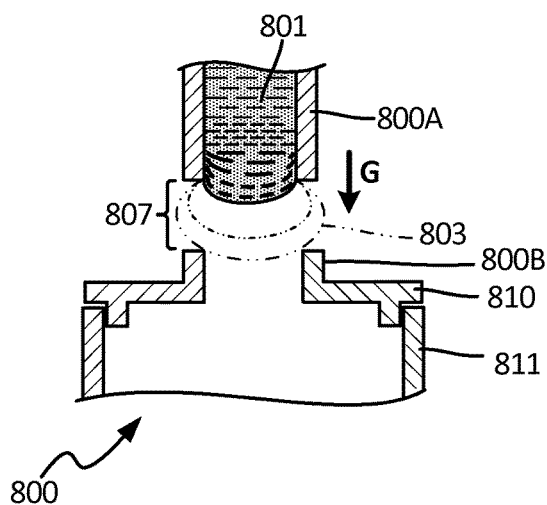
FIG. 7C is a cross-sectional view of an alternative embodiment of a valve and channel configuration in the collector.
Figure 7D:
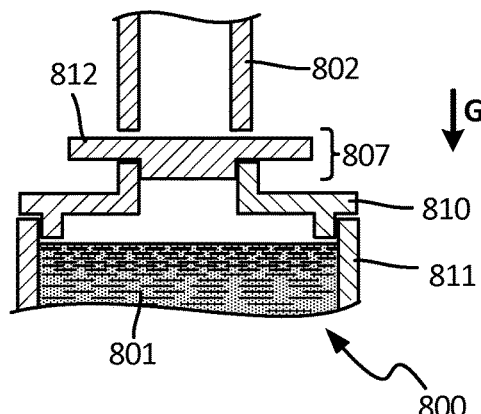
FIG. 7D is a cross-sectional view of another alternative embodiment of a valve and channel configuration in the collector.

As is shown in FIGS. 7C and 7D, in another embodiment, fluid 801 flowing down a first channel portion 800 reaches a gap 807 in the channel 802 and is only able to span over the gap 807 by creating a drop-like feature 803 that contacts the second channel portion 800B, which in this embodiment further features an expansion 810. Once the fluid 801 has connected to the second channel portion 800B, it is able to fill a reservoir 811, which is situated opposite the expansion 810. At any time or at the end of the flow, a lid 812 can be placed in the gap 807, allowing the sealing of the second half of the microfluidic channel 810 as well as the reservoir 811.

Figure 8:
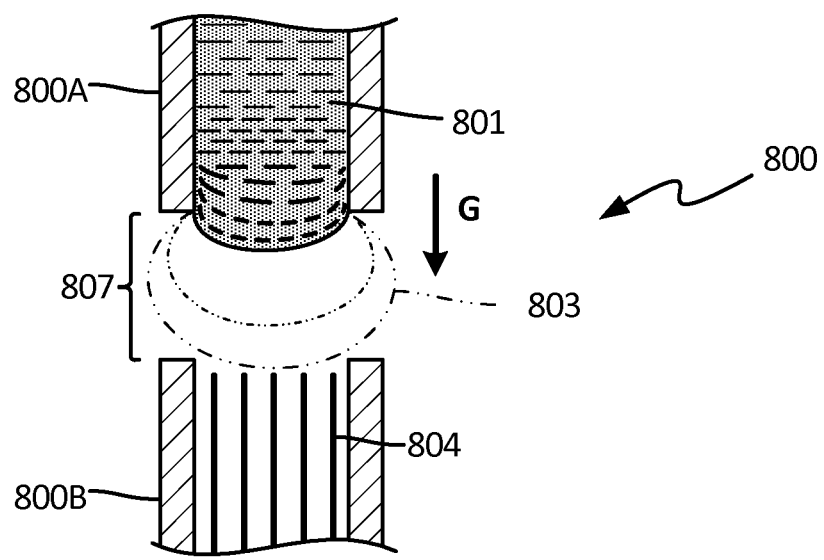
FIG. 8 is a further cross-sectional view of another alternative embodiment of a surface tension valve and channel configuration in the collector.

As is shown in FIG. 8, in an alternative embodiment, a first channel portion 800A can be designed to control delivery of fluid 801 into a second channel portion 800B. Fluid 801, flowing in a channel 800, again reaches a gap 807 in the fluidic network and expands into a drop-like feature 803 if and only if the fluid is flowing in the direction of the gravitational field, as has been discussed. Once the drop-like feature 803 connects to the second channel portion 800B, a pre-determined volume of the fluid will be released from the drop-like feature 803. In these embodiments, the connection occurs when a droplet (the volume of which is easily determined through standard equations) reaches a height that is equal to the length of the gap 807. At that volume, fluidic connection occurs, the droplet is drained to the other side, and the interface recedes to a low volume position. The fluid 801 is thereby applied to the second channel portion 800B periodically and with controlled and tailored volumes. The addition of additional channel features 804, such as capillary fins, surface tension guides, protrusions or thin-walled ridges disposed within the second channel 800B can assist in the wicking of the expanding drop-like feature 803 into the second half 800B of the microfluidic network. Once the drop-like feature 803 is released, the fluid in channel 802 will recede back to the position of the gap and in reference to the Bond number discussed, e.g., in relation to FIGS. 1E and 1F. In various implementations, this process can repeat as long as there is available fluid 801 to be delivered to the system.

Figure 9A:
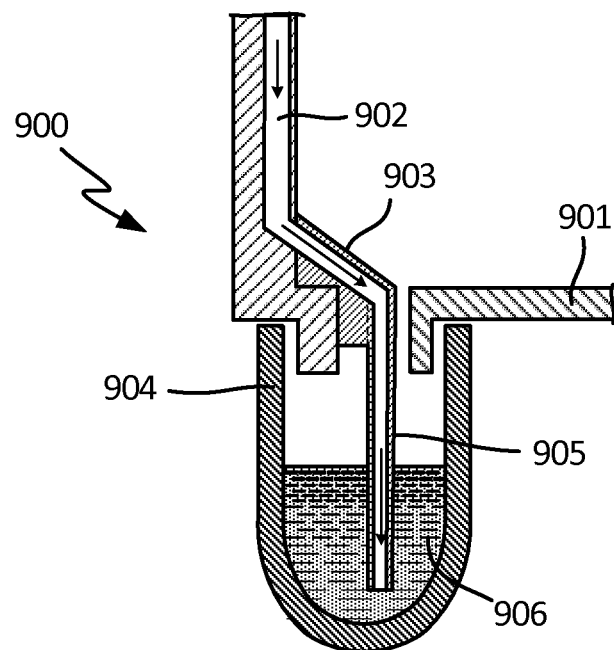
FIG. 9A is a cross-sectional side view of an exemplary embodiment of an outflow channel in the reservoir.
Figure 9B:
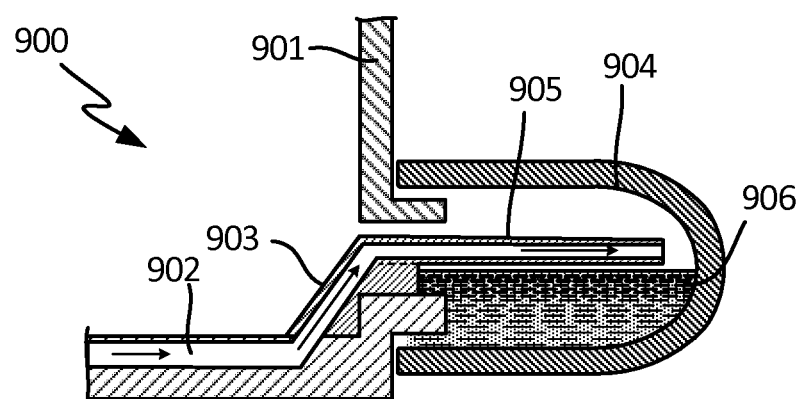
FIG. 9B depicts the channel and reservoir of 9A in a horizontal position.
Figure 9C:
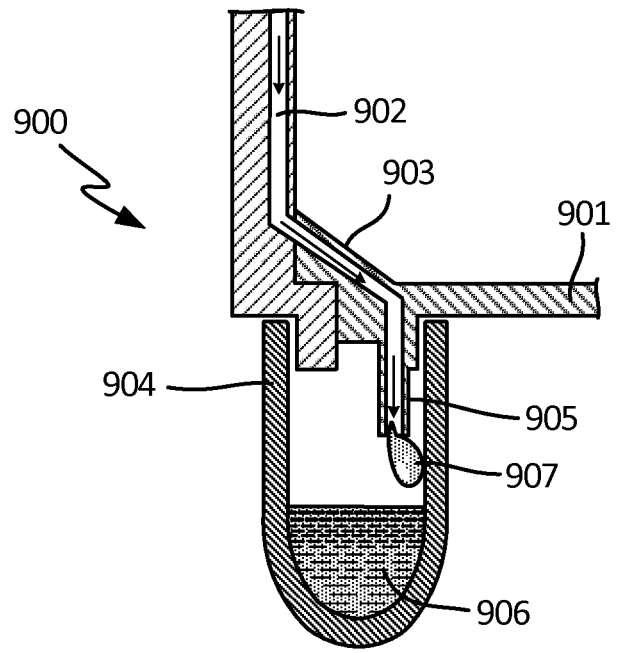
FIG. 9C is a cross-sectional side view of an alternative exemplary embodiment of an outflow channel in the reservoir.
Figure 9D:
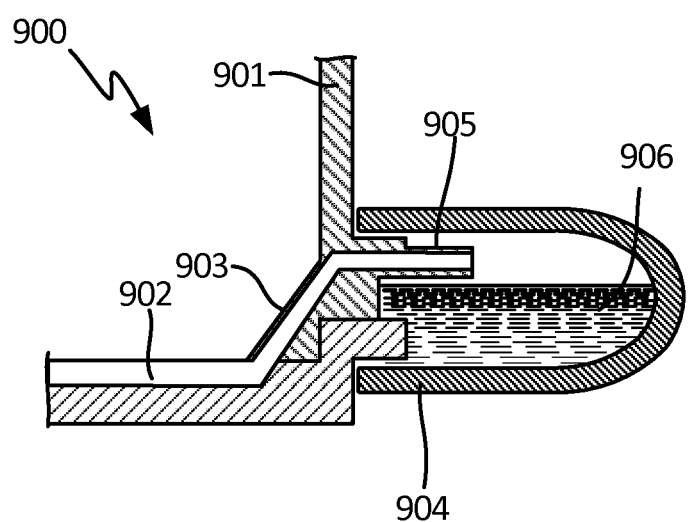
FIG. 9D depicts the channel and reservoir of 9C in a horizontal position.

In the embodiment depicted in FIGS. 9A-9D, various microfluidic networks 900 can be utilized which connect with a reservoir, or tube 904 (as discussed variously herein, such as in relation to FIGS. 1A-1C) such that fluid 906 can flow into the tube 904 when upright (as is shown in FIGS. 9A and 9C), but not flow back out of the tube 904 when placed horizontally (as is shown in FIGS. 9B and 9D). This can be accomplished by designing a channel with an appropriate Bond number relative to the angles at which it will be disposed, as is discussed above in relation to FIGS. 1E and 1F. In these embodiments, gravity is significant, and the fluidic paths will be influenced by gravity such that they may take different paths as the device is placed in different orientations.

In these embodiments, when the collection device 901 is substantially upright (as depicted in FIGS. 9A and 9C), the fluid 906 is able to flow through the internal microfluidic network 902 (as described in relation to FIGS. 2A-4D) and is raised from that channel surface through a ramp 903 into the tube 904 by capillary action and gravity. An outflow channel 905 is in fluidic contact with the inner surface of the tube 904 (which may occur either at the top or bottom of the tube, as is also described in relation to FIGS. 16A and 16B). The outflow channel 905 thereby delivers the fluid 906 into the tube 904 either by proximal fluidic connection with the bottom of the tube so as to create a fluidic bridge and fill the tube (FIG. 9A) or by creating a fluidic bridge 907 with the side of the tube (shown in FIG. 9C) that drips down the side and into the tube 904, thereby filling it.

When moved to the horizontal position (as depicted in FIGS. 9B and 9D), if the fluid 906 falls to the bottom of the tube 904 or if the fluid is capillary pinned in the tube 904 via changes in surface tension, such as by changing the tube design, engineered microfluidics, material selection and/or low fluid volume, the fluid 906 cannot flow back out of the tube 904 into the device 901. In this way, bodily fluid can be collected and prepared for removal or shipping without the possibility of leakage.

Figure 10:
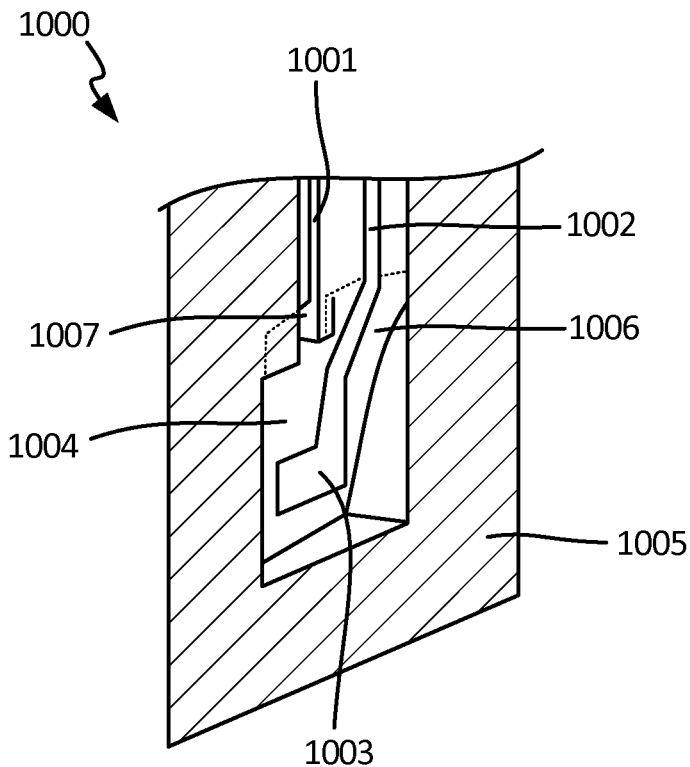
FIG. 10 depicts a perspective cross-sectional view of a collection well, according to an exemplary embodiment.

In an embodiment depicted in FIG. 10, exemplary embodiments further comprise a reservoir 1000 which is a detection well 1004. In these embodiments, the well 1004 is configured such that electronic probes having detection pads 1003 can be integrated into the well 1004 by one or more electrical leads 1002 so that fluids can be applied to the well 1004 by one or more outflow channels 1001. One of the obstacles to placing leads into wells is that leads cannot be run across or over right angles, and instead require less abrupt changes in direction for fabrication simplicity. In these embodiments, an open well 1004 is provided such that at least one outflow channel 1001 can deliver fluids into the open well 1004 and electrical leads 1002 can be integrated into the well for analysis and detection by way of the pad 1003 or pads in a manner which does not require the leads to be placed over a sharp corner.

The smooth transition 1006 enables electrical contact of the lead 1002 with the detection pad 1003 during its transition into the well 1004. Utilizing gravity ensures the filling of the open well 1004 as fluid is flowing down from outflow channel 1001 despite the well 1004 not having a defined contour on its entire periphery 1005. The ability to define smooth transitional surfaces 1006 into the well 1004 facilitates low-cost electronic patterning technologies, including ink-jet printing. Further, in the depicted embodiment, the outflow channel comprises an outflow channel 1001 which is a deep channel 1001 which is further in fluidic communication with a connecting channel 1007, thereby allowing the controllable flow of fluids through the connecting channel 1007 across the smooth transition 1006 by the formation of a fluidic bridge, as has been previously discussed. In various embodiments, these electric leads 1002 can be easily imprinted, ink jet printed, or patterned into the well 1004 by a shallow and smooth transition 1006.

Figure 11:
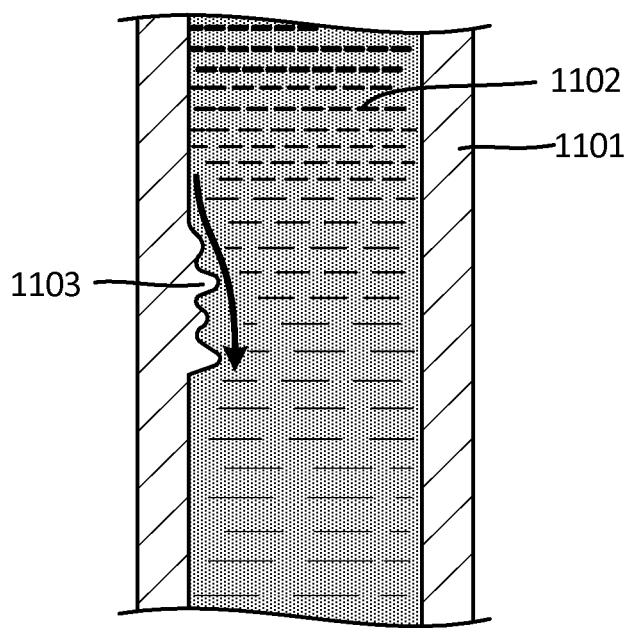
FIG. 11 depicts a cross-sectional view of fluid flow through a channel having defects according to an exemplary embodiment.

The use of gravity in combination with capillary forces allows the collector to overcome manufacturing defects. By way of example, FIG. 11 depicts a channel 1101 that can be incorporated into any of the collector embodiments discussed elsewhere herein, such as in the microfluidic network within the lumen, the outflow channels, or ramps. This exemplary channel helps to explain some of the benefits of gravity-assisted microfluidic devices with respect to manufacturing due to the reduction in the need for precision. When the channel 1101 is held in a position that allows the fluid flow to be assisted by gravity, fluid 1102 can flow past pinning ridges 1103, which can result from unintentional manufacturing defects, dust particles, or other capillary interferences. This ability to pass such ridges 1103 to make the fluid flow, and therefore the collector devices more reliable. Accordingly, in various embodiments, the precision of the channel dimensions and/or configurations can be reduced while maintaining reliable fluid flow.

As is shown in FIGS. 12A-12D, by using gravitational assistance, certain exemplary embodiments of the collector can comprise microchannels which contain surface tension guides which can run substantially the length of the channel 1200 and influence the direction of fluid flow within it. More specifically, in various embodiments, these microfluidic channels 1201 can be designed with surface tension guides 1202 in the form of fluidic pinning ridges or hydrophilic patterns 1202 which allow a fluid 1203 to be guided in a specific direction. In this way, when the devices are oriented such that gravity assists the direction of the flow (as is shown in FIGS. 12A-12D), fluid can be more specifically manipulated and moved for more complex fluid motion. These manipulations can involve bends in the channel 1204, engineered fluid flow such as velocity or other features that are known to those of skill in the art.

Figure 12A:
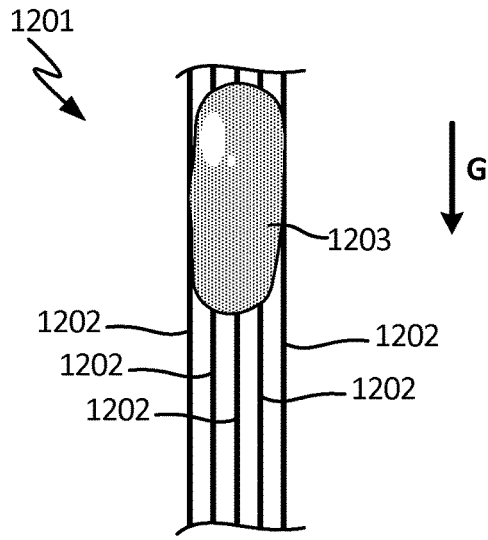
FIG. 12A depicts a top view of one embodiment of microchannels comprising surface tension guides, wherein gravity assists with the direction of flow.
Figure 12B:
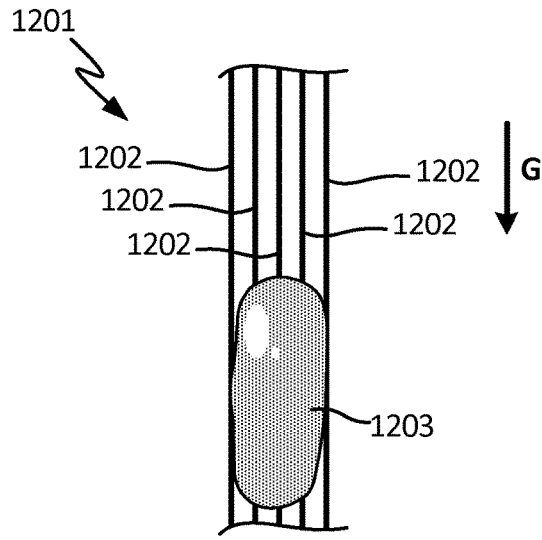
FIG. 12B depicts a top view of the embodiment of FIG. 12A, wherein the fluid has progressed through the microchannels.
Figure 12C:
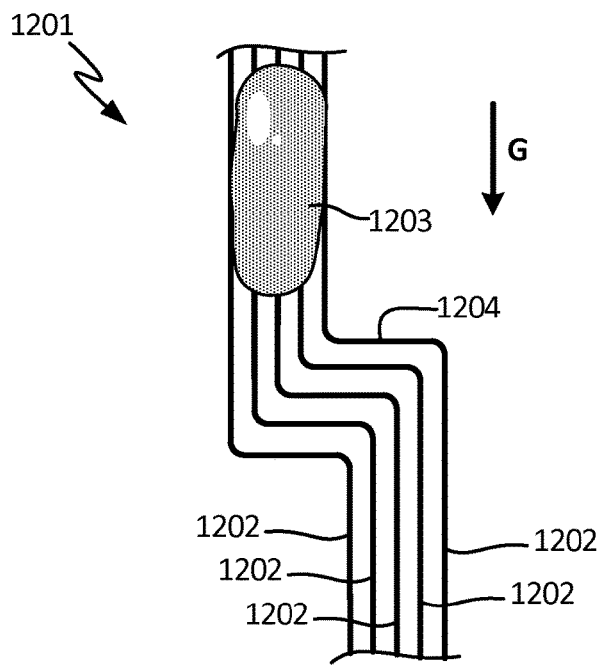
FIG. 12C depicts another top view of an alternative embodiment of microchannels comprising surface tension guides, wherein gravity assists with the direction of flow.
Figure 12D:
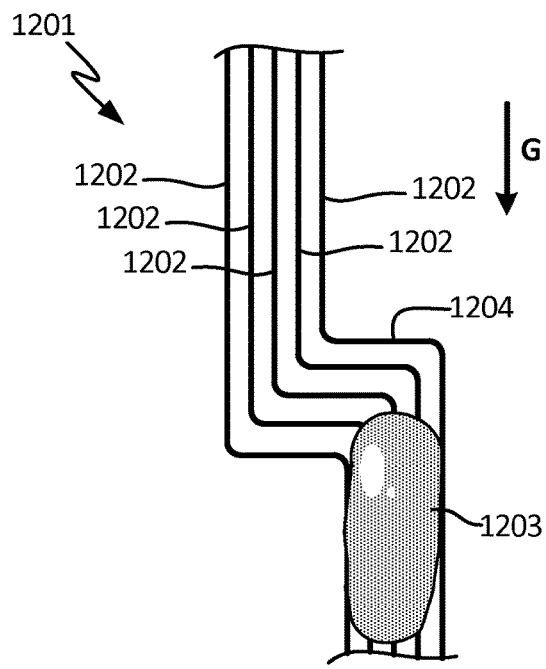
FIG. 12D depicts a top view of the embodiment of FIG. 12C, wherein the fluid has progressed through the microchannels.
Figure 12E:
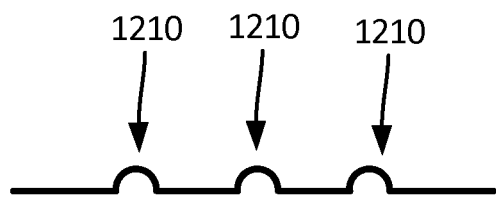
FIG. 12E depicts a side view of an embodiment of a microchannel comprising at least one rounded ridge.
Figure 12F:
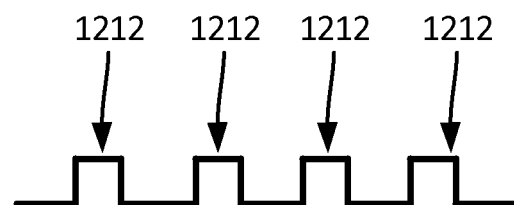
FIG. 12F depicts a side view of an embodiment of a microchannel comprising at least one square ridge.
Figure 12G:
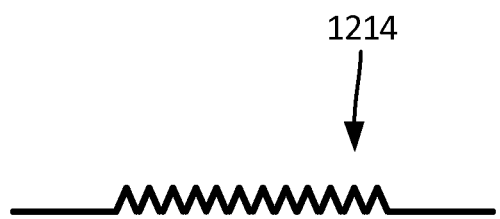
FIG. 12G depicts a side view of an embodiment of a microchannel comprising the surface tension guide is provided by a grooved, textured portion.
Figure 12H:
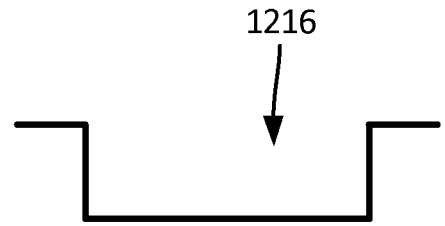
FIG. 12H depicts a side view of an embodiment of a microchannel comprising a typical open channel for comparison.

As shown in FIGS. 12E-12H, the surface tension guides, ridges, or patterns, are simple features that add texture or grooves in the surface, preferably with sharp edges that will incur Concus-Finn capillary flow in the direction of the texture. As can be seen in FIG. 12E, in one embodiment, at least one rounded ridge 1210 can be provided within the channel. As shown in FIG. 12F, at least one square ridge 1212 is given. In FIG. 12G, the surface tension guide is provided by a grooved, textured portion 1214, and in FIG. 12H, a typical open channel 1216 is shown for comparison.

Figure 13:
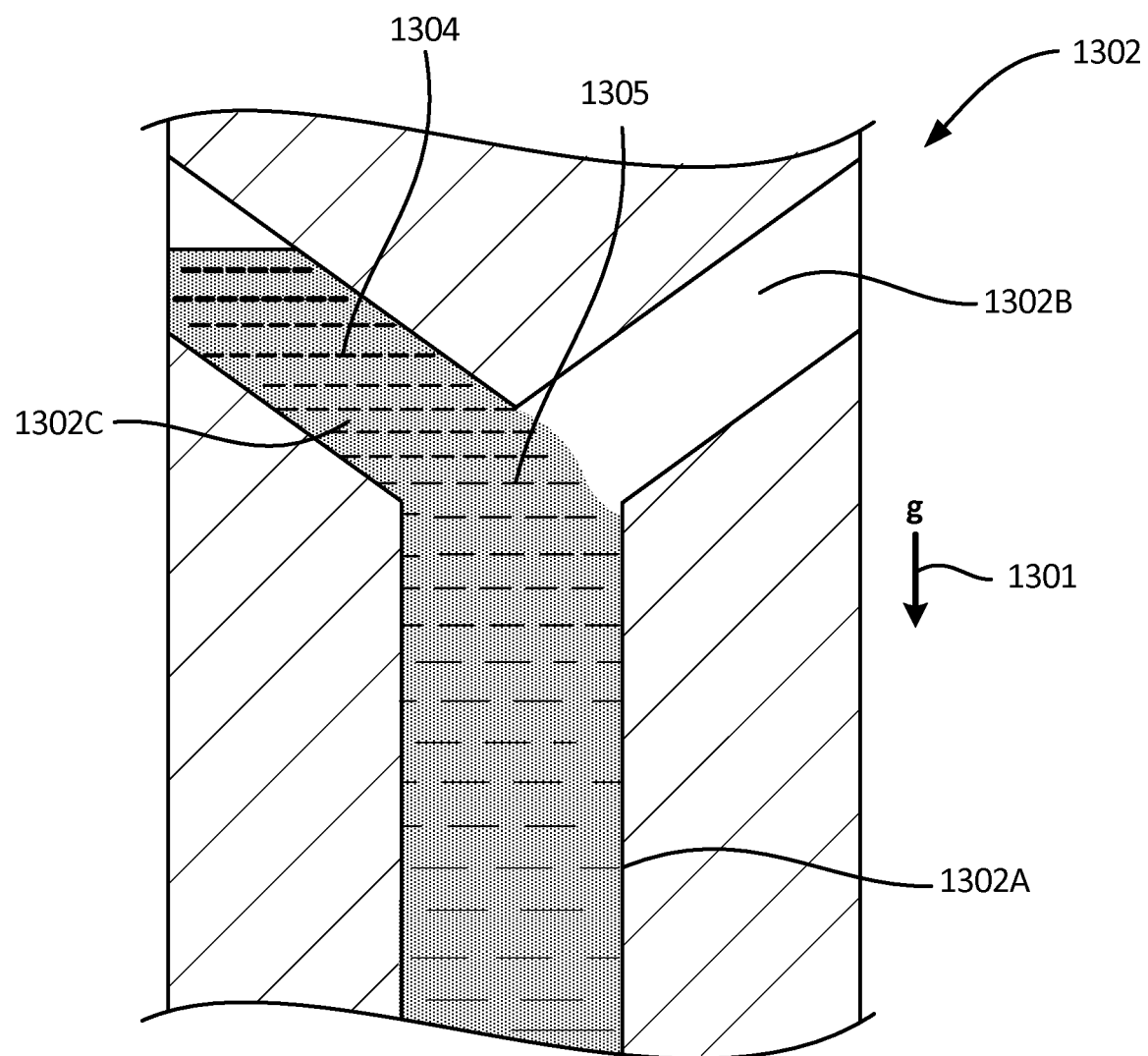
FIG. 13 depicts a cross-sectional view of a directional-flow branched channel, according to one embodiment.

FIG. 13 depicts an alternative embodiment comprising a bifurcated channel 1302 having a primary channel 1302, first 1302B and second 1302C branches and, wherein the channel 1302 is configured to prohibit backflow into an unused branch (such as branch 1302C or branch 1302B). In this embodiment, the primary channel 1302 is oriented so as to have a component of the gravitational force 1301 influence the fluid flow such that fluid 1304 from 1306 will be urged to flow to a confluence or junction 1305 and flow preferentially in the direction of gravity 1301 and into the primary channel 1302 without flowing up into the empty channel 1302B via capillary force. As would be apparent to one of skill in the art, the use of a combination of gravitational forces to overcome any capillary forces can be dictated by the specific application.

Figure 14A:
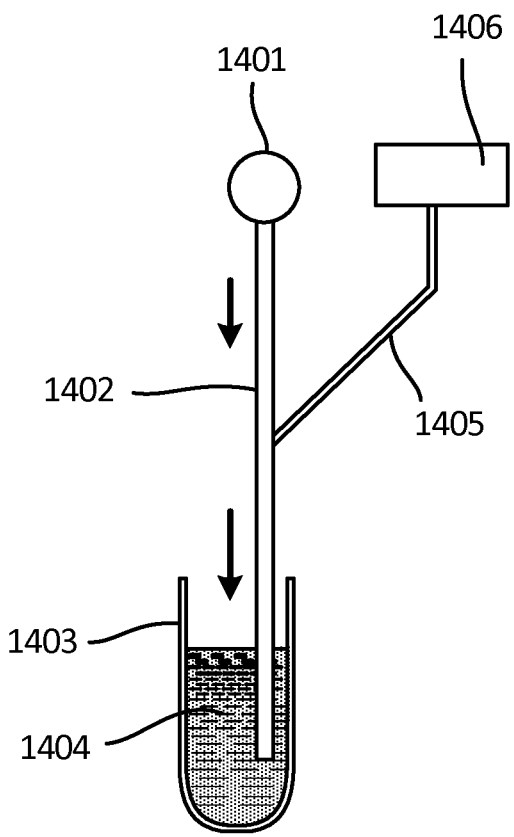
FIG. 14A depicts a cross-sectional view of an embodiment of the collector having an outflow channel and two reservoirs.
Figure 14B:
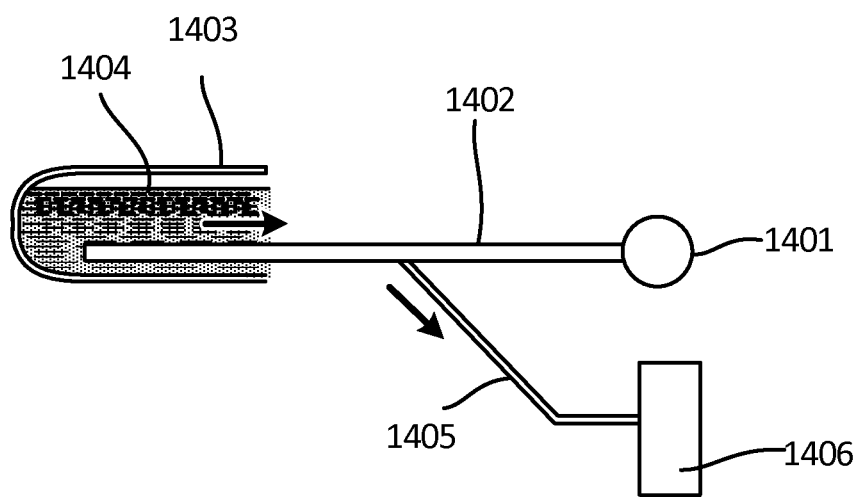
FIG. 14B depicts the channel and reservoir system of 14A in a horizontal position, such that fluid is directed into the second channel and reservoir by gravity.

In the embodiment of FIGS. 14A and 14B, the collector can be used to deliver fluid in a timed manner. In these embodiments, fluid 1404 is collected from a site 1401 and directed along a first channel 1402 into a reservoir 1403. In these embodiments, collected fluid 1404 can then exit the reservoir 1403 when placed horizontally (FIG. 14B) to flow back through the collection channel 1402, through a second channel 1405 and into a second reservoir 1406, because of the introduction of gravitational forces. In certain embodiments, this second reservoir 1406 can also utilize gravitational assistance to allow fluid to flow exclusively into the second channel 1405 instead of the first channel 1402. In this way, tests that need specific timing of fluid addition for chemical reactions or other more specific biological reactions can have the fluid enter the testing chamber (second reservoir 1406) as a single bolus of fluid.

Microfluidic channels such as those discussed in relation to the outflow channels tend to retain fluid. This creates two specific design issues. First is the desire to collect as much fluid from the channel as possible in the reservoir. Second is the need to prevent fluid backflow into the outflow channel when the orientation of the reservoir is changed and fluid which has gathered in the reservoir can come back into contact with fluid retained in the outflow channel, thus causing backflow. Various outflow channel embodiments are disclosed herein which address aspects of these issues. In certain implementations, the outflow channel is in direct fluidic communication with the side of the tube, such as is shown in FIG. 3D. However, when inverted or positioned such that the tube is on its side (or horizontal), these embodiments may allow a simple fluid path for the fluid to drain back into the collector. To avoid this reverse fluid flow, various alternative outflow channel geometries were created that will allow device inversion without contact between the fluid and the outflow channel, such as those discussed at FIGS. 9A-9D and in relation to FIGS. 15A-16E.

Figure 15A:
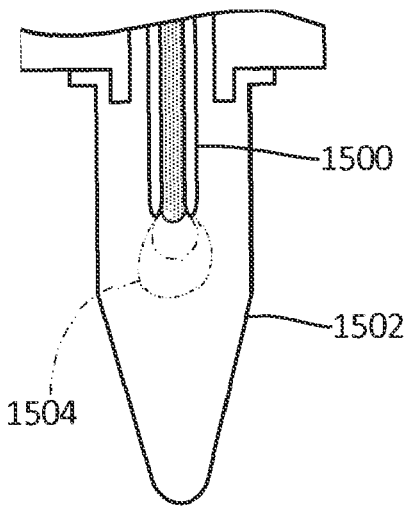
FIG. 15A depicts a side view of a reservoir and outflow channel according to an exemplary embodiment.
Figure 15B:
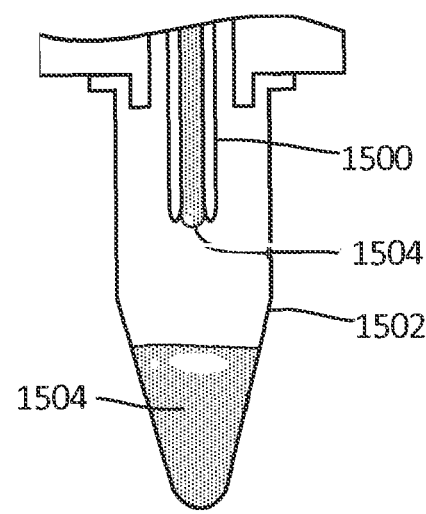
FIG. 15B depicts the embodiment of FIG. 15A, wherein the fluid has been transferred to the distal end of the reservoir.

FIGS. 15A-15D depict various embodiments of an outflow channel 1500 that allow device inversion without the fluid in the tube coming into contact with the outflow channel and the fluid retained there, as shown in FIG. 15B. In these embodiments, the outflow channel 1500 extends from the collector such that the distal end of the channel 1500 is disposed within the tube or reservoir 1502, thereby providing the initial transitional point for the flow of fluid 1504 (as is described herein, for example, in relation to FIGS. 5A-6C). The outflow channels in FIGS. 15A-15D and 16A-16E are similar in that they contemplate outflow channel geometries that act as one-way flow valves. In this sense, the fluid is able to flow by dripping into the tube, but when the device and tube are inverted, the channel 1500 will not allow backflow out of the tube.

Figure 15C:
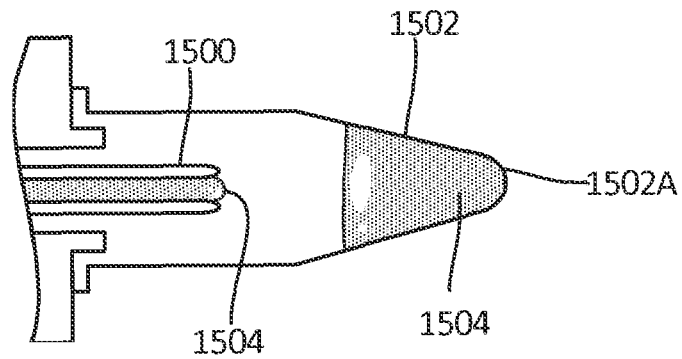
FIGS. 15C and 15D depict the embodiment of FIG. 15B in a horizontal orientation.
Figure 15D:
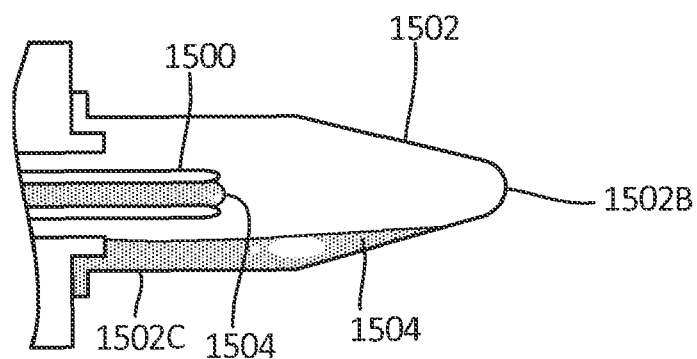

This specific action is shown in FIGS. 15A-15C. In FIG. 15A, the fluid 1504 flows out of the outflow channel 1500 into the tube 1502. When the flow of fluid 1504 is complete as shown in FIG. 15B, the fluid 1504 is within the tube 1502. When the device is held at a different orientation, as shown in FIG. 15C, the fluid 1504 is retained in the tube 1502 and not allowed to make contact with the outflow channel 1500, which could allow fluid 1504 to flow back into the device via backflow through the outflow channel 1500. In the embodiments of FIG. 15C, this retention is achieved because the shape of the tube tip 1502A and properties of the fluid 1504 are such that surface tension in the fluid is sufficient to hold the fluid in the tip despite the orientation. In contrast, in certain embodiments such as the embodiment of FIG. 15D, surface tension may be insufficient to prevent gravity from drawing the fluid 1504 out of the tip 1502B and down onto the side of the tube 1502C, for example when large amounts of fluid have been collected. In those embodiments, the channel 1500 is positioned in the tube 1502 such that the fluid 1504 disposed along the side of the tube 1502C does not contact the channel 1500, thereby preventing backflow out of the tube.

Figure 16A:
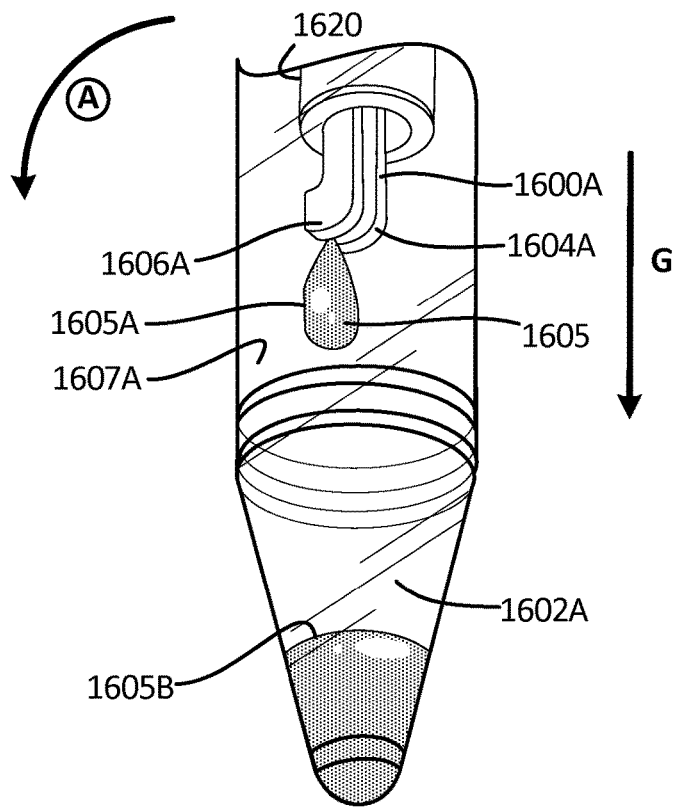
FIG. 16A depicts a perspective, transparent view of a reservoir and an exemplary embodiment of an outflow channel, wherein the channel is configured to be in direct fluidic communication with the bottom inner surface of the reservoir when the collector is in a horizontal position.

Further embodiments of this outflow channel 1500 are contemplated in FIGS. 16A-16E for the same action and purpose as shown here in FIGS. 15A-15D. In FIG. 16A, one embodiment features an outflow channel 1600A having first 1604A and second 1606A channel edges which are in fluidic connection 1605A with the inner surface 1607 of the tube 1602A. That is, the two channel edges 1604A, 1606A are in contact with the inner surface 1607 such that fluid 1605 that flows out of the outflow channel 1600A will come in contact with the inner surface 1607 of the tube 1602A. Thus, when the device and tube 1602A are substantially upright, the fluid is able to flow out from the outflow channel 1600A and into the tube 1602A, and when it is rotated in the direction of reference arrow A fluid 1605 is brought into contact with the inner surface 1607A of the tube.

Figure 16B:
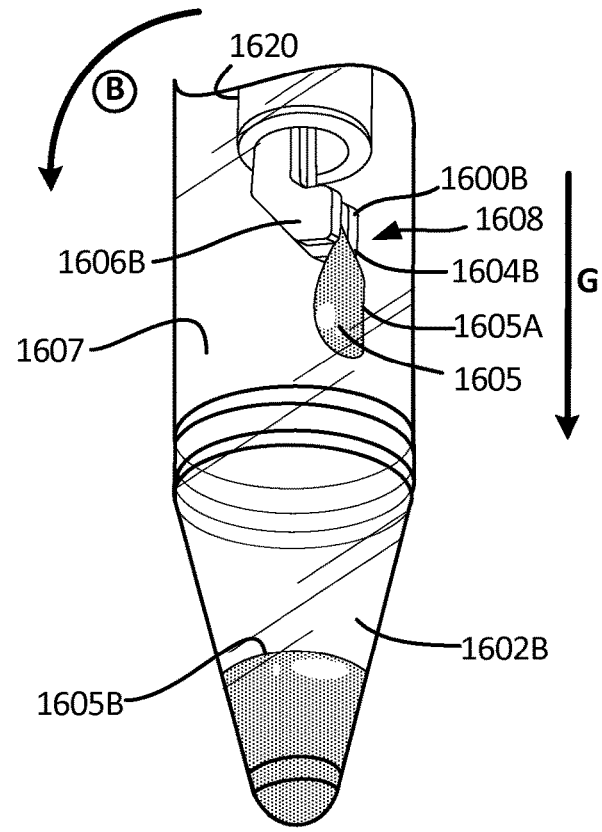
FIG. 16B depicts a perspective, transparent view of a reservoir and an exemplary embodiment of an outflow channel, wherein the channel is configured to be in direct fluidic communication with the top inner surface of the reservoir when the collector is in a horizontal position.

As is shown in FIG. 16B, an alternative embodiment features an outflow channel 1600B featuring first 1604B and second 1606B channel edges which are in fluidic connection 1605A with the top surface 1608 of the tube 1602B such that when the device and tube are substantially upright, the fluid is able to flow out from the outflow channel 1600B, thereby being brought into contact with the inner surface of the tube 1608. When the tube is laid down flat (in the direction of reference arrow B), the front face of the tube thus becomes the top face, and gravity pulls the fluid 1605 down and away from the outflow channel, thereby preventing fluid flow back into the collector.

Figure 16C:
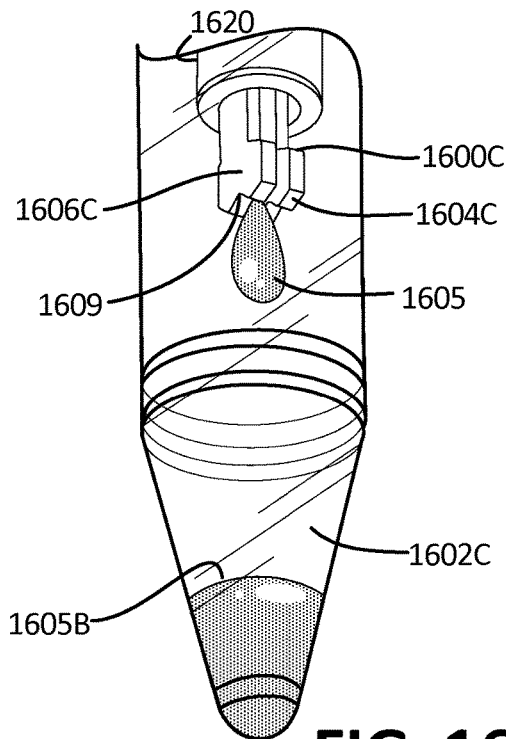
FIG. 16C depicts a perspective, transparent view of a reservoir and an exemplary embodiment of an outflow channel, wherein the channel is in a bulb configuration.

As is shown in FIG. 16C, a bulb-type outflow channel 1600C comprising first 1604C and second 1606C channel edges which form a bulbous shape may be utilized so as to not connect or physically contact to any edge or surface of the tube 1602C. Instead, this outflow channel 1600A allows fluid 1605 to drip from the outflow channel 1600C into the tube 1602C, without a fluidic bridge being formed to the inside of the reservoir 1602C to influence fluid flow. In certain embodiments, notches 1609 at the distal end of these outflow channels can help facilitate droplet formation and droplet detachment, by weakening surface tension forces in the outflow channel.

Figure 16D:
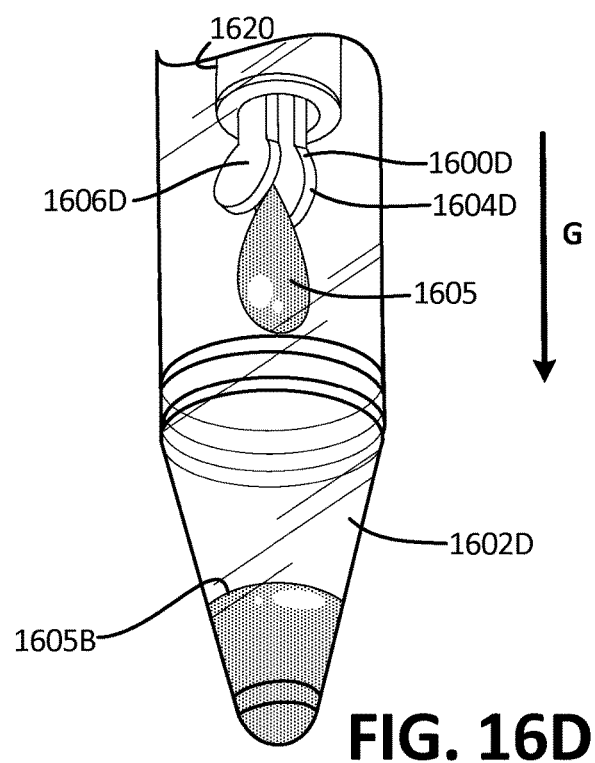
FIG. 16D depicts a perspective, transparent view of a reservoir and an exemplary embodiment of an outflow channel, wherein the channel is in a splayed configuration.

As is shown in FIG. 16D, a splayed outflow channel 1600D is utilized, wherein the first 1604D and second 1606D channel edges extend away from one another at the distal ends. This splayed configuration accommodates fluid drop into the tube 1602D by increasing the space between the first 1604D and second 1606D channel edges, thereby increasing the relative role of gravity on the fluid when dripping.

Figure 16E:
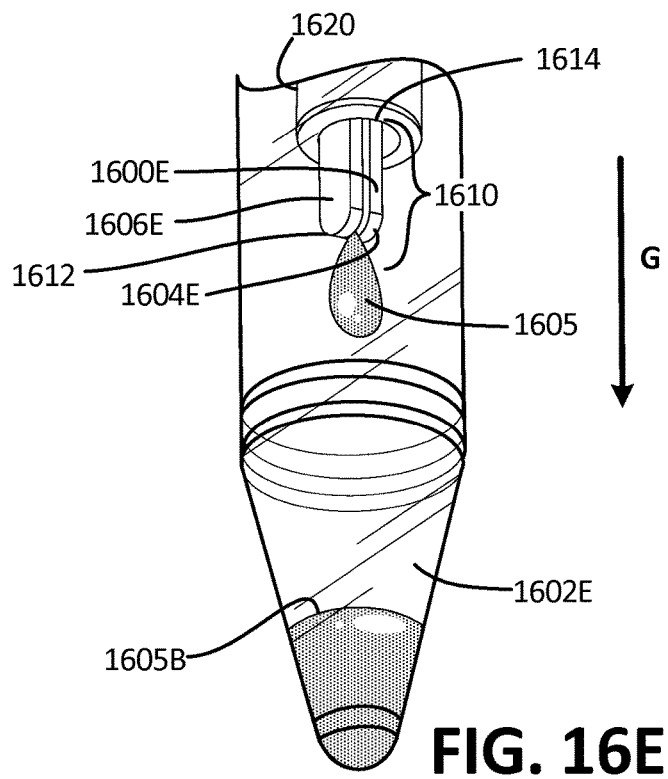
FIG. 16E is a perspective, transparent view of a reservoir and an exemplary embodiment of an outflow channel, wherein the channel is in a straight channel configuration.

Finally, in FIG. 16E, a narrow "straight channel" outflow channel 1600E can be employed, so as to further move the outflow point at the distal end of the channel 1612 away from the top edge 1620 and inner surface of the tube 1602E. In certain applications, the embodiment of 16E is preferred, because these embodiments introduce substantial distance 1610 between the collector and the distal end of the first 1604E and second 1606E channel edges, which prevents dripping fluid from contacting the inner surface of the tube 1602E. This distance 1610, along with the narrow shape of the channel 1600E also reduces the chance of backflow caused by fluidic connection between the fluid 1605 from the outflow channel 1600E and the inner surfaces of the tube 1602E, as increases in distances between surfaces inhibit fluidic bridging. That is, the distance 1610 between the proximal 1614 and the distal ends 1612 of the channel edges 1604E, 1606E reduces the chance of a fluidic connection by releasing the fluid 1605 at a distance apart from both the top edge of the tube 1620 and the top edge of the collecting fluid 1605B, thereby preventing pooling and the creation of fluidic bridges regardless of the orientation of the channel.

Figure 17A:
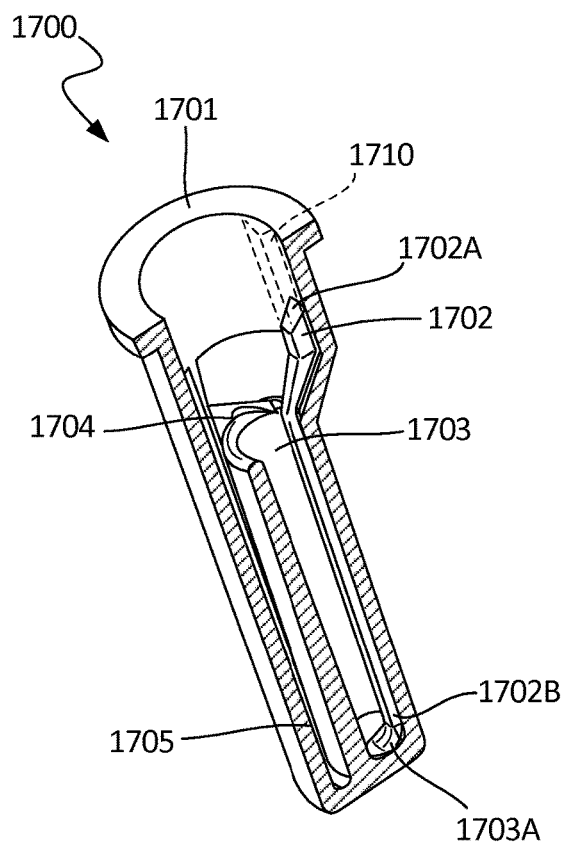
FIG. 17A is a perspective cross-sectional view of a specific volume reservoir, according to an alternative embodiment.
Figure 17B:
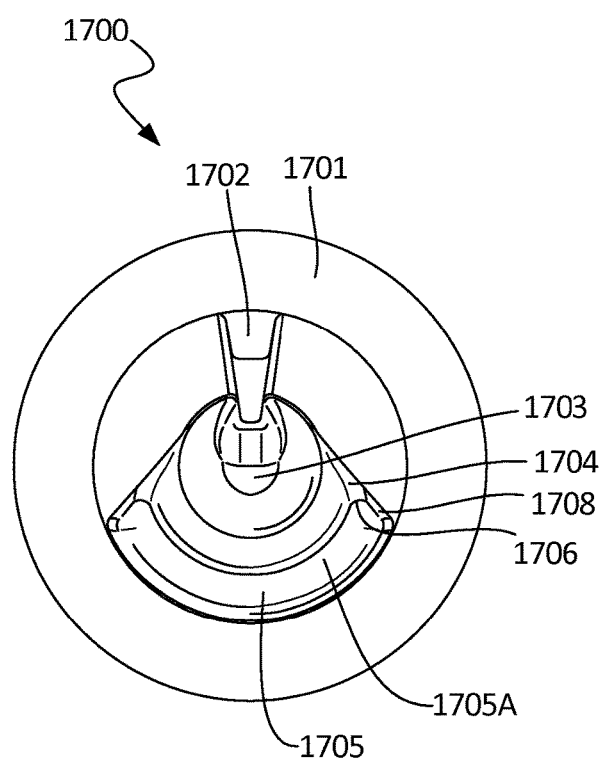
FIG. 17B is an end-view of the embodiment of FIG. 17A.

In FIGS. 17A and 17B, certain alternative embodiments of a specific-volume collection device reservoir 1700 are shown, wherein the reservoir 1700 comprises at least two reservoir channels 1703, 1705. In this embodiment, the reservoir 1700 has an opening 1701, that can be coupled to a fluid collector, including any collector embodiment disclosed or contemplated herein. The opening 1701 may be of the same diameter as a standard tube discussed above in relation to FIGS. 1A-1C. In these embodiments, the reservoir 1700 connects to a blood collection device in such a way that a fixed receiving feature 1702 extends into a first reservoir channel 1703 of defined volume. The receiving feature 1702 is thus fixedly disposed along the wall of the reservoir, such that at the proximal end 1702A it is able to be in fluidic communication with an outflow channel of the collector 1710, and at the distal end 1702B is able to fill the reservoir 1703. The blood being collected is therefore able to contact the outflow channel 1710 more readily than if it required to contact the surface of the tube. Thus the blood will be guided by the receiving feature 1702 to the base 1703A of the first reservoir channel 1703, thereby allowing the first reservoir channel 1703 to be filled first in sequence. Once filled, angled features 1704 on the top of the reservoir 1703 guide excess fluid into a secondary reservoir 1705. The secondary reservoir channel 1705 can thus be utilized as an overfill reservoir, sequestering the excess blood or as a subsequent reservoir for blood containment. In alternative embodiments, multiple reservoirs, such as three, four, five or more reservoirs can be filled sequentially in this fashion.

FIG. 17B depicts a top view of the embodiment detailed in FIG. 17A. Importantly, the second channel 1705 can further comprise a cross-sectional shape that insures efficient filling, as would be understood by one of skill in the art. For example, an angled corner 1706 can be placed on the reservoir 1700 such that it has a higher capillary affinity. In these embodiments, fluid inputted into the secondary reservoir 1705 through the angled features 1704 will contact the narrow portion 1708 of the secondary reservoir 1705 and guide the blood to the bottom floor 1705A of the reservoir, thereby allowing a robust filling without creating air bubbles.

In these embodiments, fluid originating from the collector is drawn into a tube (such as tube 1700) connected to the device that has multiple cavities or reservoir channels (such as channels 1703, 1705 discussed above) of known and precise volume, so as to enable blood collection and analysis in applications that require a specific volume of fluid. The transfer of blood from the device to the tube (such as tube 1700) is facilitated by features along the length of the tube on the inner diameter. These features can be small channels, grooves, or texture that enable capillary guidance of the fluid into the various reservoirs. For example, a single raised outflow channel (such as the outflow channel 1702 discussed above) spanning from the top of the tube to the reservoir can be used to decrease the gap distance between the tube and the fluid output in the blood collection device as well as guide the fluid along the side of the tube into the desired reservoir. This protrusion can be of various heights, such as from 50 um up to several millimeters. Similarly, multiple outflow channels disposed side by side can be used to form an open channel oriented down the side of the tube and into the reservoir of interest. These features protrude outwards to fit into an open microfluidic channel in the device, thereby enhancing the contact of blood from the device to the tube. The blood flows down the tube assisted by the force of gravity. The features guide the flow along the side of the tube into the appropriate reservoir, allowing the initial filling of that reservoir to a specific volume. As discussed above with respect to the tube 1700, once the first reservoir is full, the subsequent reservoirs are allowed to fill, thereby guaranteeing a set volume in the specific reservoir or reservoirs. These features can be used to collect a determined amount of fluid and discard the excess in overfill reservoirs or collect multiple aliquots of blood in separate reservoirs.

Figure 18A:
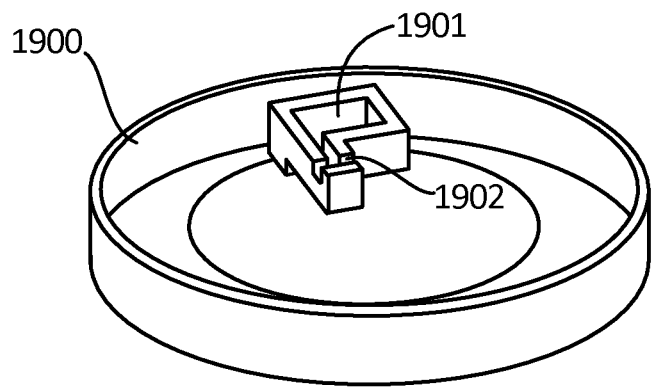
FIG. 18A is a perspective view of a cartridge reservoir, according to an exemplary embodiment.
Figure 18B:
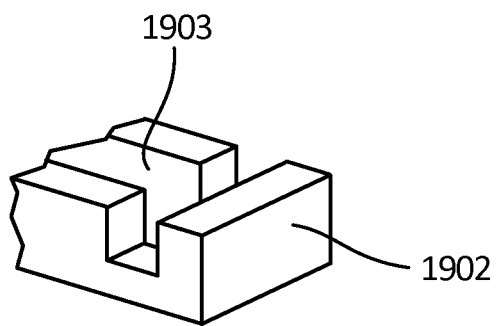
FIG. 18B is a perspective view of an alternative embodiment of the cartridge.
Figure 18C:
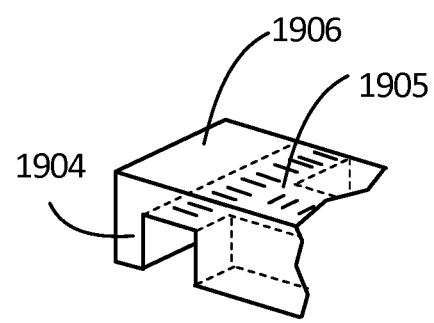
FIG. 18C is a reverse perspective view of further embodiment of the cartridge.

FIG. 18A depicts an embodiment of a circular cartridge reservoir 1900 that can be used with any of the collector embodiments discussed above. In these embodiments, the cartridge 1900 contains a containment region 1901 designed using open microfluidic principles, thereby allowing the reservoir 1900 to be devoid of a ceiling, top, or any type of cover. In exemplary embodiments, the region 1901 has a T-shaped open microfluidic outflow channel 1903 and a protrusion 1902 fluidically connected thereto. The T-shaped channel 1903 has no "ceiling" and is in fluidic communication with the microfluidic network of the collector when coupled thereto. FIGS. 18B and 18C depict the cartridge protrusion 1902 (FIG. 18B) which establishes the fluidic connection with the collector (not shown) (FIG. 18C). As best shown in FIG. 18C, this configuration of the channel 1903 and protrusion 1902 allows for fluid communication with a corresponding collector protrusion 1906, which in this embodiment is oriented with an inverse T-shape relative to the protrusion 1902 and channel 1903 on the cartridge 1900 such that the collector protrusion 1906 is mateable with the protrusion 1902 and channel 1903. The collector protrusion 1906 therefore contains corresponding open microfluidic channels 1904, 1905 as well. Further, in exemplary embodiments, the cartridge protrusion 1902 and collector protrusion 1906 can be freely rotated relative to one another, such that they can be brought into and out of fluidic communication.

These geometries allow the free motion of one protrusion relative to the other as the T shape channel allows for such motion. As the collector protrusion 1906 contacts the cartridge protrusion 1902, blood is able to bridge between the two channels and flow from one to the other, thereby filling the containment region 1901. Fluidic connections can be ceased by simply rotating the cartridge, thereby allowing its removal from the blood collection device.

FIG. 19A through 19F are front views of various handheld device embodiments showing alternative embodiments of the mechanism for retracting the plunger. As described herein, and in many exemplary embodiments, actuation of the handheld device causes the depressing of the plunger by various means, so as to allow for the piercing of patient skin, variously by sliding needles through the apertures or other means, and then the plunger is retracted, in various embodiments thereby creating a vacuum in the lumen that enhances blood collection and facilitates the flow of fluid through the channels and to the at least one sensing area.

Figure 19A:
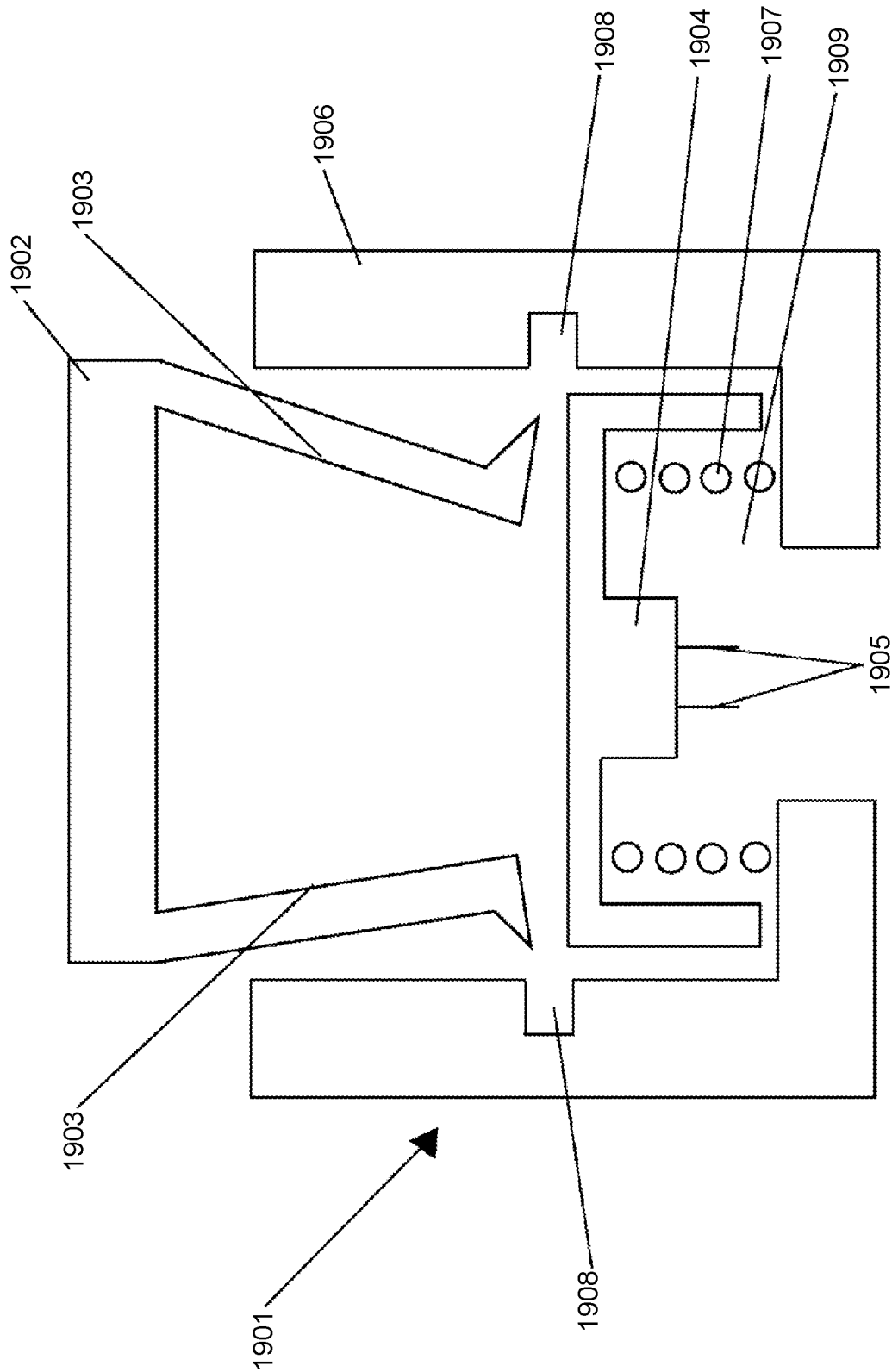
FIG. 19A is a front view of the handheld device showing an alternative embodiment of the mechanism for retracting the plunger of the handheld device.

To use the embodiment depicted in FIG. 19A, a user places the handheld device 1901 in FIG. 19A on a subject's skin and the user imparts a force on a lid 1902 that is positioned proximally from the plunger 1904 to actuate the handheld device 1901. The lid 1902 contains a plurality of leg pieces 1903. When the user imparts a force on the lid 1902, the plurality of leg pieces 1903 move distally in the lumen 1909 and into contact with the plunger 1904, transmitting enough force to the plunger 1904 such that at least one of the plurality of needles 1905 penetrates the subject's skin. The plurality of leg pieces 1903 are designed to radially splay but are also held inside of the lumen 1909 of the body 1906 to ensure reliable contact with the plunger 1904 while the user actuates the handheld device 1901. When the user imparts a force on the lid 1902, the lid 1902 compresses the spring 1907 and moves to a defined displacement, and the plurality of leg pieces 1903 splay into a plurality of grooves 1908 defined in the inner surface of the lumen 1909, allowing the spring 1907 to decompress and proximally retract the plunger 1904, removing the plurality of needles 1905 from the subject's skin and creating a vacuum in the vacuum creation space 1909 created in the lumen 1909 as a result of the proximal retraction of the plunger 1904.

Figure 19B:
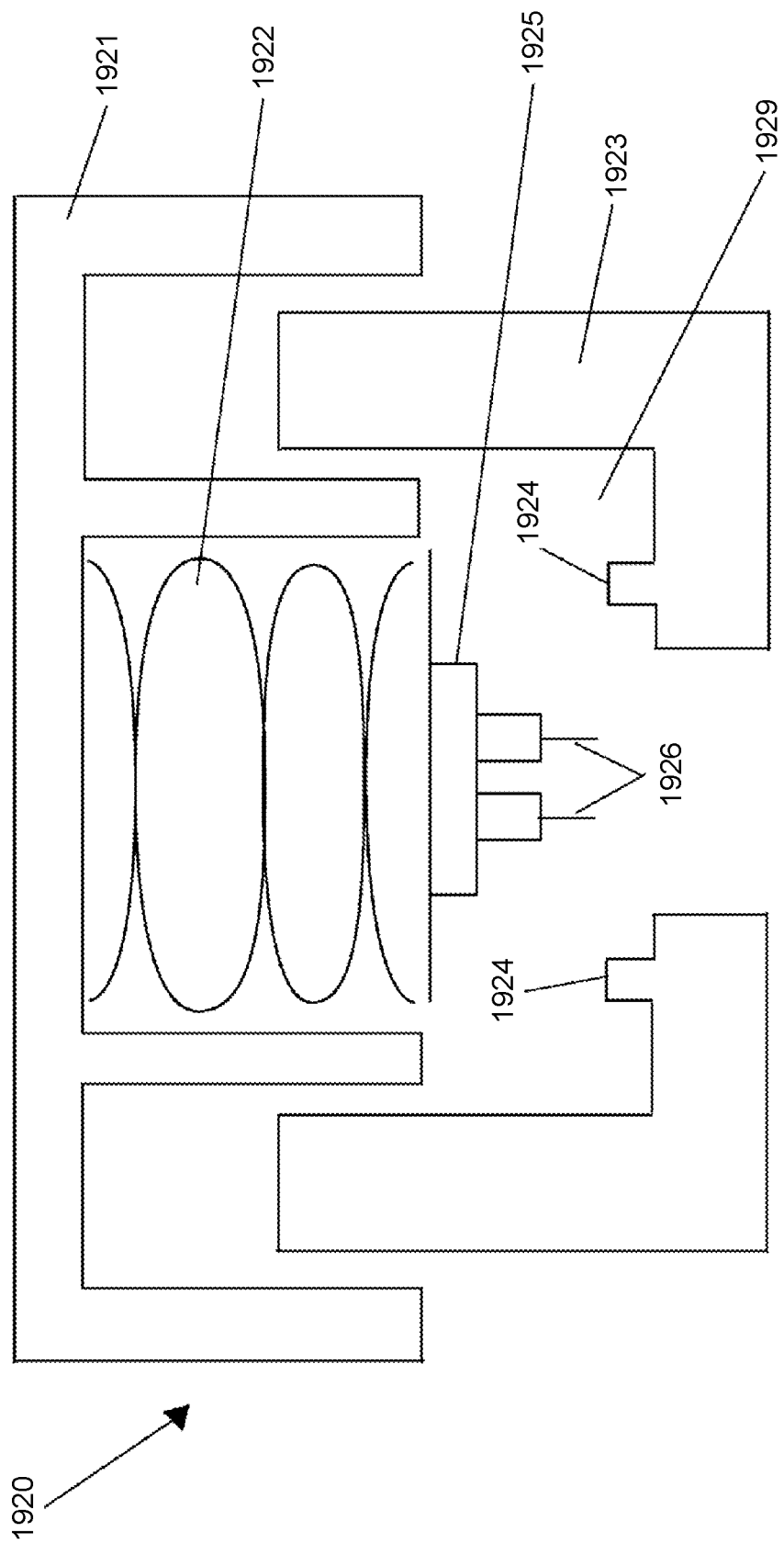
FIG. 19B is a front view of the handheld device showing an alternative embodiment of the mechanism for retracting the plunger of the handheld device.

To use the embodiment depicted in FIG. 19B, a user places the handheld device 1920 in FIG. 19B on a subject's skin and the user imparts a force on a lid 1921 to actuate the handheld device 1920. The lid 1921 contains a collapsible spring 1922. The lumen 1929 of the body 1923 contains a plurality of protrusions 1924, which hold a pre-compressed spring in place. The lid 1921 is in contact with the plunger 1925, and when the user imparts a force on the lid 1921, this compresses the collapsible spring 1922 and transmits enough force to the plunger 1925 such that at least one of the plurality of needles 1926 penetrates the subject's skin. The user-imparted force displaces the plunger 1925 such that the plurality of protrusions 1924 fold into the body 1923, releasing the pre-compressed spring previously held in place by the plurality of protrusions 1924, allowing the plunger 1925 to retract, removing the plurality of needles 1926 from the subject's skin and creating a vacuum in the vacuum creation space 1929. When the plunger 1925 retracts, the collapsible spring 1922 collapses.

Figure 19C:
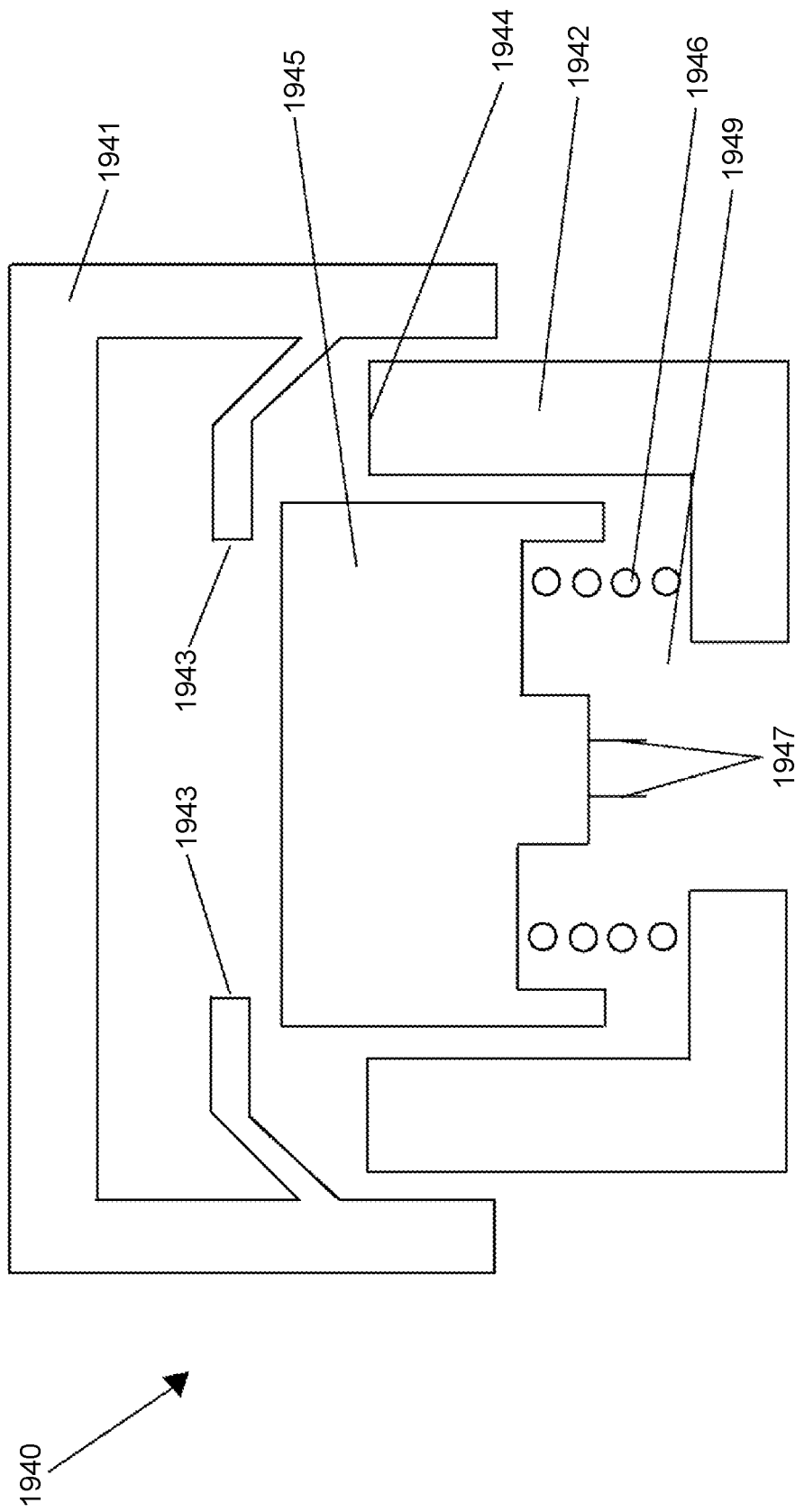
FIG. 19C is a front view of the handheld device showing an alternative embodiment of the mechanism for retracting the plunger of the handheld device.

To use the embodiment depicted in FIG. 19C, a user places the handheld device 1940 in FIG. 19C on a subject's skin and the user imparts a force on a lid 1941 to actuate the handheld device 1940. Lid 1941 is wider than the body 1942 and it contains a plurality of arms 1943 spanning over the proximal end 1944 of the body 1942 and in contact with the plunger 1945. When the user imparts a force on the lid 1941, this transmits enough force distally to the plunger 1945 to compress the spring 1946 enough such that the plunger 1945 moves distally such that at least one of the plurality of needles 1947 penetrates the subject's skin. When the plunger 1945 reaches a defined distal displacement such that plurality of arms 1943 come into contact with the proximal end 1944 of the body 1942, the plurality of arms 1943 fold back, allowing the spring 1946 to retract the plunger 1945, removing the plurality of needles 1947 from the subject's skin and creating a vacuum in the vacuum creation space 1949 created in the lumen 1949.

Figure 19D:
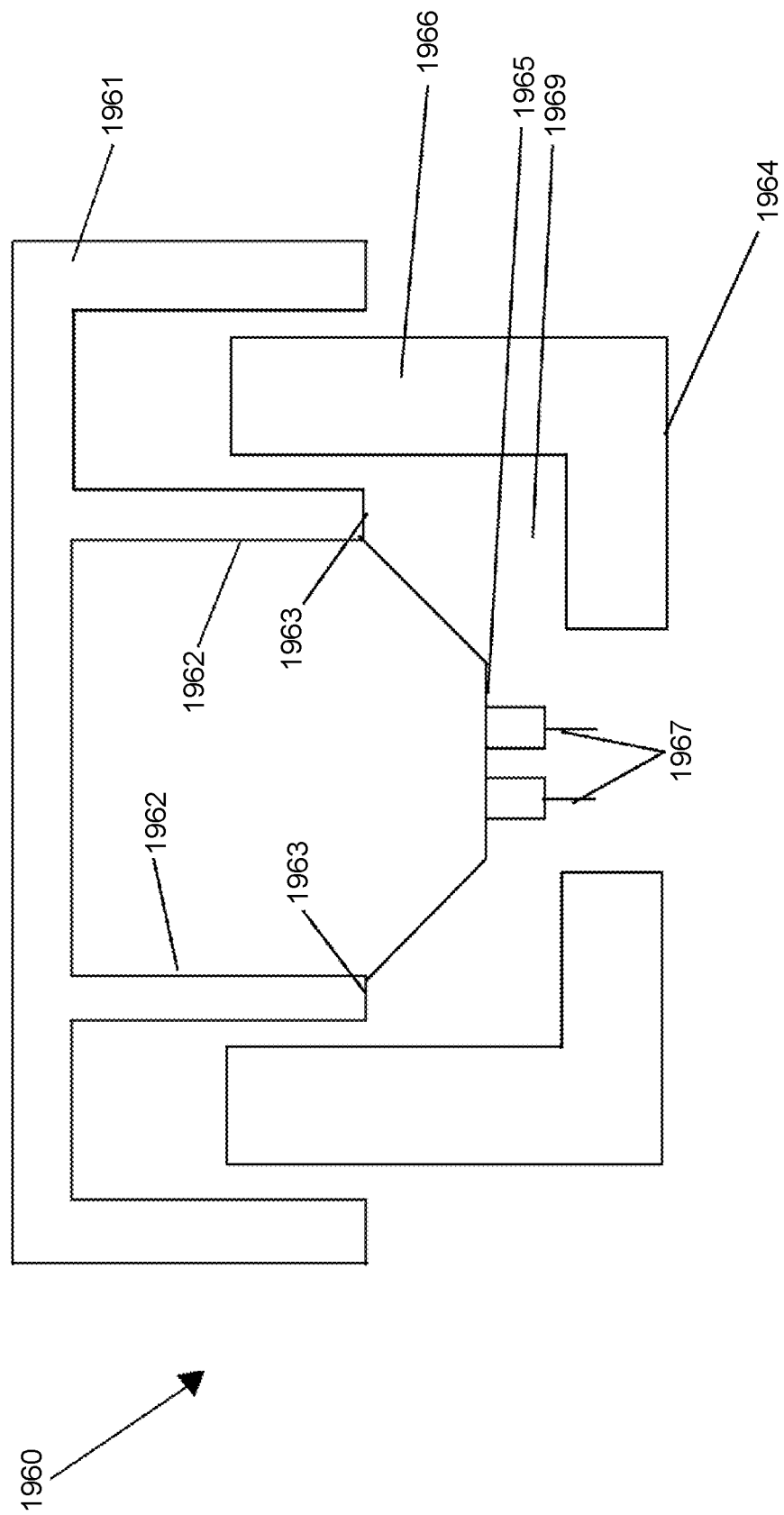
FIG. 19D is a front view of the handheld device showing an alternative embodiment of the mechanism for retracting the plunger of the handheld device.

To use the embodiment depicted in FIG. 19D, a user places the handheld device 1960 in FIG. 19D on a subject's skin and the user imparts a force on a lid 1961 to actuate the handheld device 1960. Lid 1961 contains a plurality of arms 1962 which are connected to a bi-stable spring 1963; the bi-stable spring 1963 holds the plunger 1965. The bi-stable spring 1963 has two distinct states or configurations and can automatically switch between the two states when an external force is imparted. In the initial state of the bi-stable spring 1963 (before any force is applied to the lid 1961), the plunger 1965 is located closer to the distal end 1964 of the body 1966. When the user imparts a force on the lid 1961 and displaces the plunger 1965 a defined distance distally in the lumen 1969, at least one of the plurality of needles 1967 penetrates the subject's skin and the bi-stable spring 1963 is triggered to flip to its alternate state, such as compaction, buckling, or otherwise retracting. When the bi-stable spring 1963 flips to its alternate state, the plunger 1965 retracts proximally, removing the plurality of needles 1967 from the subject's skin and creating a vacuum in a portion of the lumen 1969 called the vacuum creation space 1969.

Figure 19E:
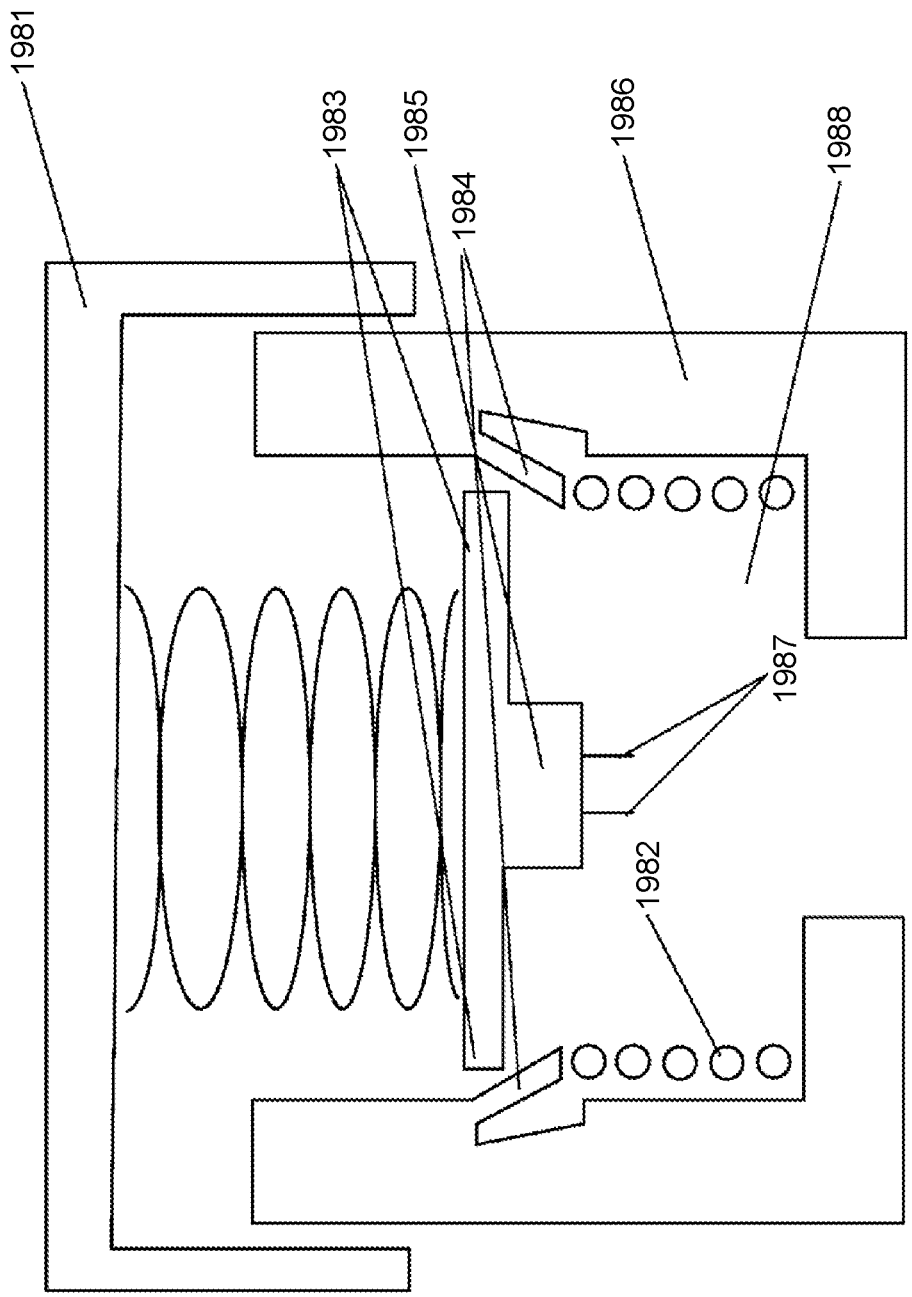
FIG. 19E is a front view of the handheld device showing an alternative embodiment of the mechanism for retracting the plunger of the handheld device.

To use the embodiment depicted in FIG. 19E, a user places the handheld device 1980 in FIG. 19E on a subject's skin and the user imparts a force on a lid 1981 to actuate the handheld device 1980. Lid 1981 is connected a traction spring 1982 set in a pre-extended state and connected to the plunger 1985. The plunger 1985 is kept in place by a plurality of arms 1983, which help to connect the plunger 1985 to the lid 1981 via the spring 1982. When the user imparts a force on the lid 1981, this transmits enough force in the distal direction through the spring 1982 to the plunger 1985 such that at least one of the plurality of needles 1987 penetrates the subject's skin. The user-imparted force pushes the plunger 1985 distally to reach a defined displacement, causing a plurality of protrusions 1984 on the body 1986 to break the plurality of arms 1983. As a result, the plunger 1985 disconnects from the lid 1981, allowing the traction spring 1982 to retract the plunger 1985, removing the plurality of needles 1987 from the subject's skin and creating a vacuum in the vacuum creation space 1988.

Figure 19F:
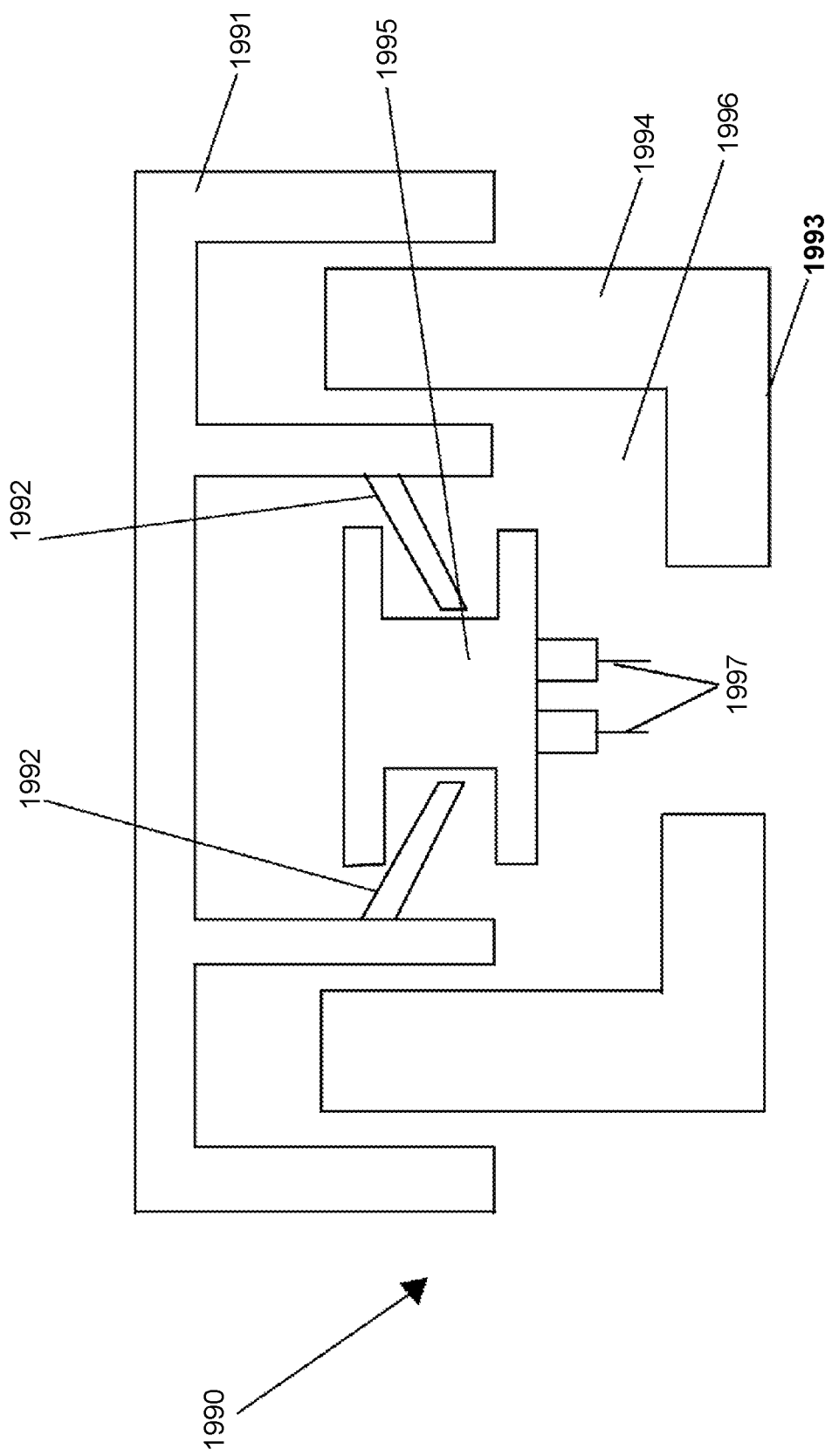
FIG. 19F is a front view of the handheld device showing an alternative embodiment of the mechanism for retracting the plunger of the handheld device.

To use the embodiment depicted in FIG. 19F, a user places the handheld device 1990 in FIG. 19F on a subject's skin and the user imparts a force on a lid 1991 to actuate the handheld device 1990. The lid 1991 contains a plurality of bi-stable springs 1992, which can exist in an upper and lower state. The plurality of bi-stable springs 1992 are initially in a lower state with the plurality of needles 1997 closer to the distal end 1993 of the body 1994. When the user imparts a force on the lid 1991, this transmits enough force to the plunger 1995 such that at least one of the plurality of needles 1997 penetrates the subject's skin. When the plunger 1995 reaches a defined displacement, the plurality of bi-stable springs 1992 change from the lower state to the upper state, retracting the plunger 1995, removing the plurality of needles 1997 from the subject's skin and creating a vacuum creation space 1996 in the lumen 1996.

Figure 20A:
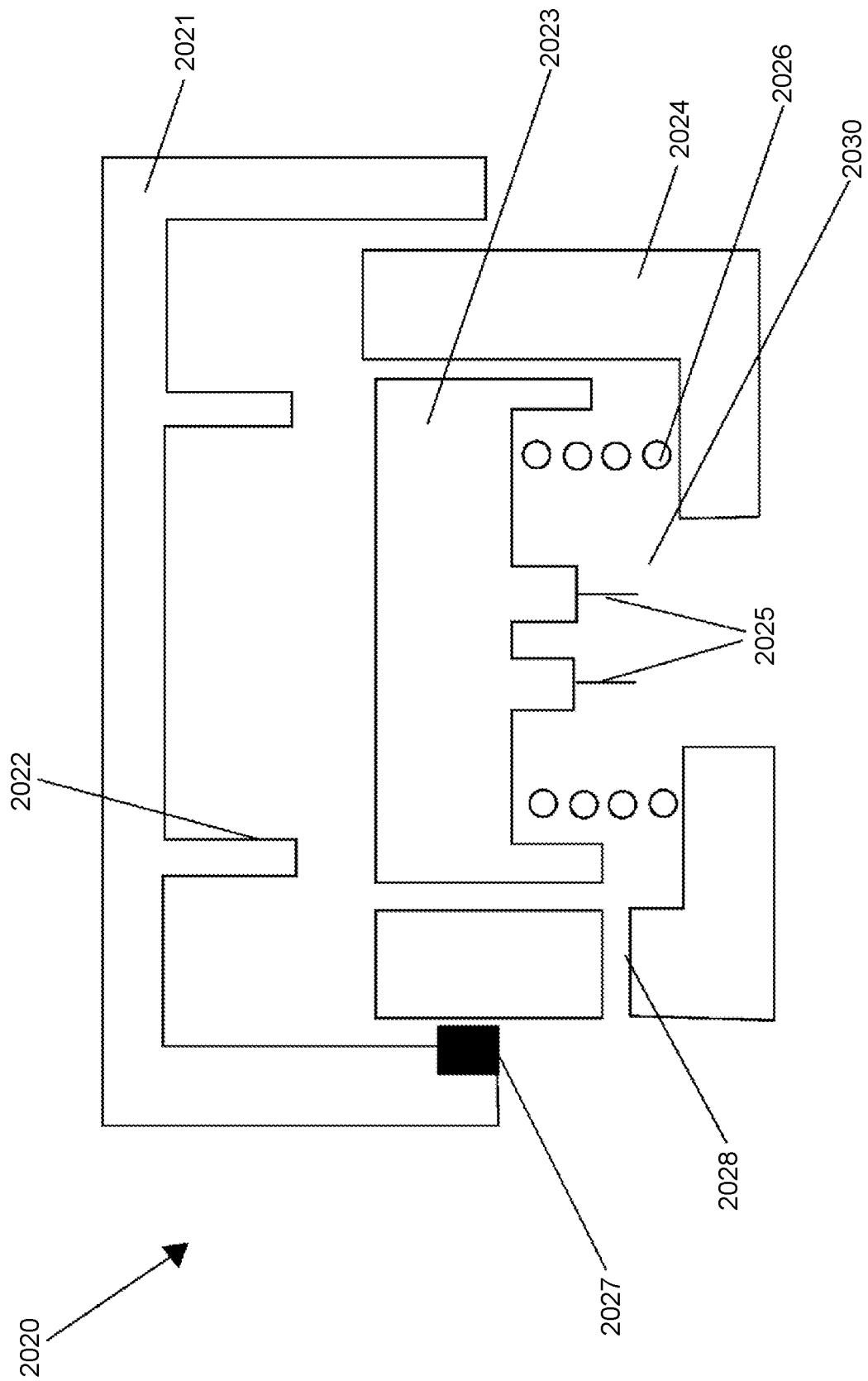
FIG. 20A is a front view of the handheld device showing an alternative embodiment of the mechanism for a one-way valve for the handheld device.

The various views depicted in FIGS. 20A-10C show exemplary embodiments of a one-way valve in the handheld device during and following actuation. More specifically, FIGS. 20A-10C depict various embodiments having one or more one-way air valves in fluid communication with the lumen of the body that are passively operated by a user's actuation of the handheld device. Generally speaking, when the device is used and the plunger is depressed, an excess of air in the body must be expelled from the area in the lumen distal to the plunger (between the plunger and the subject's skin) so as to create a vacuum when the plunger is retracted to the top position. As such, all of these drawings refer generally to methods that allow air to escape the lumen of the body when the plunger is depressed and prevent the re-entry of air into the lumen when the plunger is retracted. The various embodiments offer simpler and cheaper alternatives to that which is known in the art.

In an exemplary embodiment of the handheld device 2020 depicted in FIG. 20A, a user places the handheld device 2020 in FIG. 20A on a subject's skin and the user imparts a force on a lid 2021 to actuate the handheld device 2020. The lid 2021 contains a plurality of leg pieces 2022. When the user imparts a force on the lid 2021, the plurality of leg pieces 2022 come down and into contact with the plunger 2023, as described further in reference to FIG. 19A-9F, transmitting enough force to the plunger 2023 such that at least one of the plurality of needles 2025 penetrates the subject's skin. In various embodiments, the plurality of leg pieces 2022 are designed to radially splay but are also held inside of the body 2024 to ensure reliable contact with the plunger 2023 while the user actuates the handheld device 2020. Other embodiments, such as those described in reference to FIGS. 19A-9F are possible. When a user imparts a force on the lid 2021, the lid 2021 compresses the spring 2026 and moves distally to a defined displacement, allowing the spring 2026 to decompress and retract the plunger 2023, removing the plurality of needles 2025 from the subject's skin and creating a vacuum in the body 2024. Again, other embodiments, such as those described in reference to FIGS. 19A-9F are possible. In this embodiment, a gasket 2027 is mounted on the lid 2021 of the handheld device 2020 such that when force is applied to the lid, the gasket 2027 completely covers an air channel 2028 in the body 2024 (wherein the air channel 2028 is in fluid communication with the lumen 2030, and the plunger 2023 moves freely in the body 2024 while the one-way airtight seal is maintained by the gasket 2027 being positioned at the air channel 2028.

Figure 20B:
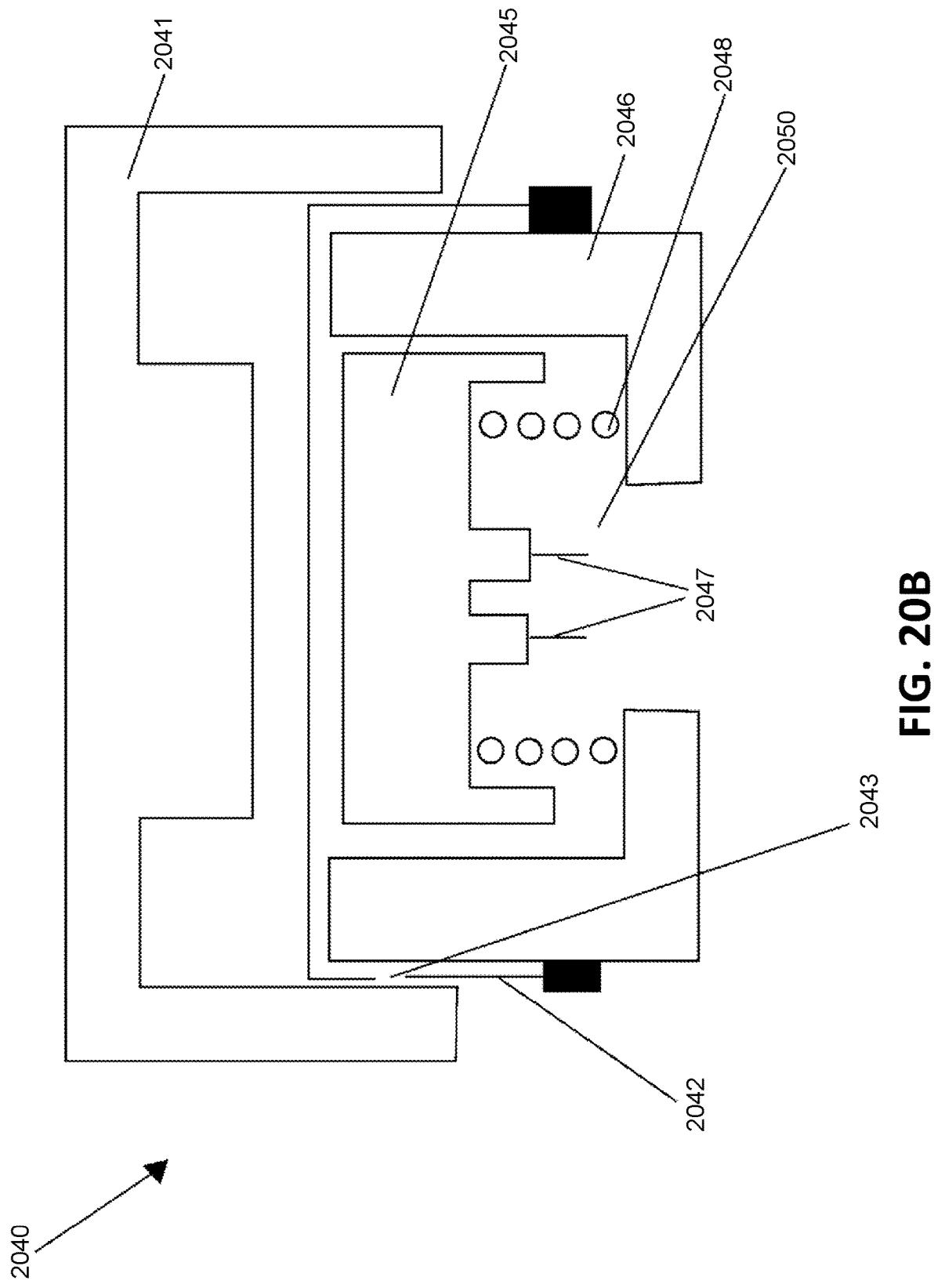
FIG. 20B is a front view of the handheld device showing an alternative embodiment of the mechanism for a one-way valve for the handheld device.

In an exemplary embodiment of the handheld device 2040 depicted in FIG. 20B, a user places the handheld device 2040 in FIG. 20B on a subject's skin and the user imparts a force on a lid 2041 to actuate the handheld device 2040. In various embodiments, the handheld device 2040 further comprises an elastic membrane 2042, further comprising a small hole or holes 2043, such that when the plunger 2045 is depressed, the air pressure in the lumen 2050 increases and airflow is directed outwards on the elastic membrane 2042 such that the elastic membrane 2042 pushes away from a flat surface of the body 2046, and air can pass through. Conversely, when the plunger 2045 is retracted following operation of the needles 2047 and subsequent actuation of the springs 2048, the airflow back toward the lumen 2050 is reintroduced into the small hole or holes 2043, thus causing the elastic membrane 2042 to press against the body 2046, thereby establishing a one-way airtight seal around the hole or holes 2043 and creating a vacuum within the lumen 2050.

Figure 20C:
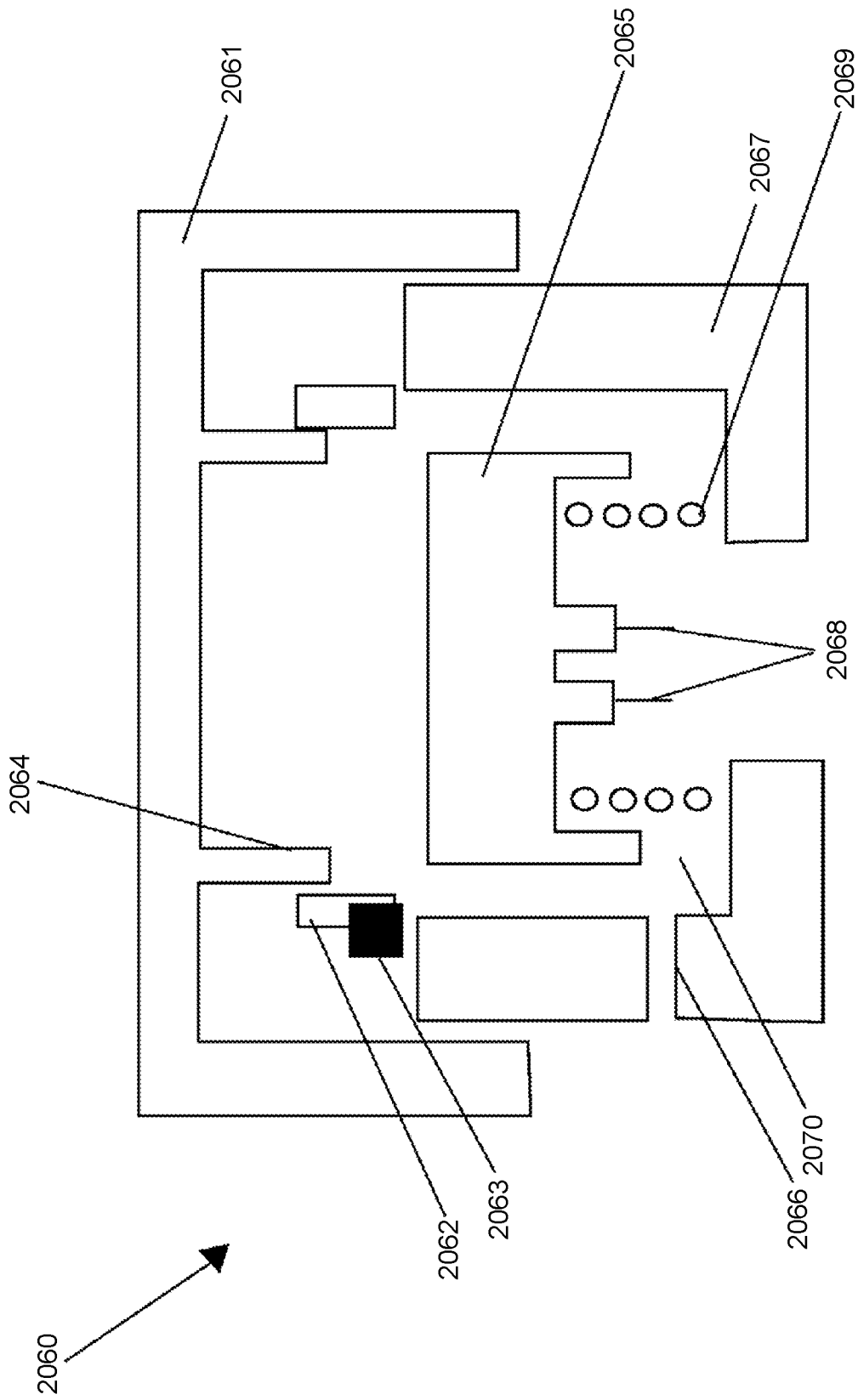
FIG. 20C is a front view of the handheld device showing an alternative embodiment of the mechanism for a one-way valve for the handheld device.

In an exemplary embodiment of the handheld device 2060 depicted in FIG. 20C, a user places the handheld device 2060 in FIG. 20C on a subject's skin and the user imparts a force on a lid 2061 to actuate the handheld device 2060, as has been previously described. In various embodiments. at least one sealing component 2062 is operationally coupled to at least one separate leg component 2064. In these embodiments, the at least one sealing component 2062 further comprises at least one gasket 2063 that, upon actuation of the handheld device 2060 by the user depressing the lid 2061, forms a fluidic seal with the channel 2066, such that the seal remains following the retraction of the plunger 2065 by way of the spring 2069, thereby creating a vacuum in the lumen 2070 of the body 2067 following deployment of the needles 2068.

Figure 21:
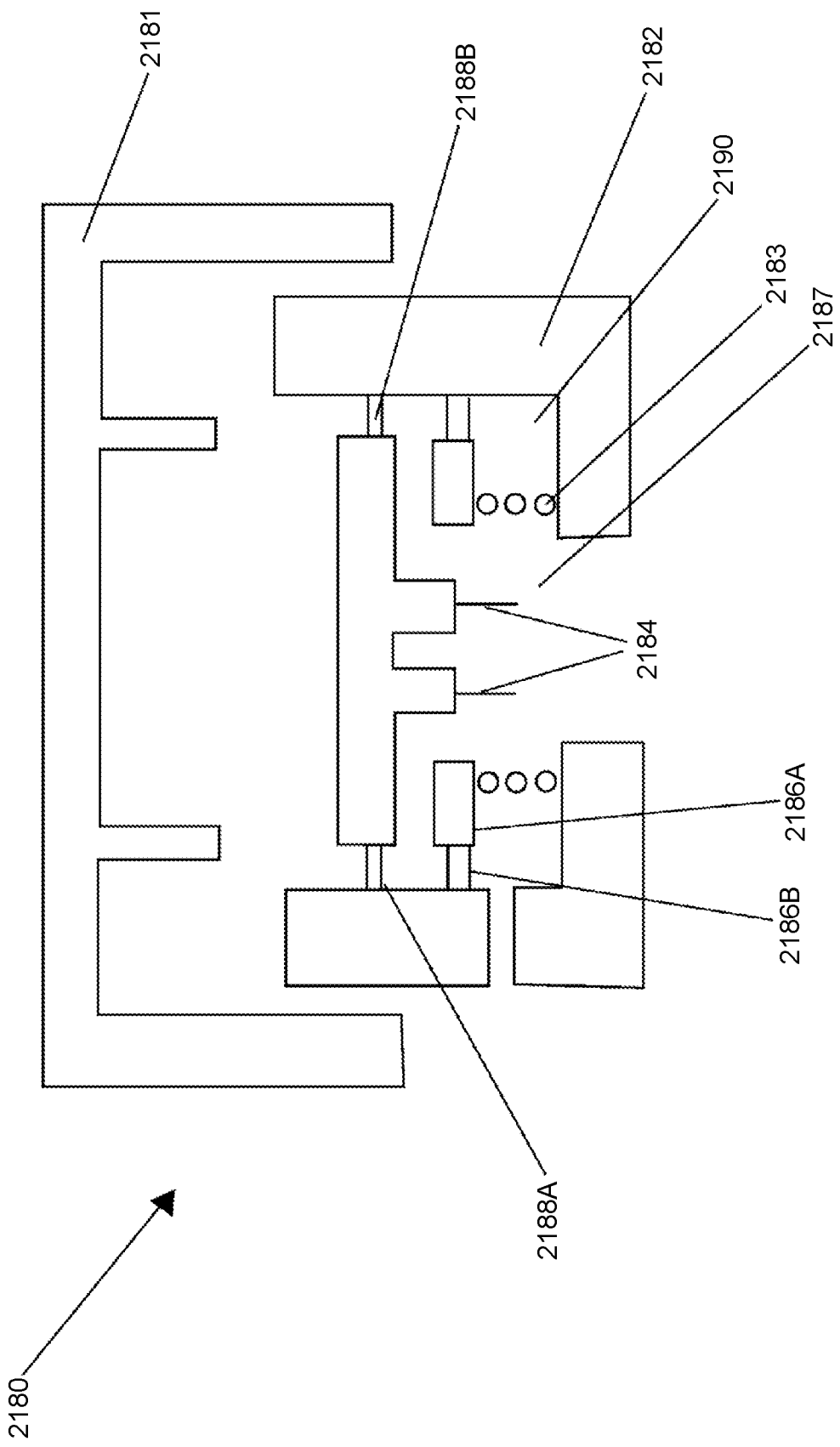
FIG. 21 is a front view of the handheld device showing an alternative embodiment of the mechanism for retracting the plunger of the handheld device.

FIG. 21 depicts an exemplary embodiment wherein the handheld device 2180 comprises a lid 2181, a body 2182, needles 2184 and a plunger 2185, as has been previously described. In various embodiments, the handheld device further comprises a pre-loaded retraction spring 2183. The pre-loaded retraction spring 2183 is pre-loaded with at least one frangible trigger 2186A, 2186B. In the embodiment depicted in FIG. 21, the frangible trigger 2186A, 2186B further comprises a plurality of components, a cover 2186A and a thinner anchor 2186B. Other embodiments are possible. The needles 2184 are also covered with frangible covers, such that in operation, the plunger 2185 is depressed, first breaking the frangible covers 2187 over the needles 2184 so that the needles may enter the skin, and subsequently breaking the frangible trigger 2186A, 2186B and deploying the spring 2183 so as to remove the needles 2184 from the skin. Thereby, in these embodiments, the user may simply compress the lid and the puncture of the skin, collection of the bodily fluid and retraction of the needles will all occur in automatic succession, thus increasing the usability and reliability of the handheld device. FIG. 21 also depicts an embodiment wherein the handheld device further comprises a channel 2188 for creation of a vacuum, various embodiments of which are described in detail in relation to FIGS. 20A-20C. In these embodiments, the channel 2188 can be closed by way of a gasket, thereby creating a fluidic seal and vacuum in the lumen 2190 of the body 2184 when the plunger 2185 is depressed. The various anchors 2188A, 2188B are of a breakable substrate such that when the plunger 2185 is actuated to and past each anchor point, the anchors are broken, causing a release of the plunger 2185 and subsequently a release of the preloaded spring 2183.

Figure 22A:
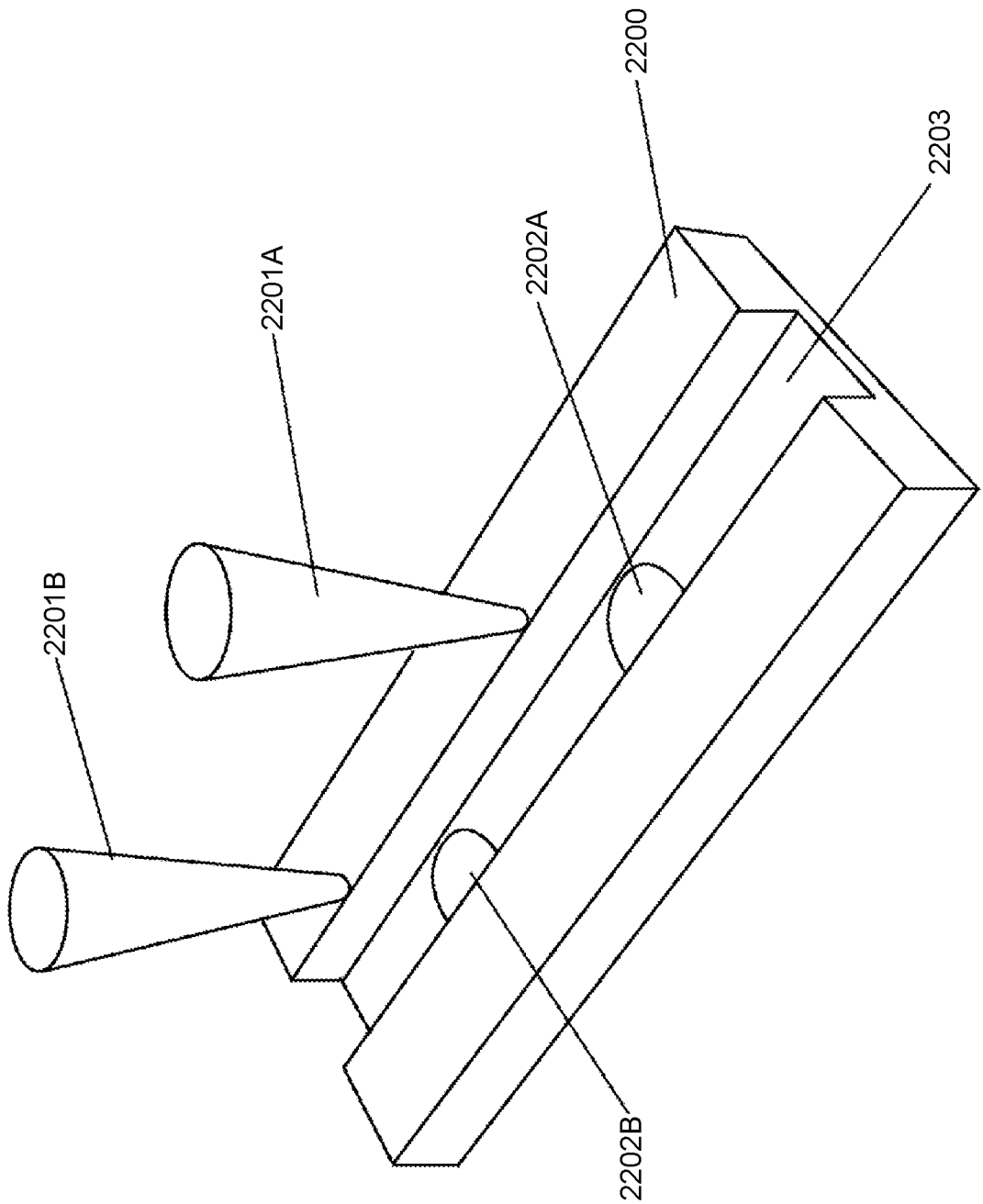
FIG. 22A is a perspective view of the handheld device showing alternative embodiments of the handheld device.
Figure 22B:
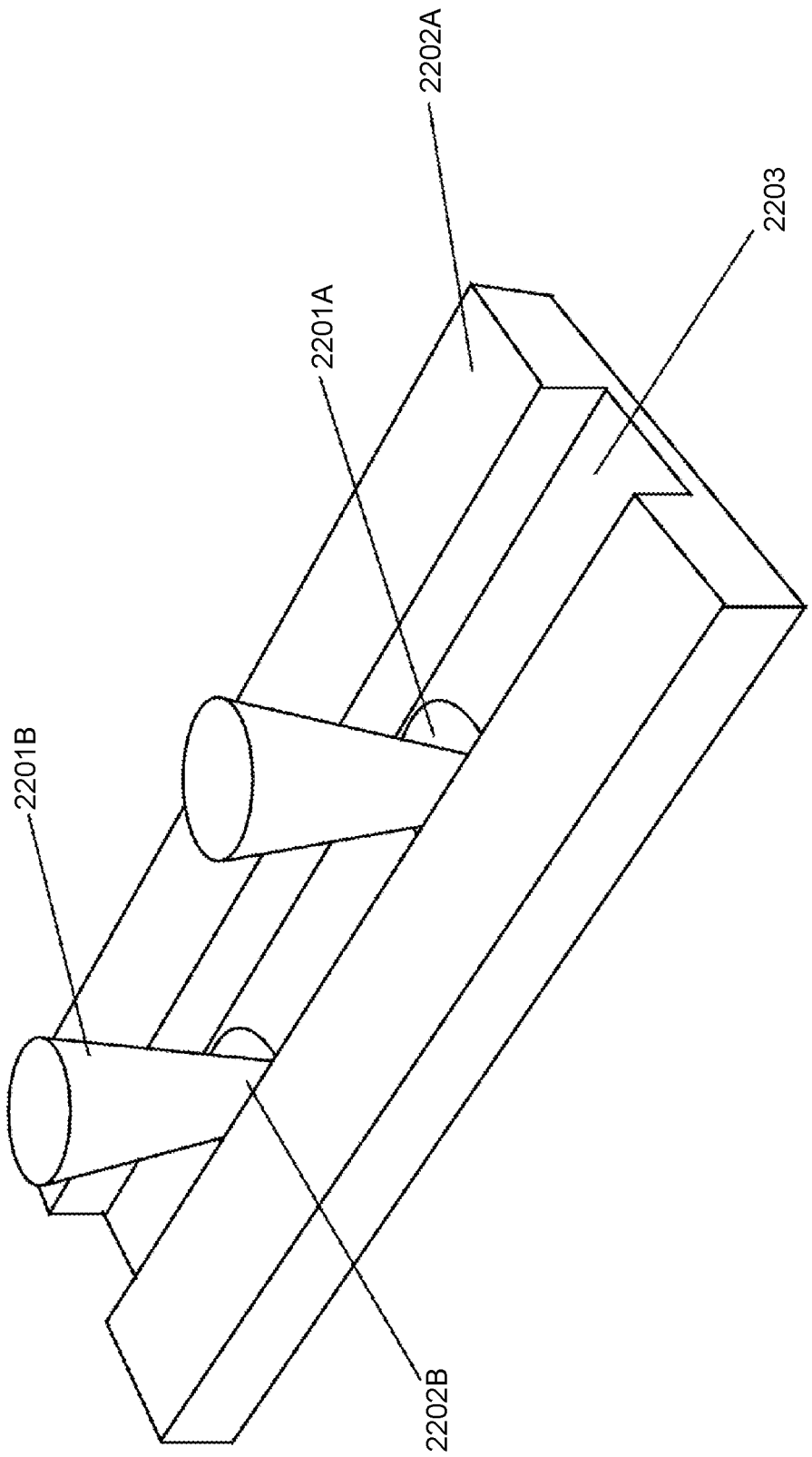
FIG. 22B is a perspective view of the handheld device showing an alternative embodiment of the handheld device.
Figure 22C:
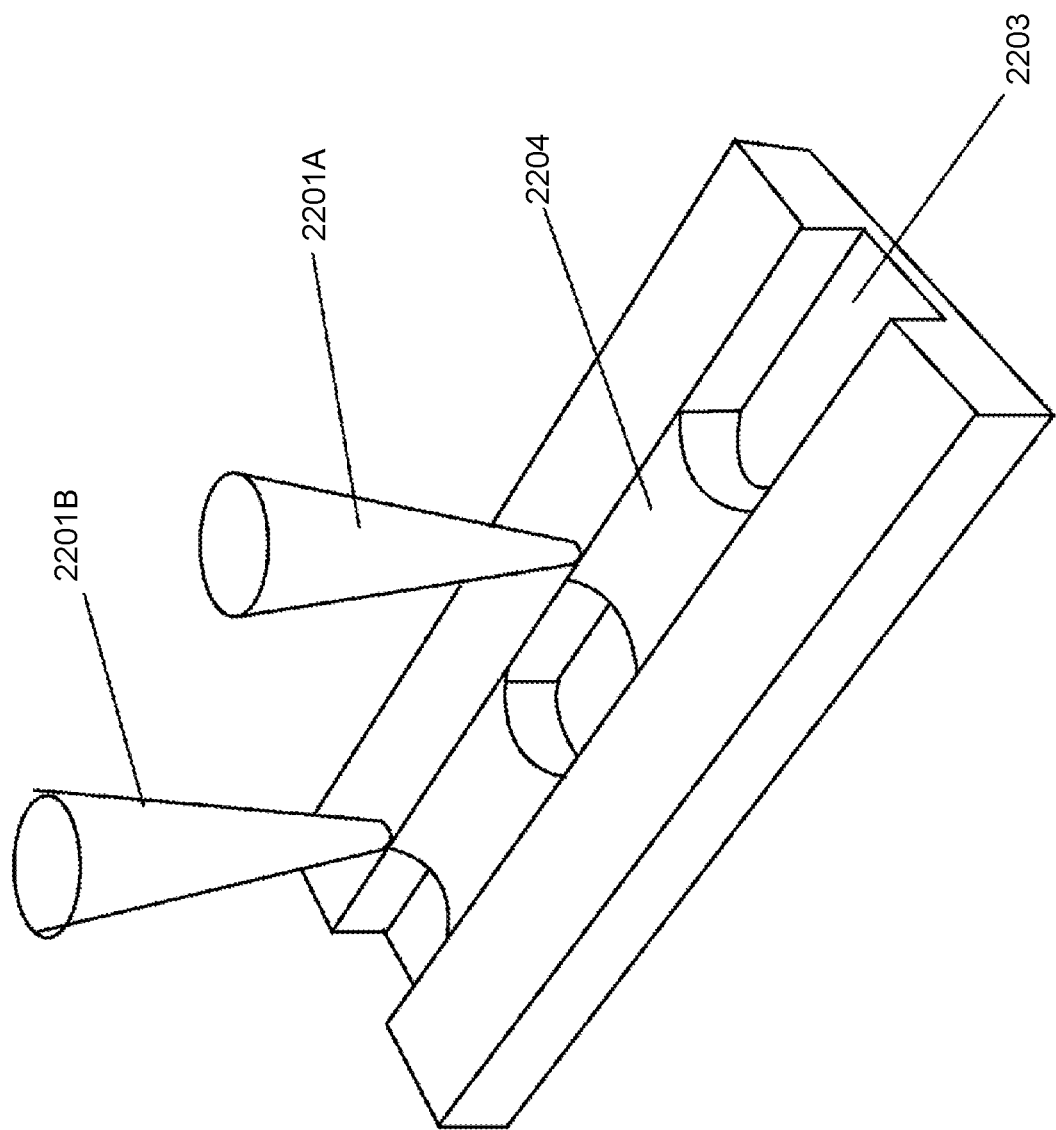
FIG. 22C is a perspective view of the handheld device showing an alternative embodiment of the handheld device.

FIGS. 22A through 22C depict various embodiments of the arrangement of needles in the handheld device. In the embodiment depicted in FIG. 22A, individual needles 301A, 301B are aligned over individual isolated openings 2202A, 2202B spaced throughout the channel 2203 created in the bottom of the handheld device 2200.

FIG. 22B depicts the embodiment of FIG. 22A, wherein each of the multiple needles 2201A, 2201B can be lowered to a lower position, as described previously, through the openings 2202A, 2202B thereby perforating the skin below and performing a bodily fluid draw into the channel 2203.

FIG. 22C depicts the embodiment of FIG. 22B, wherein the needles 2201A, 2201B have been retracted. Following retraction, the bodily fluid 2204 is captured by the channel 2203. Theses embodiments thereby allow multiple bodily fluid extraction sites to be collected into the same fluidic handling system even in the event that one or more of the extraction sites do not extract any fluid. The bodily fluid 2204 flowing into the fluidic handling mechanism, or channel 2203 from one of the extraction sites is able to fill the device by itself, or connect with the fluid from a different extraction site without causing a blockage or air bubble in the fluidic paths.

Figure 23A:
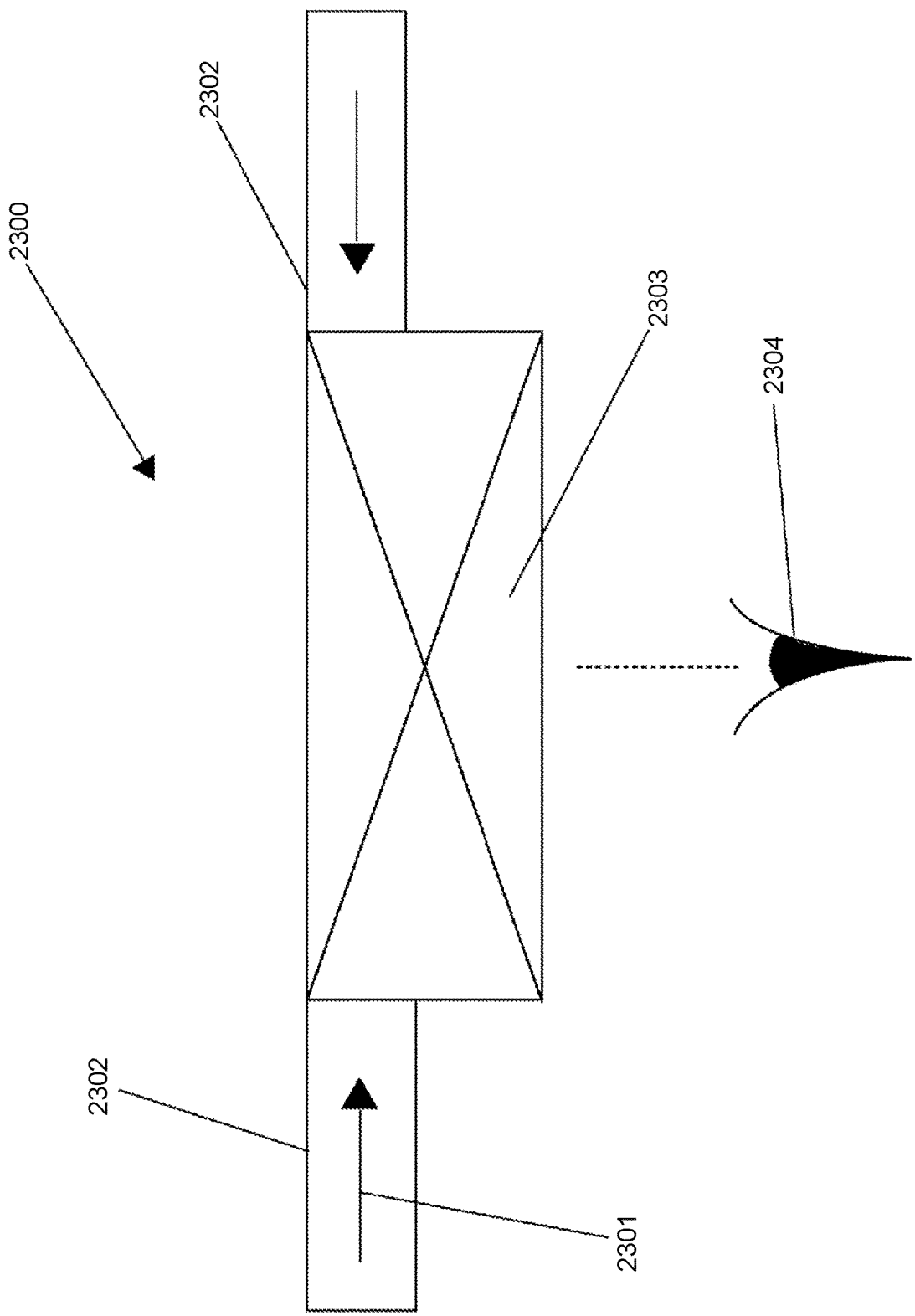
FIG. 23A is a front view of the handheld device showing exemplary embodiments for collection and analysis of bodily fluid in the at least one sensing area.
Figure 23B:
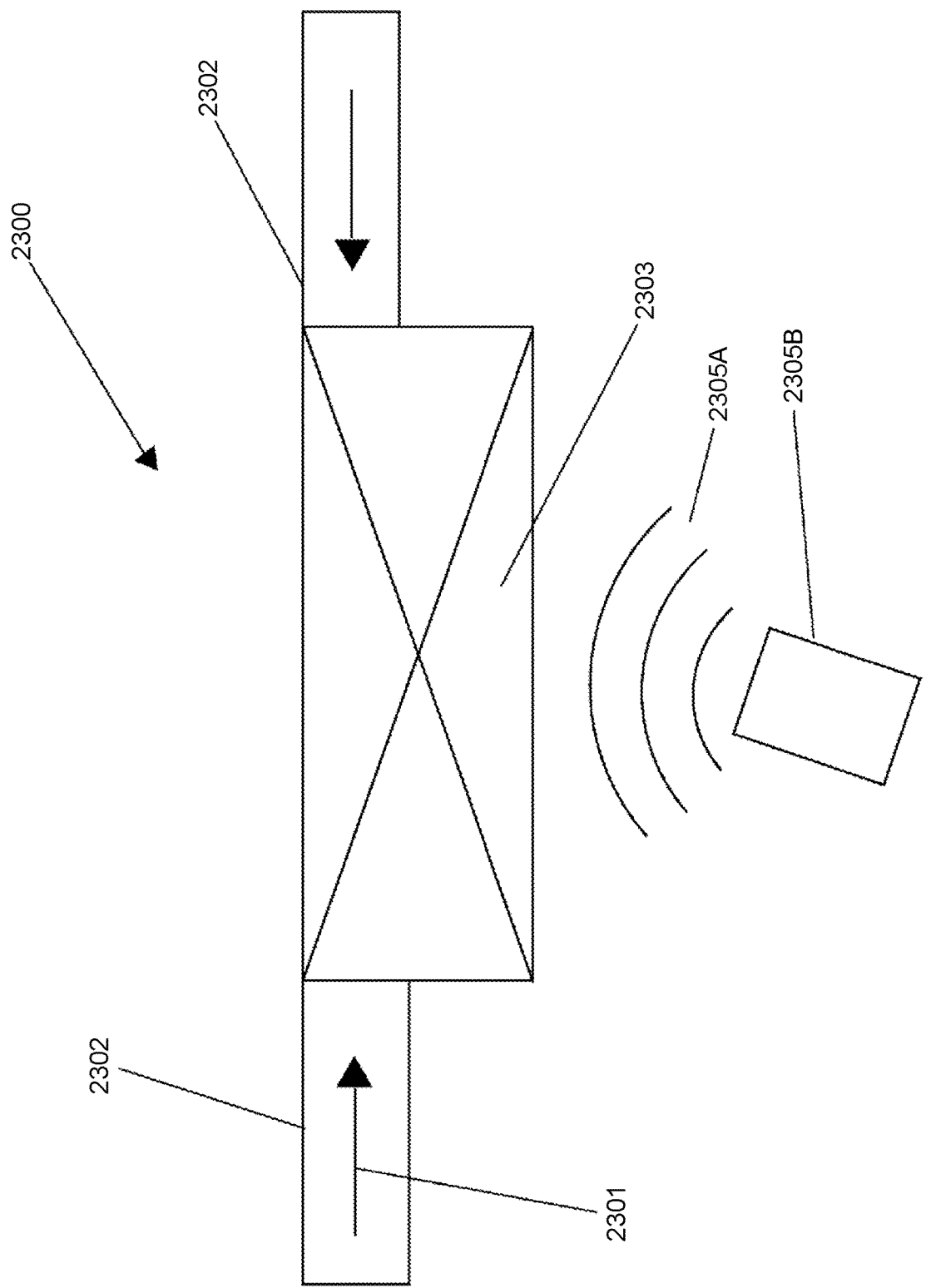
FIG. 23B is a front view of the handheld device showing exemplary embodiments for collection and analysis of bodily fluid in the at least one sensing area.
Figure 23C:
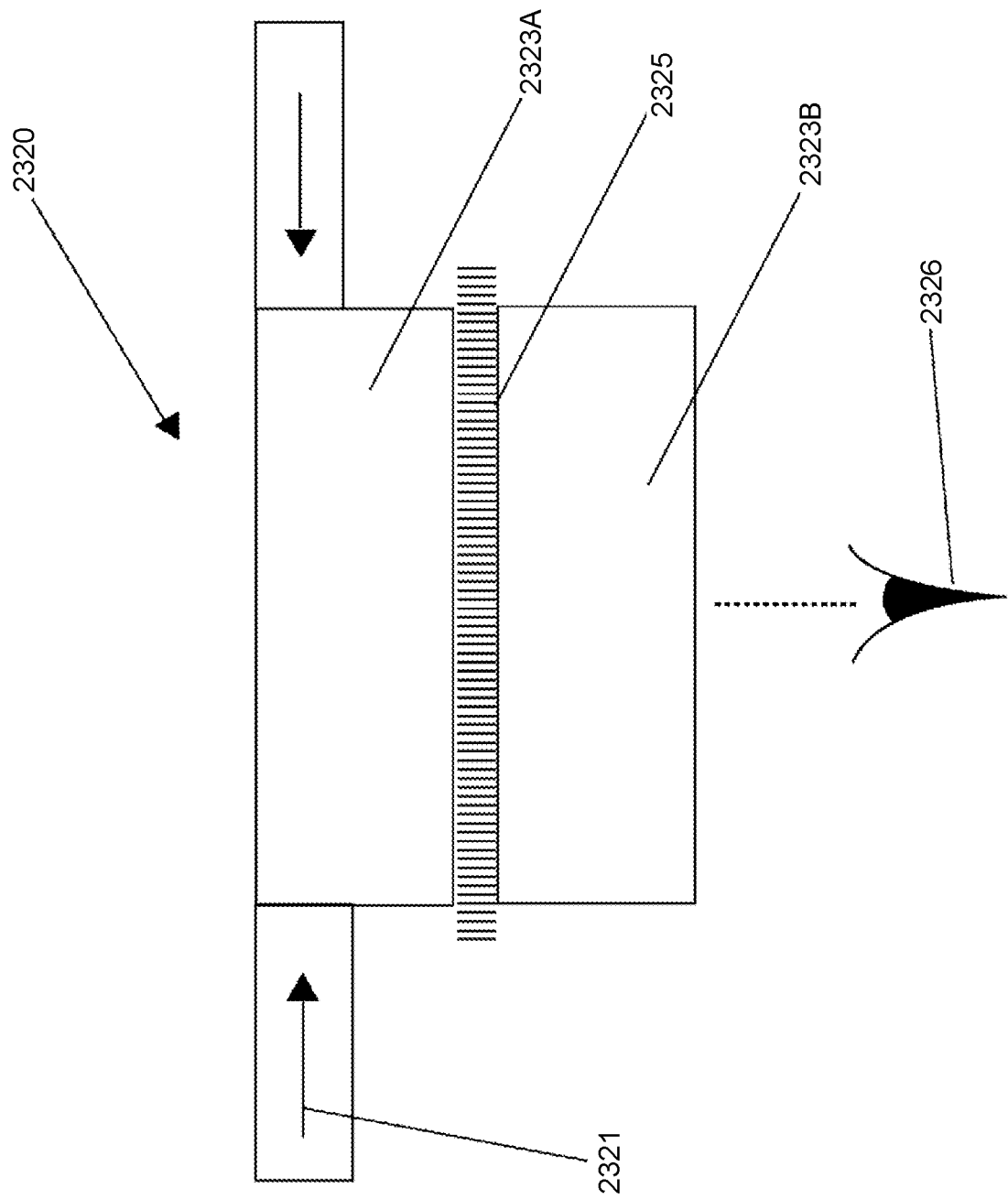
FIG. 23C is a front view of the handheld device showing exemplary embodiments for collection and analysis of bodily fluid in the at least one sensing area.

FIGS. 23A through 23C depict various embodiments for sensing biomarkers in the bodily fluid collected from the patient by the device and flowing in the channels. After sample preparation, the at least one sensing area 2303 analyzes the bodily fluid for chemicals or particles of interest and provides a method of readout that may be electrical, visual, or audial. A visual readout may include chemistries that result in a change in color, fluorescence, or emitted light from or resulting from the sensing region that would be detectable by any form of optics or visually by the user. An electrical readout may include electrodes within the at least one sensing area 2303 that detect a change in resistance, capacitance, voltage, or current within the sensing region resulting from an accumulation of compounds that modify the electrical properties of the fluid. An audial readout may include the transmission of information from the sensing region to the user based on an audial medium.

According to the handheld device 2300 embodiment of FIGS. 23A-23B, the fluid 2301 flows into the handheld device 2300 by way of a channel 2302. The handheld device further comprises at least one sensing area 2303. In various embodiments, the at least one sensing area further comprises either a fluid reservoir or an absorbent mesh to hold the fluid 2301. As depicted in the embodiment of FIG. 23A, after the bodily fluid has collected in the at least one sensing area 2303, a chemical or physical reaction in the at least one sensing area 2303 displays a color or texture change 23023 visible from the back side of the device. In an alternative embodiment shown in FIG. 23B, an electrical signal 2305A can be outputted by the sensing area 2303 that can be detected by a receiver 2305B, such as a smartphone.

In the embodiments depicted in FIGS. 23A-23B, the at least one sensing area is a single, unified unit for collection and analysis of the bodily fluid. In other various embodiments, an exemplary handheld device 2320 of which is depicted in FIG. 23C, the at least one sensing area is subdivided into a plurality of chambers 2323A, 2323B by way of a membrane 2325 so as to separate particles or fractionate fluids from the incoming fluid, 2321 so as to detect specific biomarkers or perform other analysis for detection, either visually or by other chemical or electronic means, as is well known in the art. By way of example, such an embodiment could separate plasma from blood. In various embodiments, a visual or electrical detection system can be placed on the back side allowing to perform a readout.

Although the disclosure has been described with reference to preferred embodiments, persons skilled in the art will recognize that changes may be made in form and detail without departing from the spirit and scope of the disclosed apparatus, systems and methods.

We claim:

1. A method of collecting bodily fluid from a subject via a collection device comprising, the method comprising:
   providing a collection device comprising a housing including a lower surface having an opening, a skin-piercing feature positioned at least partially within the housing, and a collection reservoir coupled to the housing, wherein—
      the collection reservoir is elongate and extends along a longitudinal axis,
      the collection reservoir has a first end portion, a second end portion, and an opening proximate the first end portion, and
      the collection reservoir extends generally parallel to the lower surface of the housing;
   positioning the lower surface of the housing against skin of the subject such that the opening of the collection reservoir is positioned above the second end portion of the collection reservoir relative to a gravitational field;
   activating a vacuum source positioned within the housing and different than the collection reservoir to apply negative pressure against the skin of the subject through the opening in the lower surface of the housing;
   piercing the skin of the subject with the skin-piercing feature to form an incision in the skin of the subject; and
   collecting bodily fluid in the collection reservoir, wherein the bodily fluid flows from the incision into the opening of the collection reservoir via a force from the negative pressure and/or a force from the gravitational field.

2. The method of claim 1 wherein the bodily fluid flows via the force from the negative pressure and the force from the gravitational field.

3. The method of claim 1 wherein piercing the skin of the subject includes moving the skin-piercing feature at least partially past the lower surface of the collection device.

4. The method of claim 1, further comprising decoupling the collection reservoir from the housing after a predetermined time has elapsed and/or after a predetermined amount of the bodily fluid has been collected in the collection reservoir.

5. The method of claim 1 wherein collecting the bodily fluid includes collecting the bodily fluid for a predetermined time or collecting a predetermined amount of the bodily fluid in the collection reservoir.

6. The method of claim 1, further comprising positioning a cap on the collection reservoir over the opening after collecting the bodily fluid in the collection reservoir.

7. The method of claim 1 wherein the bodily fluid is blood.

8. The method of claim 1 wherein positioning the lower surface of the housing against the skin of the subject includes positioning the lower surface of the housing against an arm of the subject.

9. The method of claim 1 wherein positioning the lower surface of the housing against the skin of the subject includes positioning the lower surface of the housing against an upper arm of the subject.

10. The method of claim 1 wherein activating the vacuum source includes depressing an actuator of the collection device.

11. The method of claim 1 wherein the skin-piercing feature is a blade.

12. The method of claim 1, further comprising at least one reagent positioned within the collection reservoir.

13. The method of claim 1 wherein the collection reservoir is positioned at least partially within the housing.

14. The method of claim 1 wherein the housing defines a chamber over the opening in the lower surface, wherein the skin-piercing feature is positioned at least partially within the chamber, and wherein the method further comprises generating the negative pressure within the chamber via the vacuum source.

15. A method of collecting bodily fluid from a subject, the method comprising:
   releasably coupling a collection reservoir to a collection device having a lower surface, wherein the collection reservoir is elongate and extends along a longitudinal axis, wherein the collection reservoir has a first end portion, a second end portion, and an opening proximate the first end portion, and wherein releasably coupling the collection reservoir to the collection device comprises positioning the collection reservoir generally parallel to the lower surface of the collection device;
   positioning a lower surface of the collection device against skin of the subject such that the opening of the collection reservoir is positioned above the second end portion of the collection reservoir relative to a gravitational field;

activating a vacuum source positioned within the collection device and different than the collection reservoir to apply negative pressure against the skin of the subject through an opening in the lower surface of the collection device;

piercing the skin of the subject with a skin-piercing feature to form an incision in the skin of the subject; and collecting bodily fluid in the collection reservoir, wherein the bodily fluid flows from the incision into the opening of the collection reservoir via a force from the negative pressure and/or a force from the gravitational field.

16. The method of claim 15 wherein the collection device includes a housing, and wherein releasably coupling the collection reservoir to the collection device includes positioning the collection reservoir at least partially within the housing.

17. The method of clam 15 wherein the collection device includes a housing defining a chamber over the opening in the lower surface, wherein the skin-piercing feature is positioned at least partially within the chamber, and wherein the method further comprises generating the negative pressure within the chamber via the vacuum source.

18. The method of claim 14 wherein the bodily fluid flows via the force from the negative pressure and the force from the gravitational field, and wherein piercing the skin of the subject includes moving the skin-piercing feature past the lower surface of the collection device.

19. The method of claim 14 wherein positioning the lower surface of the collection device against the skin of the subject includes positioning the lower surface of the collection device against an upper arm of the subject, and wherein activating the vacuum source includes depressing an actuator of the collection device.

20. A method of collecting bodily fluid from a subject via a collection device comprising, the method comprising:
providing a collection device comprising a housing, an actuator, a skin-piercing feature, and a collection reservoir, wherein—
the actuator is coupled to the housing;
the housing defines a chamber and has a lower surface including an opening, the collection reservoir is coupled to the housing and at least partially positioned within the chamber,
the skin-piercing is positioned at least partially within the chamber,
the collection reservoir is elongate and extends along a longitudinal axis,
the collection reservoir has a first end portion, a second end portion, and an opening proximate the first end portion, and
the collection reservoir extends generally parallel to the lower surface of the housing;

positioning the lower surface of the housing against skin of an arm of the subject such that the opening of the collection reservoir is positioned above the second end portion of the collection reservoir relative to a gravitational field;

actuating the actuator to activate a vacuum source positioned within the chamber and different than the collection reservoir to apply negative pressure against the skin of the subject through the opening in the lower surface of the housing;

piercing the skin of the subject with the skin-piercing feature to form an incision in the skin of the subject; and collecting bodily fluid in the collection reservoir, wherein the bodily fluid flows from the incision into the opening of the collection reservoir via a force from the negative pressure and a force from the gravitational field; and decoupling the collection reservoir from the housing after a predetermined time has elapsed and/or after a predetermined amount of the bodily fluid has been collected in the collection reservoir.

21. The method of claim 1 wherein the second end portion of the collection reservoir is closed.

22. The method of claim 1 wherein positioning the lower surface of the housing against skin of the subject includes positioning the lower surface such that the skin-piercing feature is positioned above the opening of the collection reservoir relative to the gravitational field.

23. The method of claim 1, further comprising decoupling the collection reservoir from the housing and the skin-piercing feature.

24. The method of claim 15 wherein the second end portion of the collection reservoir is closed.

25. The method of claim 15 wherein positioning the lower surface of the housing against skin of the subject includes positioning the lower surface such that the skin-piercing feature is positioned above the opening of the collection reservoir relative to the gravitational field.

26. The method of claim 15, further comprising decoupling the collection reservoir from the collecting device and the skin-piercing feature.

27. The method of claim 20 wherein the second end portion of the collection reservoir is closed.

28. The method of claim 20 wherein positioning the lower surface of the housing against skin of the subject includes positioning the lower surface such that the skin-piercing feature is positioned above the opening of the collection reservoir relative to the gravitational field.

29. The method of claim 20, further comprising decoupling the collection reservoir from the housing and the skin-piercing feature.

* * * * *